US011779608B2

(12) United States Patent
Alsamhary et al.

(10) Patent No.: US 11,779,608 B2
(45) Date of Patent: Oct. 10, 2023

(54) METHOD OF TREATING A BACTERIAL INFECTION USING COLOSTRUM

(71) Applicant: KING SAUD UNIVERSITY, Riyadh (SA)

(72) Inventors: Khawla Ibrahim Alsamhary, Riyadh (SA); Nagwa Mohamed Mohamed Amin Aref, Cairo (EG); Adel Almogren, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 139 days.

(21) Appl. No.: 17/160,070

(22) Filed: Jan. 27, 2021

(65) Prior Publication Data

US 2021/0275594 A1 Sep. 9, 2021

Related U.S. Application Data

(62) Division of application No. 16/809,882, filed on Mar. 5, 2020, now Pat. No. 10,933,097.

(51) Int. Cl.
*A61K 35/20* (2006.01)
*A61P 31/04* (2006.01)
*A61K 9/19* (2006.01)

(52) U.S. Cl.
CPC ............... *A61K 35/20* (2013.01); *A61K 9/19* (2013.01); *A61P 31/04* (2018.01)

(58) Field of Classification Search
CPC .................................. A61K 9/19; A61K 35/20
See application file for complete search history.

(56) References Cited

U.S. PATENT DOCUMENTS

| | | | |
|---|---|---|---|
| 7,939,118 B2 | 5/2011 | Stahl | |
| 8,409,592 B2 | 4/2013 | Vidal | |
| 8,475,789 B2 | 7/2013 | Bisgaard-Frantzen | |
| 9,555,084 B2 | 1/2017 | Bartorelli et al. | |
| 9,956,283 B2 | 5/2018 | Kvistgaard | |
| 2005/0175597 A1 | 8/2005 | Rawlin | |
| 2008/0081076 A1 | 4/2008 | Lisonbee | |
| 2011/0008361 A1 | 1/2011 | Bragger | |
| 2011/0182943 A1 | 7/2011 | Kanwar et al. | |
| 2019/0134096 A1 | 5/2019 | Ilan | |

FOREIGN PATENT DOCUMENTS

| | | |
|---|---|---|
| CN | 102524407 A | 7/2012 |
| WO | 2007000648 A1 | 1/2007 |

OTHER PUBLICATIONS

Merin, U. et al., "A comparative study of milk serum proteins in camel (Camelus dromedarius) and bovine colostrum," Livestock Production Science 67, No. 3, 2001, 297-301.
Sugisawa, H. et al., "A Low-molecular-weight Fraction of Bovine Colostrum and Milk Enhances the Oxidative Burst Activity of Polymorphonuclear Leukocytes," Vet. Res. Comm., 27(6), pp. 453-461, Sep. 2003.
Mal, G. and Pathak, K. M. L., "Camel Milk and Milk Products," SMVS Dairy Year Book, pp. 97-103, 2010.
Ismael, A. B. et al., "Development of New Strategy for Non-Antibiotic Therapy: Dromedary Camel Lactoferrin Has a Potent Antimicrobial and Immunomodulator Effects," Adv. in Inf. Dis., 3, pp. 231-237, 2013.
Mustafa, E. A. et al., "The Effect of Mixing Different Percentages of Cow Milk on the Physiochemical Characteristics of Camel Milk Yoghurt and the Sensory Evaluation of Yoghurt," World Journal of Pharmacy and Pharmaceutical Sciences, vol. 4, Issue 9, 2015, pp. 180-190.
Zeineb, J. et al., "Camel Colostrum: Nutritional Composition and Improvement of the Antimicrobial Activity After Enzymatic Hydrolysis," Emir. J. Food Agric., 2015, 27(4): pp. 384-389.
Singh, R.et al., "Camel Milk: an Important Natural Adjuvant," Agricultural Research, Sep. 21, 2017, 6(4), pp. 327-340.
Mahdi, L. et al., "Treatment strategy by lactoperoxidase and lactoferrin combination: Immunomodulatory and antibacterial activity against rnultidrug-resistant Acinetobacter baumannii," Microb. Pathog., 114: pp. 147-152, Jan. 2018.
Alluwaimi, A. M. et al., "The Cytokine Markers in *Staphylococcus aureus* Mastitis of Bovine Mammary Gland," J. Vet. Med. B. Infect. Dis. Vet. Public Health, 50(3): pp. 105-111, 2003.
Chen, C., et al., "Inhibitory Effects of Bovine Colostrum Protein Hydrolysates on Human Leukemic U937 Cell Growth," J. of Food and Drug Analysis, 19(3): pp. 309-317, 2011.
Chen, H.D. et al., "Memory CD8+ T Cells in Heterologous Antiviral Immunity and Immunopathology in the Lung," Nature Immunology, 2(11): pp. 1067-1076 (2001).
Clerici, M., et al., "Evaluation of Bovine-Derived Lacteal Complex Supplementation on Gene Expression in BALB/c Mice," Nutrition and Dietary Supplements, 3: pp. 89-92, 2011.
Garcia-Alvarez, F., et al., "Interleukin-1, Interleukin-6, and Interleukin-10 Responses After Antibiotic Treatment in Experimental Chronic *Staphylococcus aureus* Osteomyelitis," J. Orthop. Sci. 11(4): pp. 370-374, 2006.
Giese, M. J., et al., "Cytokine Expression in a Rat Model of *Staphylococcus aureus* Endophthalmitis." IOVS Resports, 39(13): pp. 2785-2790, 1998.
Hagiwara, K., et al., "Detection of Cytokines in Bovine Colostrum," Vet. Immunol. Immunopathol., 76(3-4): pp. 183-190, 2000.
Jimenez, E., et al., "Assessment of the Bacterial Diversity of Human Colostrum and Screening of *Staphylococcal* and Enterococcal Populations for Potential Virulence Factors," Res. Microbiol., 159(9-10): pp. 595-601, 2008.

(Continued)

*Primary Examiner* — Qiuwen Mi
(74) *Attorney, Agent, or Firm* — Nath, Goldberg & Meyer; Richard C. Litman

(57) ABSTRACT

The method of treating a bacterial infection using colostrum includes administering an effective amount of colostrum to a subject in need thereof. The infection can be caused by G+ or G− bacteria. The colostrum administered may be selected from the group consisting of bovine colostrum, camel colostrum, and a mixture of bovine colostrum and camel colostrum. The bacterial infection may be selected from the group consisting of *Staphylococcus aureus* subs. *aureus* Rosenbach, *Escherichia coli, Pseudomonas aeruginosa*, and Methicillin-resistant *Staphylococcus aureus*. A colostrum composition can include a mixture of bone and camel colostrum and a pharmaceutically acceptable carrier.

2 Claims, 24 Drawing Sheets

(56) References Cited

OTHER PUBLICATIONS

Karzai, W., et al., "Protection with Antibody to Tumor Necrosis Factor Differs with Similarly Lethal *Escherichia coli* Versus *Staphylococcus aureus* Pneumonia in Rats," Anesthesiology 99(1): pp. 81-89, 2003.

Kelso, A., "Heterogeneity in Lymphokine Profiles, of CD4+ and CD8+ T Cells and Clones Activated in Vivo and in Vitro," Immunol. Rev., 123: pp. 85-114, 1991.

Kingsley, S. M. K., and Bhat, B. V., "Differential Paradigms in Animal Models of Sepsis," Curr. Infect, Dis. Rep., 18(9): p. 26, 2016.

Nandi, A., et al., "Differential induction of inflammatory cytokines and reactive oxygen species in murine peritoneal macrophages and resident fresh bone marrow cells by acute *Staphylococcus aureus* infection: contribution of toll-like receptor 2 (TLR2)," Inflammation, 38(1): pp. 224-244, 2015.

Sacerdote, P., et al., "Biological Components in a Standardized Derivative of Bovine Colostrum," J. Dairy Sci., 96(3): pp. 1745-1754, 2013.

Schaible, U. E., and Kaufmann, S.H., "Iron and Microbial Infection," Nat. Rev. Microbiol. 2(12): 946-953, 2004.

Any identified foreign patents and/or publications were properly submitted in parent U.S. Appl. No. 16/809,882, filed Mar. 5, 2020, the priority of which is claimed.

METHOD OF TREATING A BACTERIAL INFECTION USING COLOSTRUM

CROSS REFERENCE TO RELATED APPLICATIONS

This application is a division of Ser. No. 16/809,882, filed Mar. 5, 2020, pending, the priority of which is claimed.

BACKGROUND

1. Field

The disclosure of the present patent application relates to a method of treating a bacterial infection by inducing an immune response.

2. Description of the Related Art

The CDC identifies antibiotic resistance as one of the most significant public health challenges of our time. In the United States alone, at least 2 million people are diagnosed with antibiotic-resistant infections annually, and at least 23,000 of these are fatal.

Strategies for developing new treatments have mostly focused on avoiding the rise of antibiotic resistance and on developing new antibiotics. However, avoiding the rise of antibiotic resistance is a failing rearguard action, given the prevalence of antibiotic-resistant bacterial strains. Further, the rate of new antibiotic development has slowed significantly. Most new classes of antibiotics were developed in the 1940s and the 1950s, with only two new classes developed since the year 2000. Antibiotics also have many undesirable side effects, ranging from nausea and diarrhea to liver and kidney damage.

Thus, a method of treating an infection solving the aforementioned problems is desired.

SUMMARY

A method of treating a bacterial infection using mixed colostrum can include administering a therapeutically effective amount of colostrum to a patient in need thereof. Administering colostrum to the patient can induce an immune response in the patient. In an embodiment, the colostrum administered may be selected from the group consisting of bovine colostrum, camel colostrum, and a mixture of bovine colostrum and camel colostrum. The infection can be bacterial. In an embodiment, the bacterial infection may be selected from the group consisting of G+ and G− bacteria: *Staphylococcus aureus* subs. *aureus* Rosenbach, *Escherichia coli, Pseudomonas aeruginosa*, and Methicillin-resistant *Staphylococcus aureus*.

An embodiment of the present subject matter is directed to a pharmaceutical composition including the mixture of bovine and camel colostrum and a pharmaceutically acceptable carrier.

An embodiment of the present subject matter is directed to a method of making a pharmaceutical composition including mixing the colostrum under sterile conditions with a pharmaceutically acceptable carrier and preservatives, buffers, or propellants to create the pharmaceutical composition; and providing the pharmaceutical composition in a form suitable for daily, weekly, or monthly administration. In an embodiment, the pharmaceutical composition may be natural and/or organic, comprising exclusively natural and/or organic ingredients An embodiment of the present subject matter is directed to a method of treating a bacterial infection, including administering to a subject in need thereof a therapeutically effective amount of a pharmaceutical composition according to the present subject matter. The pharmaceutical composition can include a mixture of bovine and camel colostrum. In an embodiment, the pharmaceutical composition may be an organic pharmaceutical composition.

These and other features of the present disclosure will become readily apparent upon further review of the following specification and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Similar reference characters denote corresponding features consistently throughout the attached drawings.

DETAILED DESCRIPTION OF THE PREFERRED EMBODIMENTS

Figure 1:
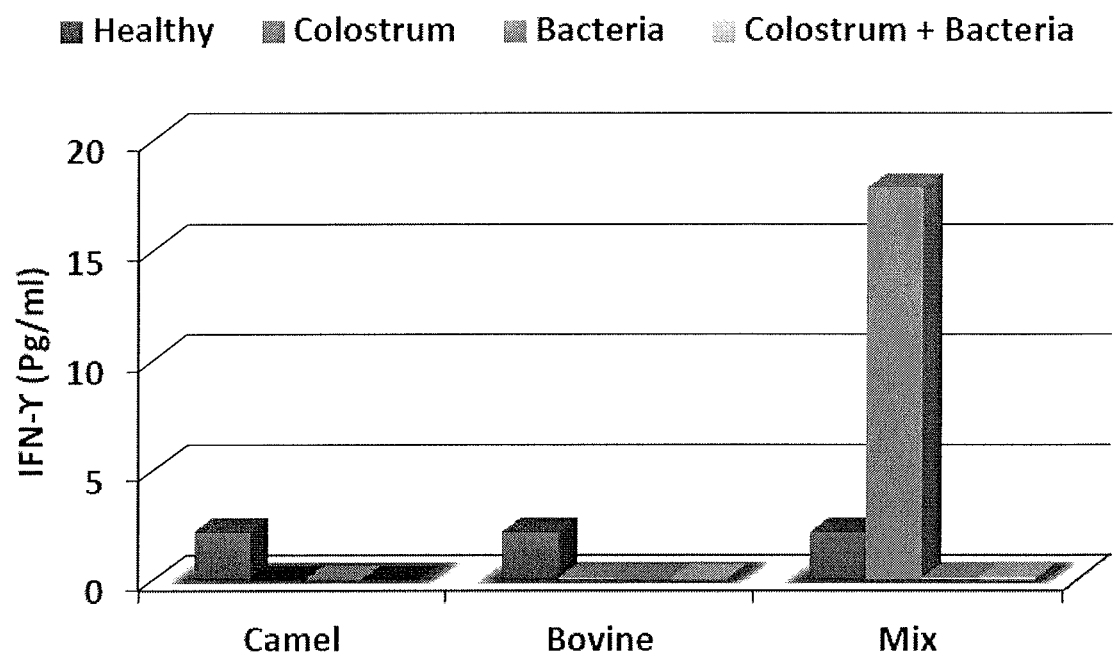
FIG. 1 depicts a bar graph displaying IFN-γ levels in control subjects, subjects exposed to colostrum alone, subjects exposed to *E. coli* alone, and subjects exposed to both *E. coli* and colostrum, where the colostrum was either bovine colostrum, camel colostrum, or a mixture of bovine and camel colostrum.

A method of treating a bacterial infection may include administering colostrum to a subject in need thereof. In an embodiment, the colostrum administered may be selected from the group consisting of bovine colostrum, camel colostrum, and a mixture of bovine colostrum and camel colostrum. In an embodiment, the infection is a bacterial infection or an infection caused by bacteria. The bacterial infection may be selected from the group consisting of G+ bacteria and G− bacteria. The bacterial infection may be selected from the group consisting of *Staphylococcus aureus* subs. *aureus* Rosenbach (*S. aureus*), *Escherichia coli* (*E. coli*), *Pseudomonas aeruginosa* (*P. aeruginosa*), and Methicillin-resistant *Staphylococcus aureus* (MRSA).

As used herein, a "subject" includes mammals, e.g., humans, dogs, cats, sheep, cows, rats, mice, and the like.

As used herein, the term "about," when used to modify a numerical value, means within ten percent of that numerical value.

As used herein, "colostrum" is the first form of milk produced by the mammary gland of a mammal just before and/or shortly after giving birth. Colostrum contains maternal antibodies intended to protect the newborn against disease, and frequently contains significantly more protein than non-colostrum milk.

In an embodiment, the colostrum may be collected after parturition and stored at −20° C. for at least a week. In an embodiment, the colostrum may then be thawed at −4° C. for at least 8 hours, and then lyophilized. In an embodiment, the lyophilized colostrum may then be suspended in sterilized saline solution at a concentration of 28 g lyophilized colostrum per liter of sterilized saline solution, forming a colostrum composition for use as discussed herein. In an embodiment, a colostrum composition may include bovine colostrum, camel colostrum, or a mixture of bovine colostrum and camel colostrum. An embodiment of the present subject matter may include the colostrum composition including at least a mixture of one of the bovine colostrum and the camel colostrum and a pharmaceutically acceptable carrier.

In an embodiment, the administration of colostrum or a colostrum composition of the present subject matter may include daily administration. In an embodiment, the daily administration may be administered in the early morning hours. In an embodiment, administration of colostrum or a colostrum composition of the present subject matter may include injecting one ml of a solution of 28 g lyophilized colostrum per liter of sterilized saline solution every day at eight in the morning for at least a month.

In an embodiment, administration of the colostrum or colostrum composition as described herein may prevent the lethal effect of a lethal dose of an infectious bacterium. In an embodiment, the infectious bacterium may be selected from the group consisting of *E. coli, P. aeruginosa, S. aureus*, and MRSA.

In an embodiment, administration of the colostrum or colostrum composition of the present subject matter may stimulate the immune system. In an embodiment, the immune system stimulation may include an increase in the level of one or more cytokines in the blood. In an embodiment, the cytokines may be selected from the group consisting of Interferon-7 (IFN-γ), Tumor Necrosis Factor α (TNF-α), and Interleukin-10 (IL-10).

An embodiment of the present subject matter is directed to a pharmaceutical composition comprising the mixture of bovine and camel colostrum and a pharmaceutically acceptable carrier.

An embodiment of the present subject matter is directed to a method of making a pharmaceutical composition, including mixing an effective amount of the bovine and camel mixture colostrum with a pharmaceutically acceptable carrier. For example, the method of making a pharmaceutical composition can include mixing the colostrum under sterile conditions with a pharmaceutically acceptable carrier, preservatives, buffers, and/or propellants to create the pharmaceutical composition. In an embodiment, the pharmaceutical composition may be natural and/or organic and the pharmaceutically acceptable carrier may also be natural and/organic.

To prepare the pharmaceutical composition, at least one of the bovine colostrum and camel colostrum, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the colostrum compositions or an amount effective to treat a disease, such as a bacterial infection, may be determined initially from the Examples described herein and adjusted for specific targeted diseases using routine methods.

The colostrum or colostrum compositions can be administered to a subject in need thereof. For example, the colostrum or colostrum compositions can be used to treat a subject suffering from a bacterial infection. The bacterial infection can be caused by *E. coli, P. aeruginosa, S. aureus*, MRSA, or the like.

An embodiment of the present subject matter is directed to a method of treating a bacterial infection, comprising administering to a subject in need thereof a therapeutically effective amount of the pharmaceutical composition according to the present subject matter. In an embodiment, the pharmaceutical composition may be organic.

The colostrum or pharmaceutical compositions thereof can be administered to a subject by any suitable route. For example, the colostrum or pharmaceutical compositions can be administered orally (including buccally and sublingually), nasally, rectally, intracisternally, intra-vaginally, intraperitoneally, topically, transdermally (as by powders, ointments, or drops), and/or parenterally. As used herein, "parenteral" administration refers to modes of administration other than through the gastrointestinal tract, which includes intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The following examples illustrate the present teachings.

Example 1

Determining the Lethal Dose and Optimum Route of Infection for Four Gram-Positive and Gram-Negative Bacteria in a Rat Model The ethical committee of King Saud University provided prior approval before any animal studies were commenced. All animals were fed with standard laboratory rat chow (Basal diet 5755, PMI Nutrition International, Inc., Richmond, Calif., USA) according to the National Institute of Health guidelines. Rats were quarantined for six days before commencing experiments. Chemical restraint anesthesia was achieved using injectable sedation, such as a Ketamine/Xylazine mix administered subcutaneously.

The Riyadh Military Hospital Bacteriology Laboratory provided American Type Culture Collection (ATCC) *Escherichia coli* (*E. coli*) (ATTC 25922). The bacterium is Enteropathogenic *E. coli* (EPEC) but not Enterotoxigenic *E. coli* (ETEC). It does not produce verotoxin and is used for media testing and as a negative control for LT toxin production. This organism is a CLSI control strain for antimicrobial susceptibility testing. Other bacterial strains obtained from the same source include *Staphylococcus aureus* subsp. *aureus* Rosenbach (*S. aureus*) (ATCC 29213), Methicillin-resistant *Staphylococcus aureus* (MRSA) (ATCC 12498), *Pseudomonas aeruginosa* (*P. aeruginosa*) (ATCC 27853).

Bacterial propagation was performed in Trypticase Soy Broth (TSB) for seven hours at 26° C., and stock aliquots were frozen at −79° C. until used. A frozen stock sample was thawed and plated onto Trypticase Soy Blood Agar plates in preparation for a bacterial inoculum lethal dose trial using rats injected subcutaneously and intravenously. The results of this trial are compiled in Table 1 and Table 2 below.

Virus and antibody-free male Wistar rats were acquired from the Pharmacy College of King Saud University. Animals were housed up to 6 animals in a cage. Male Wistar rats (n=118) weighing 190-300 g were randomly selected to receive either intravenous (i.v.) or intraperitoneal (i.p.) injection with either *E. coli* or one of the other three studied bacteria (n=20-40 per group). Control rats were kept in a separate compartment. Animals were observed after bacterial injection to record the number of dead animals. The results are summarized in Table 1. At six hours after bacterial administration through either injection route, animals appeared weak and lethargic. Estimated lethal doses of each pathogenic microbe were determined as shown in Table 2. In summary, the optimized lethal doses were determined to be ~6×10$^8$/ml Colony Forming Units (CFU) for *E. coli*, 9×10$^8$/0.5 ml CFU *S. aureus*, ~9.5×10$^8$/0.5 ml CFU *P. aeruginosa*, and 12×10$^8$/1.5 ml CFU MRSA. The i.v. route of administration was preferred for all microbes.

TABLE 1

Lethal Dose in Rats Demonstration for Studied Groups Over One Week

| Bacterial strains | Concentration per ml | Injection Site | No. Deaths in 1 week |
|---|---|---|---|
| *Escherichia coli* ATTC 25922 | 10$^8$/0.5 ml | i.p. (3) | One-4 days |
| | 10$^8$/1 ml (3 rats) | i.p.(3) i.v.(3) | Zero |
| | 10$^8$/2 ml (3 rats) | | |
| | 10$^8$/3 ml (6 rats) | i.p.(3) i.v.(3) | One (i.v.)-7 days |
| | 10$^{16}$/0.1 ml (2 rats) | i.p.(3) | Zero |
| | 10$^{16}$/0.5 ml (1 rat) | | |
| | 10$^{16}$/1 ml (1 rat) | i.p.(2) | Two-2 days |
| | 10$^{16}$/1.5 ml (1 rat) | | |
| | 10$^{18}$/1 ml (6 rats) | i.p.(3) i.v.(3) | Zero |
| | 10$^{36}$/1 ml (6 rats) | i.v.(3 + 3) | Three-1 day |
| *Pseudomonas aeruginosa* ATCC27853 | 10$^8$/0.5 ml (3 rats) | i.p.(3) | Zero |
| | 10$^8$/1 ml (2 rats) | i.p.(2) i.v.(2) | One (i.v., 10$^8$/2 ml) 1 day |
| | 10$^8$/2 ml (2 rats) | | |
| | 10$^8$/3 ml (2 rats)t | i.p.(1) i.v.(1) | Zero |
| | 10$^{40}$/0.1 ml (2 rats) | i.p.(3) | One (10$^{40}$/0.5 ml) 3 days |
| | 10$^{40}$/0.5 ml (rat) | | |
| | 10$^{40}$/1 ml (1 rat) | i.p.(2) | Zero |
| | 10$^{40}$/1.5 ml (1 rat) | | |
| | 10$^{40}$/0.5 ml (6 rats) | i.p.(3 + 3) | Three (i.v., 10$^{72}$) 3 days |
| | 10$^{72}$/0.5 ml (6 rats) | i.v.(3 + 3) | |
| *Staphylococcus aureus* ATCC12498 | 10$^8$/0.5 ml (3 rats) | i.p.(3) | One-4 days |
| | 10$^8$/1 ml (2 rats) | i.p.(2) i.v.(2) | Zero |
| | 10$^8$/2 ml (2 rats) | | |
| | 10$^8$/3 ml (2 rats) | i.p.(1) i.v.(1) | Zero |
| | 10$^{20}$/0.1 ml (2 rats) | i.p.(3) | Zero |
| | 10$^{20}$/0.5 ml (1 rat) | | |
| | 10$^{20}$/1 ml (1 rat) | i.p.(2) | Zero |
| | 10$^{20}$/1.5 ml (1 rat) | | |
| | 10$^{40}$/0.5 ml (3 rats) | i.v.(3 + 3) | Three (i.v., 10$^{64}$/0.5 ml) 2 days |
| | 10$^{64}$/0.5 ml (3 rats) | | |
| Methicillin-resistant *Staphylococcus aureus* ATCC12498 | 10$^8$/0.5 ml (3 rats) | i.p.(3) | Zero |
| | 10$^8$/1 ml (2 rats) | i.p.(2) i.v.(.2) | Zero |
| | 10$^8$/2 ml (2 rats) | | |
| | 10$^8$/3 ml (2 rats) | i.p.(1) i.v.(1) | Zero |
| | 410$^{20}$/0.1 ml (2 rats) | i.p.(3) | Zero |
| | 10$^{20}$/0.5 ml (1 rat) | | |
| | 10$^{20}$/1 ml (1 rat) | i.p.(2) | Zero |
| | 10$^{20}$/1.5 ml (1 rat) | | |
| | 10$^{40}$/0.5 ml (6 rats) | i.p.(3 + 3) | Zero |
| | 10$^{64}$/0.5 ml (6 rats) | i.v.(3 + 3) | |
| | 10$^{60}$/1 ml (3 rats) | i.v.(3 + 3) | Zero |
| | 10$^{72}$/1 ml (3 rats) | | |
| | 10$^{90}$/1 ml (2 rats) | i.p.(3) | Seven-6 days |
| | 10$^{90}$/1.5 ml (1 rat) | i.p.(2) | |
| | 10$^{120}$/1 ml (2 rats) | i.v.(2) | |
| | 10$^{120}$/1.5 ml (2 rats) | | |

TABLE 2

Recommended Lethal Dose for Studied Bacteria

| Bacterial strains | Concentration per ml | Injection Site | No. Deaths in 1 Week |
|---|---|---|---|
| *Escherichia coli* ATTC 25922 | ~6 × 10$^8$/1 ml CFU/ml | i.v. (3 rats) | Three-1 day |
| *Pseudomonas aeruginosa* ATCC27853 | ~9.5 × 10$^8$/0.5 ml CFU/ml | i.v. (3 rats) | Three-3 days |
| *Staphylococcus aureus* ATCC12498 | 9 × 10$^8$/0.5 ml CFU/ml | i.v. (3 rats) | Three-2 days |

TABLE 2-continued

Recommended Lethal Dose for Studied Bacteria

| Bacterial strains | Concentration per ml | Injection Site | No. Deaths in 1 Week |
|---|---|---|---|
| Methicillin-resistant *Staphylococcus aureus* ATCC12498 | $12 \times 10^8$/1.5 ml CFU/ml | i.v. (3 rats) | Three-6 days |

Example 2

Determining Effect of Camel Colostrum, Bovine Colostrum, and a Mixture of Camel Colostrum and Bovine Colostrum on Survival of Rats Infected with Gram-Positive and Gram-Negative Bacteria Three types of colostrum were used from different sources. Camel colostrum was sourced from 10 healthy individual camels (*Camelus dromedarius*) that were chosen randomly (average age, six years) from the Conservation and Genetic Improvement Center in Al-karj, Saudi Arabia. Samples were obtained manually from all camels' udders and were collected immediately after parturition.

Bovine colostrum samples were sourced from 10 healthy Holstein cows (average age, 3.8 years) provided by the Almarai Company. The Immunology Lab, King Khaled Hospital, Medicine College, King Saud University Hospital, collected the samples and confirmed that the source cows were in good health and had no clinical evidence of mastitis or tuberculosis, delivered healthy full-term infants, and had not consumed medications within one week before collection.

The colostrum samples were collected using the following protocol: 20 samples collected at the first-day parturition after thorough hand washing and cleansing of the breast and nipple with soap and tap water. Milk samples were expressed manually into sterile Erlenmeyer flasks, pooled, dispensed into sterile test tubes and stored on at −20° C.

The study included a control group with no graft contamination and no antibiotic prophylaxis (Group 1), a bacterial treatment group (Group 2), a colostrum treatment group (Group 3), and a bacterial treatment and colostrum treatment group (Group 4). (See Table 3) Group 3 included three different sub-groups, designated camel colostrum, bovine colostrum, and mix colostrum. One ml of prepared colostrum solution (28 g lyophilized colostrum/liter sterilized saline solution (w/v)) was administered by intraperitoneal injection every day early in the morning for 30 days.

The rats of Group 2 and Group 4 were then anesthetized with chloroform or ether and injected intravenously with the recommended lethal dose of one of the studied bacteria in the tail vein. Survival rates in each group were observed for two weeks after injection.

TABLE 3

The Study Groups

| | |
|---|---|
| Group 1 | Control group: Sterilized saline was administered every day at eight AM for 30 days |
| Group 2 | Bacterial groups: four bacterial sub-groups were designated, one for each bacterium: *Escherichia coli* ATTC 25922 *Pseudomonas aeruginousa* ATCC27853 *Staphylococcus aureus* ATCC12498 Methicillin-resistant *Staphylococcus aureus* ATCC12498 The lethal dose of each bacterium established in Table 1 was administered intravenously once in the tail vein of each rat using a 14-gauge needle at eight AM on the starting day. |
| Group 3 | Colostrum groups: Three colostrum sub-groups were designated: Camel Colostrum Bovine Colostrum Mix Colostrum One ml of prepared colostrum solution (28 g lyophilized colostrum/liter sterilized saline solution (w/v)) was injected i.p. daily at eight AM for 30 days. |
| Group 4 | Bacterial and Colostrum groups: Sub-groups were designated for all possible combinations of Group 2 and Group 3. |

At zero time up to one month and after inoculation with the four studied bacteria and induction by colostrum as in Table 4 and Table 5, animals appeared weak and lethargic with the microbial treatments. In controls without bacterial treatment, camel colostrum, bovine colostrum, and mix (a mixture of both camel and bovine colostrum) produced a similar survival rate without evidence of concentration of disease (See Table 4). Compared with the control treatment, bacterial treatment with colostrum improved mortality rates associated with the bacterial variable and route of treatment. These animals lived through one month of observation. The death of animals started from the second day until the 22$^{nd}$ day, with most deaths occurring in the administrated pathogenic bacteria only group (Group 2). As shown in Table 4, the fastest and the best-protected treatment was lethal *S. aureus* with 50-100% mortality.

Moreover, 100% of rats injected with *S. aureus* and vaccinated i.p. by one of the three types of colostrum survived. Camel colostrum had a tremendous protective effect from lethal MRSA, converting 100% mortality to 100% survival. Camel and bovine colostrum enhanced survival against lethal *P. aeruginosa* from 0% to 33% survival in the former and from 50% to 66% survival in the latter (see Table 4). Lethal *E. coli* caused 84% mortality, and camel colostrum enhanced survival of up to 83%. On the other hand, mixed colostrum also enhanced survival, up to 50%.

TABLE 4

Morbidity and Mortality (Survival %) in Lethal Dose Induction for Four Pathogenic Bacteria using Three Colostrum Groups as Anti-Microbial Agents

| Dose (~CFU/ml) | Rats per Group | Healthy Rats | Colostrum Healthy Rats | | | Bacteria Healthy or Dead(Day) Rats | | | Bacteria & Colostrum Healthy or Dead(Day) Rats | | |
|---|---|---|---|---|---|---|---|---|---|---|---|
| | | | Camel | Bovine | Mix | Camel | Bovine | Mix | Camel | Bovine | Mix |
| *E. coli*: $6 \times 10^8$/ml | 6 | 6 | 6 | 6 | 6 | 6 | 2(3) 2(7) 1(13) | 6 | 1(2) | 1(2) 2(9) 3(16) | 3(22) |

TABLE 4-continued

Morbidity and Mortality (Survival %) in Lethal Dose Induction for Four Pathogenic
Bacteria using Three Colostrum Groups as Anti-Microbial Agents

| Dose | Rats per Group | Healthy Rats | Colostrum Healthy Rats | | | Bacteria Healthy or Dead(Day) Rats | | | Bacteria & Colostrum Healthy or Dead(Day) Rats | | |
|---|---|---|---|---|---|---|---|---|---|---|---|
| (~CFU/ml) | | | Camel | Bovine | Mix | Camel | Bovine | Mix | Camel | Bovine | Mix |
| % Survival | 100 | 100 | 100 | 100 | 100 | 100 | 16 | 100 | 83 | 0 | 50 |
| P. aeruginosa: | 6 | 6 | 6 | 6 | 6 | 2(2) | 1(2) | 6 | 2(5) | 2(20) | 6 |
| $9.5 \times 10^8/0.5$ ml | | | | | | 3(3) | 1(8) | | 1(9) | | |
| | | | | | | 1(7) | 1(15) | | 1(11) | | |
| % Survival | 100 | 100 | 100 | 100 | 100 | 0 | 50 | 100 | 33 | 66 | 100 |
| S. aureus | 6 | 6 | 6 | 6 | 6 | 1(3) | 2(4) | 1(3) | 6 | 6 | 6 |
| $9 \times 10^8/0.5$ ml | | | | | | 1(5) | 1(7) | 1(4) | | | |
| | | | | | | 1(17) | 1(10) | 1(12) | | | |
| | | | | | | | 1(11) | | | | |
| % Survival | 100 | 100 | 100 | 100 | 100 | 50 | 0 | 50 | 100 | 100 | 100 |
| MRSA: | 6 | 6 | 6 | 6 | 6 | 2(2) | 6 | 6 | 6 | 6 | 6 |
| $12 \times 10^8/1.5$ ml | | | | | | 1(4) | | | | | |
| | | | | | | 1(8) | | | | | |
| | | | | | | 1(12) | | | | | |
| | | | | | | 1(16) | | | | | |
| % Survival | 100 | 100 | 100 | 100 | 100 | 0 | 100 | 100 | 100 | 100 | 100 |

Example 3

Determining Effect of Camel Colostrum, Bovine Colostrum, and a Mixture of Camel Colostrum and Bovine Colostrum on Percentage Change in Weight of Rats Infected with Gram-Positive and Gram-Negative Bacteria The effect of the treatment on the percentage change of the weight of rats (grams) for each studied pathogenic bacterium was determined using three types of colostrum; Camel, Bovine, and Mix. The results of this experiment are illustrated in Table 5 and Table 6. The range of percent change in the weight of healthy rats was revealed in minimum and maximum (Min 10%-Max 29%) through one month of observation. Camel colostrum and Mix colostrum induced a remarkable 6%-59% increase in the weight of rats. Bacterial injections dramatically decreased the percent weight change in rats from −12% to 12%. The most notable max increase values in percent change of weight of rats after colostrum treatment were observed when comparing the weight of rats infected with MRSA alone with the weight of the rats treated with mix colostrum. Mix colostrum induced 43% change in the weight of rats compared to −21% weight change in rats injected with a lethal dose of MRSA alone.

TABLE 5

Treatment Effects on Average % Change in Weight
(g) of Rats (Healthy & Bacteria Treatment Groups)

| | Group | | | | | | | | | |
|---|---|---|---|---|---|---|---|---|---|---|
| | Healthy | | | | | Bacteria | | | | |
| Day | 1 | 10 | 20 | 30 | Avg % | 1 | 10 | 20 | 30 | Avg % |
| | Camel Colostrum | | | | | | | | | |
| E. coli | 226 | 256 | 276 | 292 | 29% | 210 | 205 | 209 | 214 | 1.9 |
| P. aeruginosa | 236 | 215 | 250 | 287 | 21% | 228 | 232 | 230 | 245 | 7.4 |
| S. aureus | 227 | 205 | 228 | 250 | 10% | 230 | 239 | 243 | 235 | 2.1 |
| MRSA | 235 | 225 | 247 | 290 | 23% | 207 | 210 | 222 | 205 | −0.9 |
| | Bovine Colostrum | | | | | | | | | |
| E. coli | 226 | 256 | 276 | 292 | 29% | 215 | 224 | 230 | 235 | 9.3 |
| P. aeruginosa | 236 | 215 | 250 | 287 | 21% | 234 | 230 | 227 | 220 | −5.9 |
| S. aureus | 251 | 205 | 228 | 250 | 10% | 215 | 224 | 230 | 235 | 9.3 |
| MRSA | 235 | 225 | 247 | 290 | 23% | 234 | 230 | 227 | 220 | −5.9 |
| | Mix Colostrum | | | | | | | | | |
| E. coli | 226 | 256 | 276 | 292 | 29% | 242 | 250 | 267 | 259 | 7 |
| P. aeruginosa | 236 | 215 | 250 | 287 | 21% | 247 | 255 | 247 | 279 | 12 |
| S. aureus | 251 | 205 | 228 | 250 | 10% | 273 | 249 | 231 | 213 | −21 |
| MRSA | 235 | 225 | 247 | 290 | 23% | 252 | 270 | 263 | 267 | 5.9 |

TABLE 6

Treatment Effects on Average % Change in Weight (g) of Rats
(Bacteria & Colostrum and Colostrum Treatment Groups)

| | Group | | | | | | | | | |
|---|---|---|---|---|---|---|---|---|---|---|
| | Bacteria & Colostrum | | | | | Colostrum | | | | |
| Day | 1 | 10 | 20 | 30 | Avg % | 1 | 10 | 20 | 30 | Avg % |
| Camel Colostrum | | | | | | | | | | |
| E. coli | 227 | 235 | 245 | 240 | 5.7% | 213 | 246 | 278 | 286 | 34 |
| P. aeruginosa | 260 | 252 | 254 | 259 | −0.3% | 227 | 239 | 345 | 354 | 55 |
| S. aureus | 234 | 239 | 244 | 260 | 11% | 243 | 275 | 288 | 295 | 21 |
| MRSA | 250 | 253 | 255 | 259 | 3.6% | 252 | 258 | 261 | 269 | 6 |
| Bovine Colostrum | | | | | | | | | | |
| E. coli | 236 | 264 | 285 | 298 | 26% | 230 | 236 | 254 | 270 | 17 |
| P. aeruginosa | 241 | 265 | 273 | 295 | 37% | 242 | 265 | 277 | 293 | 21 |
| S. aureus | 236 | 264 | 285 | 298 | 26% | 230 | 236 | 254 | 270 | 17 |
| MRSA | 241 | 265 | 273 | 295 | 22.4 | 218 | 244 | 279 | 298 | 36 |
| Mix Colostrum | | | | | | | | | | |
| E. coli | 270 | 284 | 312 | 326 | 20% | 205 | 240 | 276 | 288 | 40 |
| P. aeruginosa | 234 | 255 | 288 | 310 | 32% | 272 | 281 | 301 | 321 | 18 |
| S. aureus | 230 | 252 | 284 | 329 | 43% | 209 | 225 | 246 | 280 | 33 |
| MRSA | 202 | 235 | 272 | 280 | 38% | 193 | 225 | 286 | 307 | 59 |

Example 4

Effect of Infection and/or Colostrum on Expression of Three Cytokines in Rats

For circulating blood analysis, animals were anesthetized with an ether mask. Circulating levels of IFN-γ, IL-10, and TNF-α were measured in serum samples of all rats obtained from the eye vein. Blood samples were collected in heparinized syringes to asses cytokine level assessed of IFN-γ, IL10, and TNF-α. Serum concentrations of each cytokine were monitored at 0 days post-treatment, 24 hours post-treatment, 7-25 days post-treatment (midpoint or Mid), and 30 days post-treatment (Last or Final) by ELISA. Briefly, blood samples (2 ml) were centrifuged for 10 minutes at 3500 rpm, at 4° C., and the serum samples were kept at −20° C. in a freezer until examined. Commercial reagents used to identify individual cytokines included Quantikine®ELISA, Rat TNF-α Immunoassay, Catalog Number RTA00, Quantikine®ELISA, Rat IL-10 Immunoassay, Quantikine®ELISA, and Rat IFN-γ Immunoassay. These kits were used according to the manufacturer's recommendations (USA & Canada R&D Systems, Inc. Minneapolis). The limits of sensitivity of the assay were determined to be five pg/ml for TNF-α and ten pg per ml for IFN-γ and IL-10, respectively. The intra- and inter-assay coefficients of deviation were less than 5% and 10%, respectively.

Quantitative data were statistically represented in terms of minimum, maximum, and median. A comparison between different groups in the present study was done using the Kruskal-Wallis test to compare between more than two nonparametric groups.

Correlation between various variables was determined using Spearman rank correlation coefficient (R) with graph representations using linear regression.

A probability value (p-value) less than or equal to 0.05 was considered significant. All statistical analyses were performed using statistical software SPSS (Statistical Package for Social Science) statistical program version 16.0. Graphs were created using SPSS statistical program version 16.0 with Microsoft Excel program version 2010.

Initial results for IFN-γ expression as a measure of the immune response in the presence of colostrum, E. coli, or E. coli and colostrum are presented in Table 7 and FIG. 1.

TABLE 7

E. Coli and IFN-γ Immune Response in the Presence
of Colostrum (Expressed as Median pg/ml (Min-Max))

| Colostrum Type | Camel Colostrum | Bovine Colostrum | Mix Colostrum | P value[A] |
|---|---|---|---|---|
| Healthy Control | 2.20 (0.00-43.91) | 2.20 (0.00-43.91) | 2.20 (0.00-43.91) | 1.000 |
| Colostrum | 0.00 (0.00-0.03) | 0.09 (0.00-209.50) | 17.82 (0.00-125.00) | 0.055 |
| Bacteria | 0.02 (0.00-0.07) | 0.06 (0.01-74.24) | 0.11 (0.00-125.00) | 0.219 |
| Colostrum & Bacteria | 0.01 (0.00-0.03) | 0.06 (0.00-117.10) | 0.12 (0.00-93.75) | 0.098 |
| P value[B] | 0.018 | 0.808 | 0.901 | |

[A]=Comparison between different treatments within a single colostrum type using a nonparametric test (Kruskal-Wallis Test).
[B]=Comparison between different colostrum types in each treatment using a nonparametric test (Kruskal-Wallis Test).

Figure 2A:
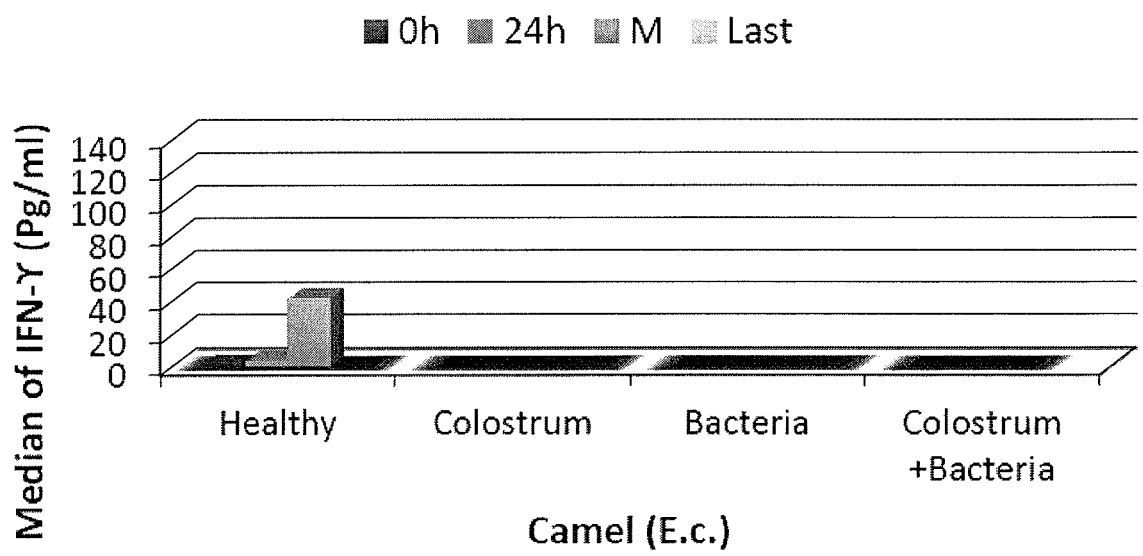
FIG. 2A depicts a bar graph displaying IFN-γ levels over time in control subjects, subjects exposed to colostrum alone, subjects exposed to *E. coli* alone, and subjects exposed to both *E. coli* and colostrum, where the colostrum was camel colostrum.
Figure 2B:
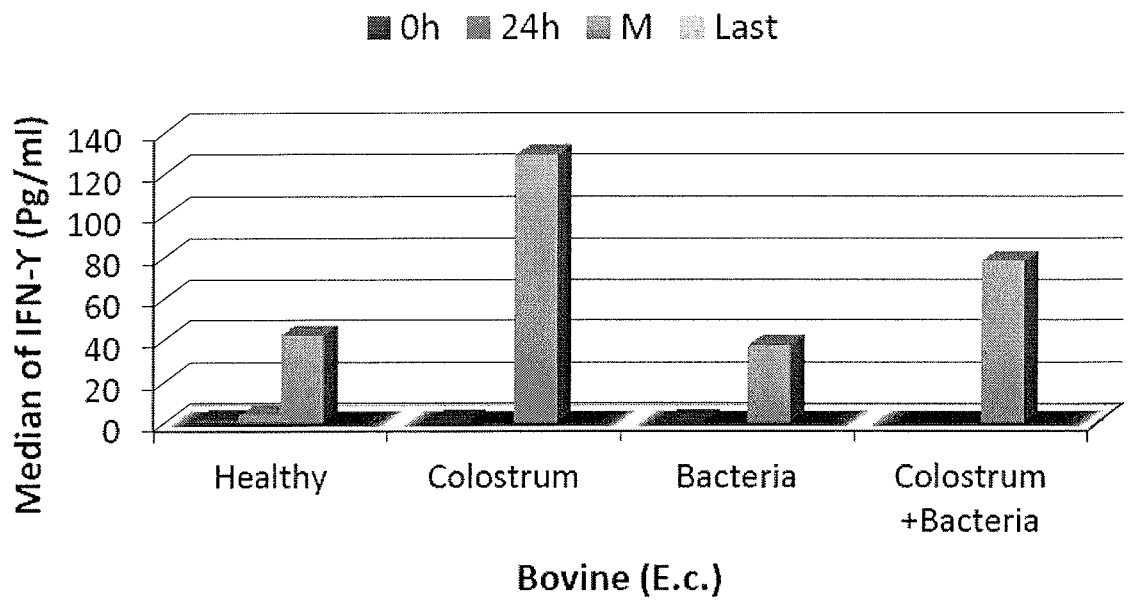
FIG. 2B depicts a bar graph displaying IFN-γ levels over time in control subjects, subjects exposed to colostrum alone, subjects exposed to *E. coli* alone, and subjects exposed to both *E. coli* and colostrum, where the colostrum was bovine colostrum.
Figure 2C:
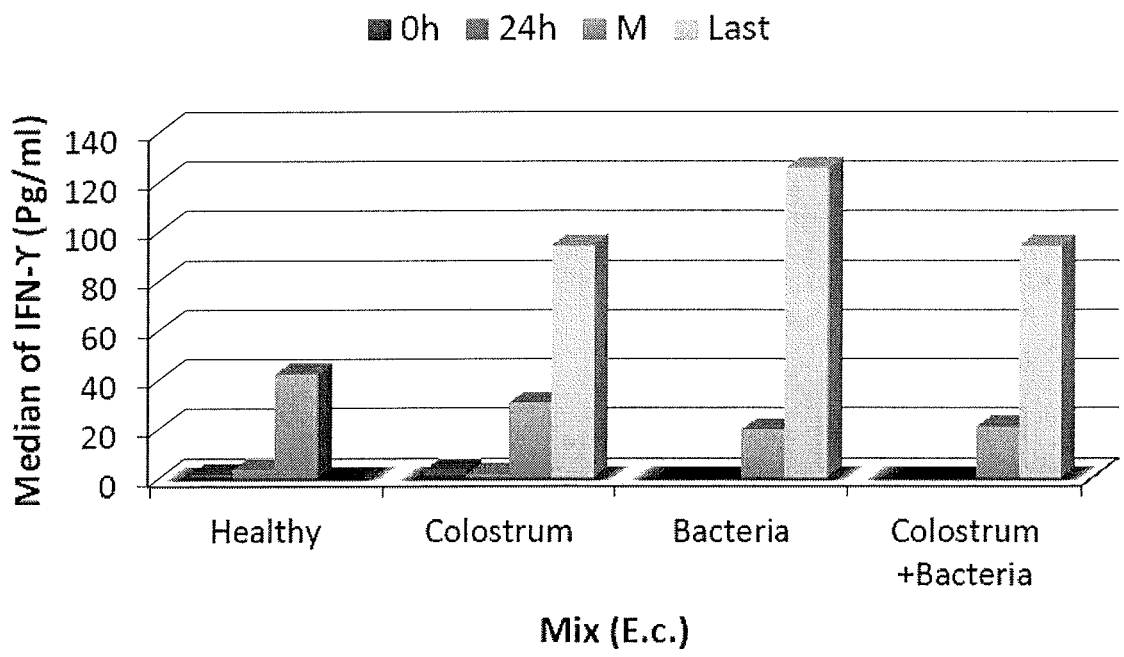
FIG. 2C depicts a bar graph displaying IFN-γ levels over time in control subjects, subjects exposed to colostrum alone, subjects exposed to *E. coli* alone, and subjects exposed to both *E. coli* and colostrum, where the colostrum was a mixture of camel colostrum and bovine colostrum.

Data from the full month-long experiment are presented in Table 8 and FIGS. 2A-2C. In the model of E. coli bacterial infection treated with either bovine colostrum or with the mixed colostrum, IFN-γ elevated up to 0.12 pg/ml in the mixed colostrum treatment group but was 0.06 pg/ml in the bovine colostrum treatment group. At the end of the trial (Last) IFN-γ exhibited a steady level of the immune response in the mixed colostrum treatment group (93.750 pg/ml) as well as the bacterial infection and mixed colostrum treatment group. (See Table 8). This experiment confirms the synergistic effect of mixed colostrum, as it triggers a more significant immune response than bovine colostrum or camel colostrum alone.

TABLE 8

E. coli and IFN-γ Immune Response in the Presence of Colostrum at 0 h, 24 h, 7-25 days (M), and 30 days (Last) (Expressed as Median (Min-Max)

| Treatment Group | Time | Camel | Bovine | Mix |
|---|---|---|---|---|
| Healthy | 0 h | 1.496 | 1.496 | 1.496 |
| | | (0.220-2.770) | (0.220-2.770) | (0.220-2.770) |
| | 24 h | 3.587 | 3.587 | 3.587 |
| | | (1.630-5.550) | (1.630-5.550) | (1.630-5.550) |
| | M | 42.175 | 42.175 | 42.175 |
| | | (40.440-43.910) | (40.440-43.910) | (40.440-43.910) |
| | Last | 0.005 | 0.005 | 0.005 |
| | | (0.000-0.010) | (0.000-0.010) | (0.000-0.010) |
| P value | | 0.104 | 0.104 | 0.104 |
| Colostrum | 0 h | 0.019 | 1.055 | 3.129 |
| | | (0.010-0.030) | (0.120-1.990) | (0.000-6.260) |
| | 24 h | 0.002 | 0.058 | 1.667 |
| | | (0.000-0.000) | (0.060-0.060) | (0.000-3.330) |
| | M | 0.002 | 128.800 | 30.327 |
| | | (0.000-0.000) | (48.10-209.50) | (29.390-31.260) |
| | Last | 0.005 | 0.001 | 93.750 |
| | | (0.000-0.010) | (0.000-0.000) | (62.50-125.00) |
| P value | | 0.160 | 0.078 | 0.106 |
| Bacteria | 0 h | 0.025 | 1.019 | 0.003 |
| | | (0.010-0.040) | (0.050-1.990) | (0.000-0.000) |
| | 24 h | 0.003 | 0.051 | 0.003 |
| | | (0.000-0.010) | (0.040-0.070) | (0.000-0.000) |
| | M | 0.016 | 37.183 | 19.633 |
| | | (0.000-0.030) | (0.130-74.240) | (0.200-39.060) |
| | Last | 0.049 | 0.013 | 125.00 |
| | | (0.020-0.070) | (0.010-0.020) | (125.00-125.00) |
| P value | | 0.280 | 0.139 | 0.103 |
| Colostrum & Bacteria | 0 h | 0.018 | 0.048 | 0.061 |
| | | (0.010-0.030) | (0.020-0.070) | (0.000-0.120) |
| | 24 h | 0.001 | 0.067 | 0.008 |
| | | (0.000-0.000) | (0.040-0.090) | (0.010-0.010) |
| | M | 0.016 | 77.905 | 20.840 |
| | | (0.000-0.030) | (38.71-117.10) | (20.840-20.840) |
| | Last | 0.000 | 0.012 | 93.750 |
| | | (0.000-0.000) | (0.000-0.020) | (93.750-93.750) |
| P value | | 0.165 | 0.104 | 0.362 |

Figure 3:
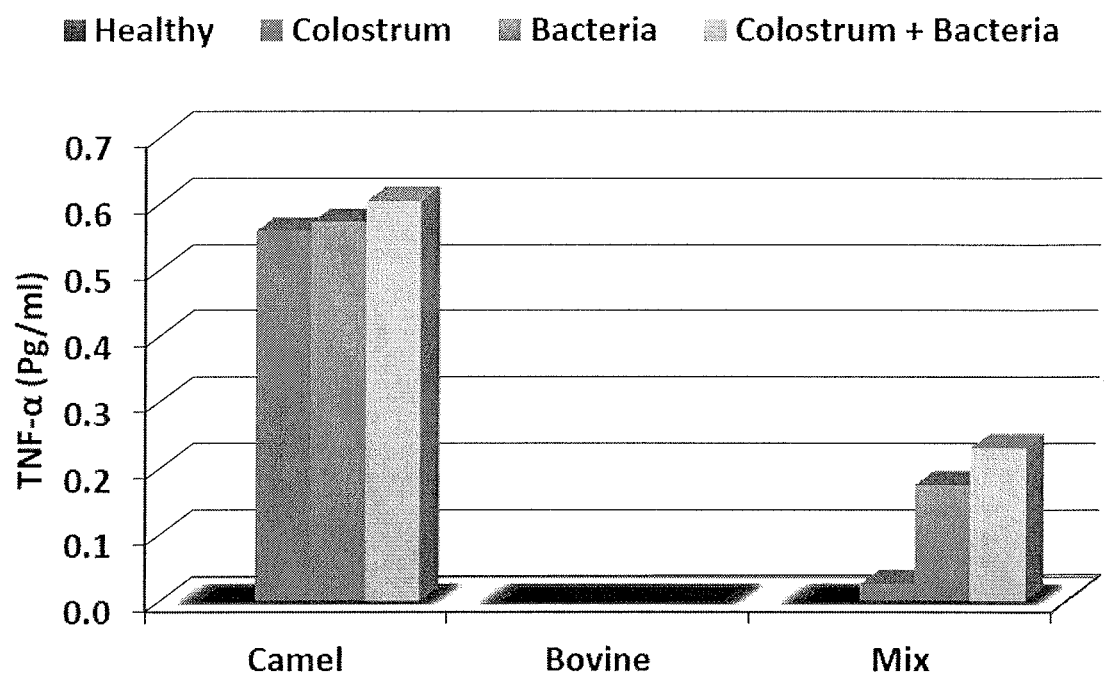
FIG. 3 depicts a bar graph displaying TNF-α levels over time in control subjects, subjects exposed to colostrum alone, subjects exposed to *E. coli* alone, and subjects exposed to both *E. coli* and colostrum, where the colostrum was bovine, camel, or a mixture of bovine colostrum and camel colostrum.
Figure 4A:
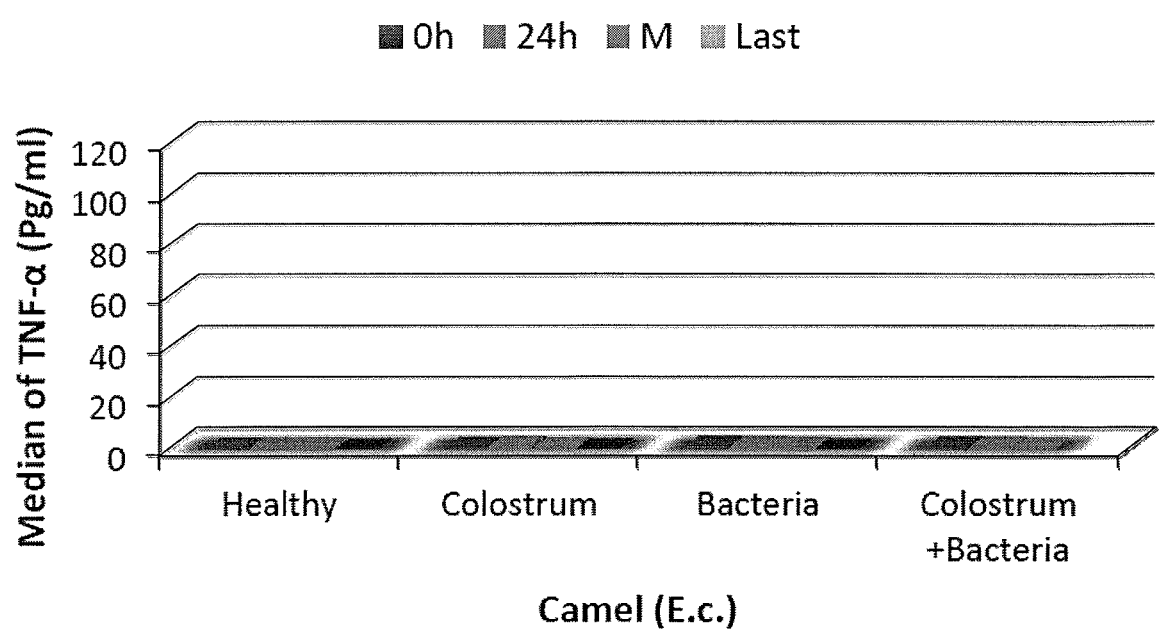
FIG. 4A depicts a bar graph displaying TNF-α levels over time in control subjects, subjects exposed to colostrum alone, subjects exposed to *E. coli* alone, and subjects exposed to both *E. coli* and colostrum, where the colostrum was camel colostrum.
Figure 4B:
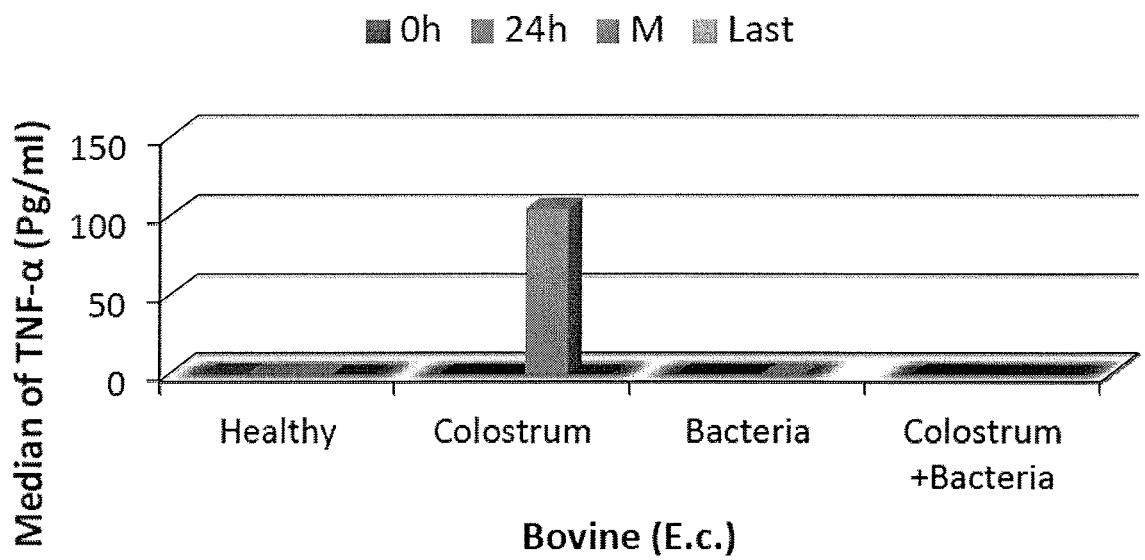
FIG. 4B depicts a bar graph displaying TNF-α levels over time in control subjects, subjects exposed to colostrum alone, subjects exposed to *E. coli* alone, and subjects exposed to both *E. coli* and colostrum, where the colostrum was bovine colostrum.
Figure 4C:
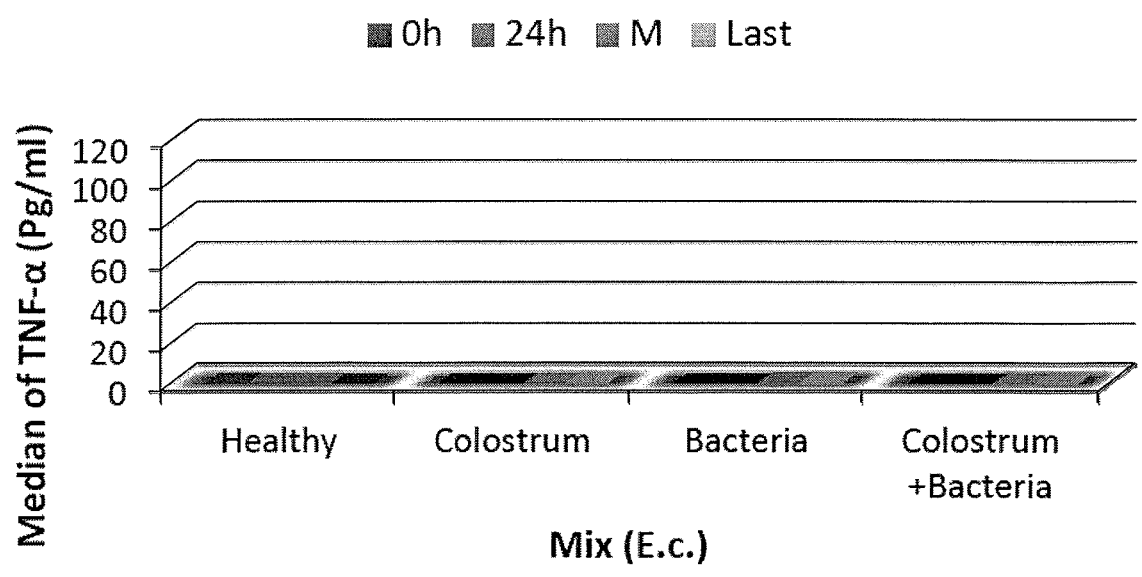
FIG. 4C depicts a bar graph displaying TNF-α levels over time in control subjects, subjects exposed to colostrum alone, subjects exposed to *E. coli* alone, and subjects exposed to both *E. coli* and colostrum, where the colostrum was a mixture of camel colostrum and bovine colostrum.

In the model of E. coli bacterial infection, both camel colostrum and mixed colostrum stimulated TNF-α. The highest enhancement was for camel colostrum in all treatments (0.56 pg/ml, 0.57 pg/ml, and 0.60 pg/ml for colostrum alone, bacteria alone, and colostrum with bacteria, respectively). These results are summarized in Table 9 and FIG. 3. Data from the full month-long experiment are presented in FIGS. 4A-4C.

TABLE 9

E. coli and TNF-α Immune Response in the Presence of Colostrum (Expressed as Median pg/ml (Min-Max))

| Colostrum Type | Camel | Bovine | Mix | P value[A] |
|---|---|---|---|---|
| Healthy | 0.00 | 0.00 | 0.00 | 1.000 |
| | (0.00-0.60) | (0.00-0.60) | (0.00-0.60) | |
| Colostrum | 0.56 | 0.00 | 0.03 | 0.261 |
| | (0.00-0.94) | (0.00-194.80) | (0.00-0.62) | |
| Bacteria | 0.57 | 0.00 | 0.18 | 0.033 |
| | (0.00-1.13) | (0.00-0.22) | (0.00-0.96) | |
| Colostrum & Bacteria | 0.60 | 0.00 | 0.23 | 0.002 |
| | (0.25-1.00) | (0.00-0.00) | (0.00-0.76) | |
| P value[B] | 0.101 | 0.331 | 0.373 | |

[A]=Comparison between different treatments within a single Colostrum type using a Nonparametric Test (Kruskal-Wallis Test).
[B]=Comparison between different Colostrum types in each treatment using a Nonparametric Test (Kruskal-Wallis Test).

Figure 5:
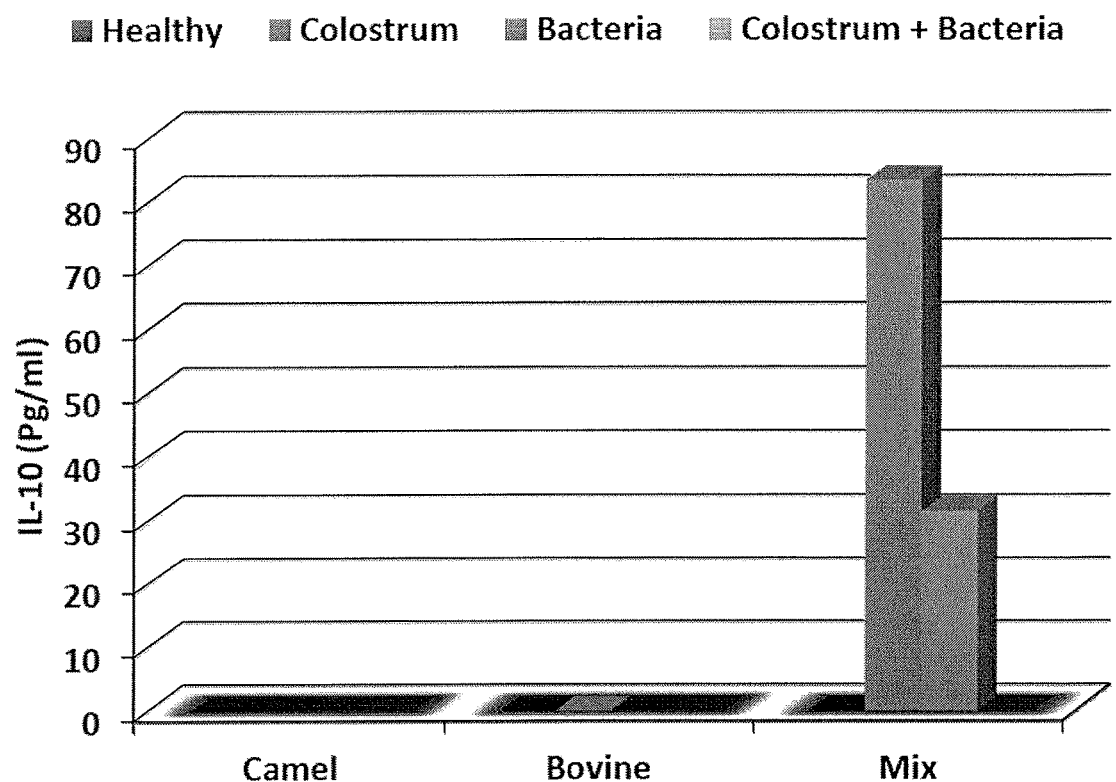
FIG. 5 depicts a bar graph displaying IL-10 levels in control subjects, subjects exposed to colostrum alone, subjects exposed to *E. coli* alone, and subjects exposed to both *E. coli* and colostrum, where the colostrum was either bovine colostrum, camel colostrum, or a mixture of bovine colostrum and camel colostrum.

In the model of E. coli bacterial infection, mixed colostrum alone triggered the IL-10 immune response more than the other treatments (83.30 pg/ml). The most enormous increase was observed in the presence of mixed colostrum and E. coli bacteria (1000.0 pg/ml at the Last point). (See Table 10 and FIG. 5)

TABLE 10

E. coli and IL-10 Immune Response in the Presence of Colostrum (Expressed as Median pg/ml (Min-Max))

| Colostrum Type | Camel | Bovine | Mix | P value[A] |
|---|---|---|---|---|
| Healthy | 0.00 | 0.00 | 0.00 | 1.000 |
| | (0.00-36.76) | (0.00-36.76) | (0.00-36.76) | |
| Colostrum | 0.00 | 0.14 | 83.30 | 0.115 |
| | (0.00-16.30) | (0.00-38.65) | (0.00-1000.00) | |
| Bacteria | 0.00 | 0.02 | 31.62 | 0.159 |
| | (0.00-0.64) | (0.00-0.26) | (0.00-1000.00) | |
| Colostrum & Bacteria | 0.00 | 0.01 | 0.01 | 0.290 |
| | (0.00-0.14) | (0.00-0.29) | (0.00-1000.00) | |
| P value[B] | 0.750 | 0.353 | 0.632 | |

[A]=Comparison between different treatments within a single Colostrum type using a Nonparametric Test (Kruskal-Wallis Test).
[B]=Comparison between different Colostrum types in each treatment using a Nonparametric Test (Kruskal-Wallis Test).

Figure 6A:
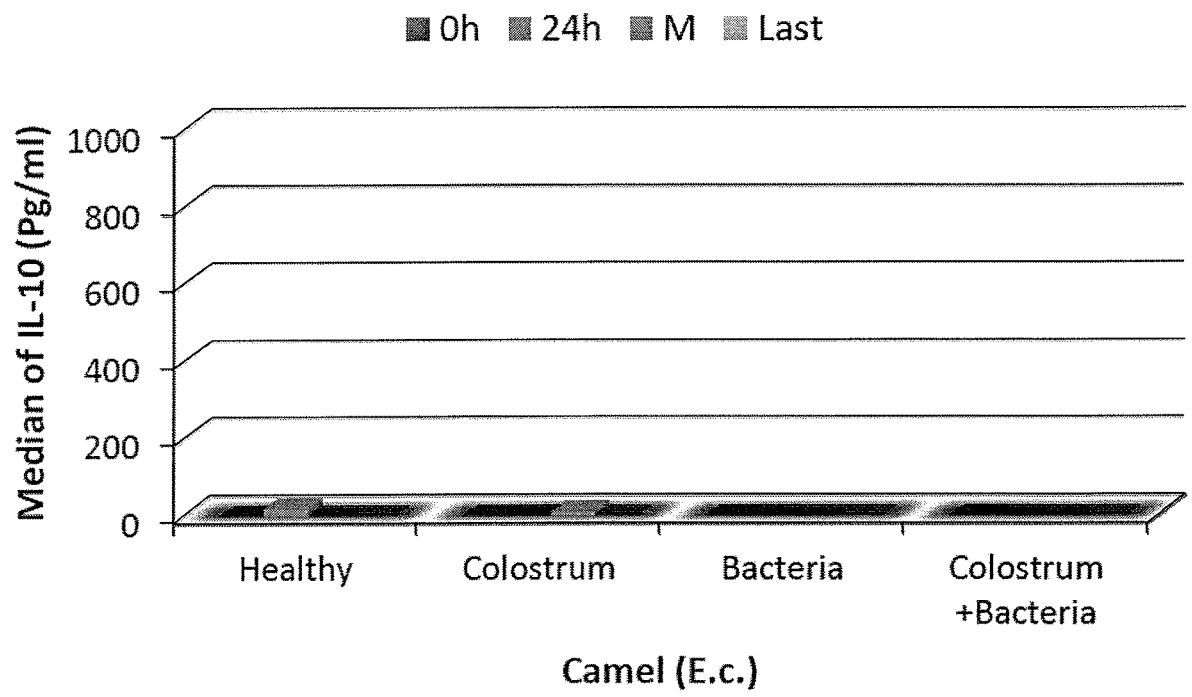
FIG. 6A depicts a bar graph displaying IL-10 levels over time in control subjects, subjects exposed to colostrum alone, subjects exposed to *E. coli* alone, and subjects exposed to both *E. coli* and colostrum, where the colostrum was camel colostrum.
Figure 6B:
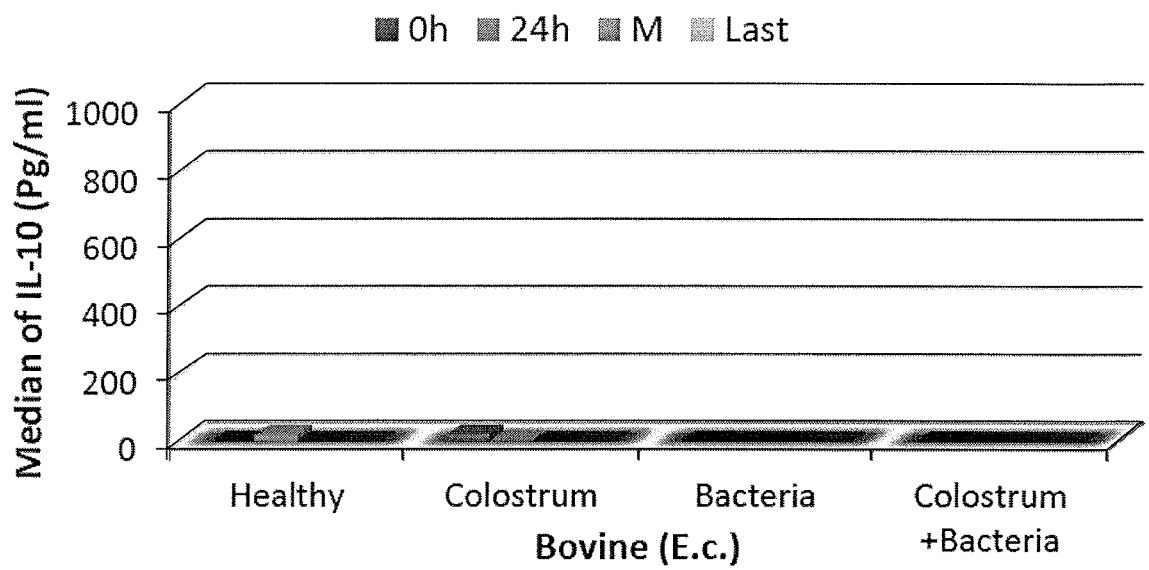
FIG. 6B depicts a bar graph displaying IL-10 levels over time in control subjects, subjects exposed to colostrum alone, subjects exposed to *E. coli* alone, and subjects exposed to both *E. coli* and colostrum, where the colostrum was bovine colostrum.
Figure 6C:
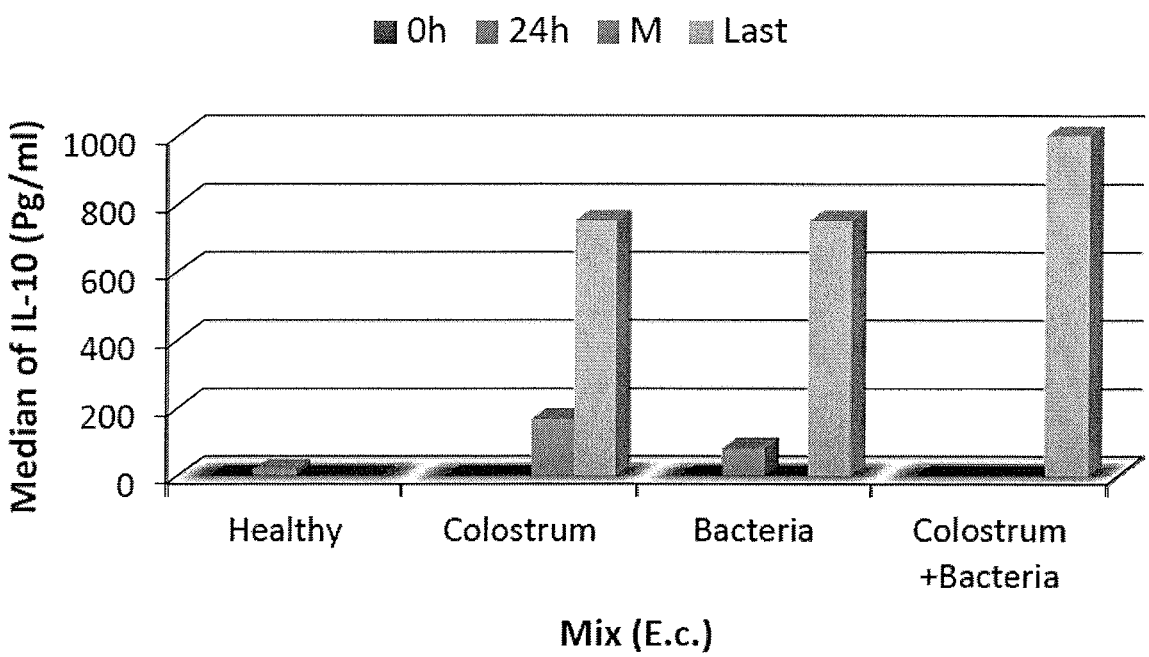
FIG. 6C depicts a bar graph displaying IL-10 levels over time in control subjects, subjects exposed to colostrum alone, subjects exposed to *E. coli* alone, and subjects exposed to both *E. coli* and colostrum, where the colostrum was a mixture of camel colostrum and bovine colostrum.

Data from the full month-long experiment are presented in Table 11 and FIGS. 6A-6C. IL-10 started to increase after 24 hours in the bacterial infection with 80.308 pg/ml. Moreover, colostrum continued to induce IL-10 from 7 days-25 days up to 166.60 pg/ml.

TABLE 11

E. coli and IL-10 Immune Response in the Presence of Colostrum at 0 h, 24 h, 7-25 days (M), and 30 days (Last) (Expressed as Median (Min-Max))

| Treatment Group | Time | Camel | Bovine | Mix |
|---|---|---|---|---|
| Healthy | 0 h | 0.016 | 0.016 | 0.016 |
| | | (0.000-0.030) | (0.000-0.030) | (0.000-0.030) |
| | 24 h | 18.378 | 18.378 | 18.378 |
| | | (0.000-36.760) | (0.000-36.760) | (0.000-36.760) |
| | M | 0.018 | 0.018 | 0.018 |
| | | (0.000-0.030) | (0.000-0.030) | (0.000-0.030) |
| | Last | 0.004 | 0.004 | 0.004 |
| | | (0.000-0.010) | (0.000-0.010) | (0.000-0.010) |
| P value | | 0.935 | 0.935 | 0.935 |
| Colostrum | 0 h | 0.000 | 19.621 | 0.001 |
| | | (0.000-0.000) | (0.590-38.650) | (0.000-0.000) |
| | 24 h | 0.000 | 0.810 | 0.002 |
| | | (0.000-0.000) | (0.150-1.470) | (0.000-0.000) |

TABLE 11-continued

E. coli and IL-10 Immune Response in the Presence
of Colostrum at 0 h, 24 h, 7-25 days (M), and
30 days (Last) (Expressed as Median (Min-Max))

| Treatment Group | Time | Camel | Bovine | Mix |
|---|---|---|---|---|
| | M | 8.152 | 0.077 | 166.63 |
| | | (0.000-16.300) | (0.020-0.130) | (166.60-166.66) |
| | Last | 0.005 | 0.001 | 750.0 |
| | | (0.000-0.000) | (0.000-0.000) | (500.0-1000.0) |
| | P value | 0.105 | 0.104 | 0.091 |
| Bacteria | 0 h | 0.000 | 0.156 | 0.010 |
| | | (0.000-0.000) | (0.050-0.260) | (0.000-0.020) |
| | 24 h | 0.318 | 0.017 | 80.308 |
| | | (0.000-0.640) | (0.010-0.020) | (63.220-97.400) |
| | M | 0.009 | 0.044 | 0.001 |
| | | (0.000-0.020) | (0.020-0.070) | (0.000-0.000) |
| | Last | 0.056 | 0.002 | 750.0 |
| | | (0.060-0.060) | (0.000-0.000) | (500.0-1000.0) |
| | P value | 0.467 | 0.139 | 0.080 |
| Colostrum & Bacteria | 0 h | 0.000 | 0.162 | 0.005 |
| | | (0.000-0.000) | (0.030-0.290) | (0.000-0.010) |
| | 24 h | 0.000 | 0.010 | 0.013 |
| | | (0.000-0.000) | (0.010-0.010) | (0.010-0.010) |
| | M | 0.006 | 0.010 | 0.001 |
| | | (0.000-0.010) | (0.010-0.010) | (0.000-0.000) |
| | Last | 0.089 | 0.006 | 1000.0 |
| | | (0.040-0.140) | (0.000-0.010) | (1000.0-1000.0) |
| | P value | 0.116 | 0.276 | 0.284 |

Figure 7:
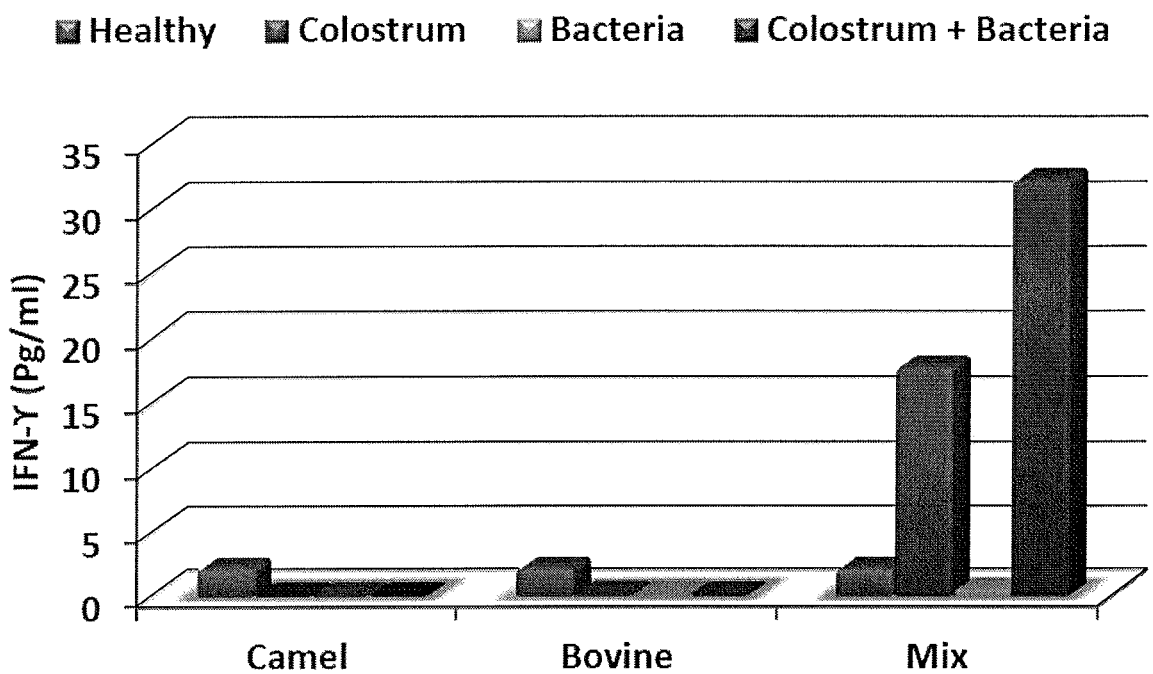
FIG. 7 depicts a bar graph displaying IFN-γ levels in control subjects, subjects exposed to colostrum alone, subjects exposed to *P. aeruginosa* alone, and subjects exposed to both *P. aeruginosa* and colostrum, where the colostrum was either bovine colostrum, camel colostrum, or a mixture of bovine colostrum and camel colostrum.
Figure 8A:
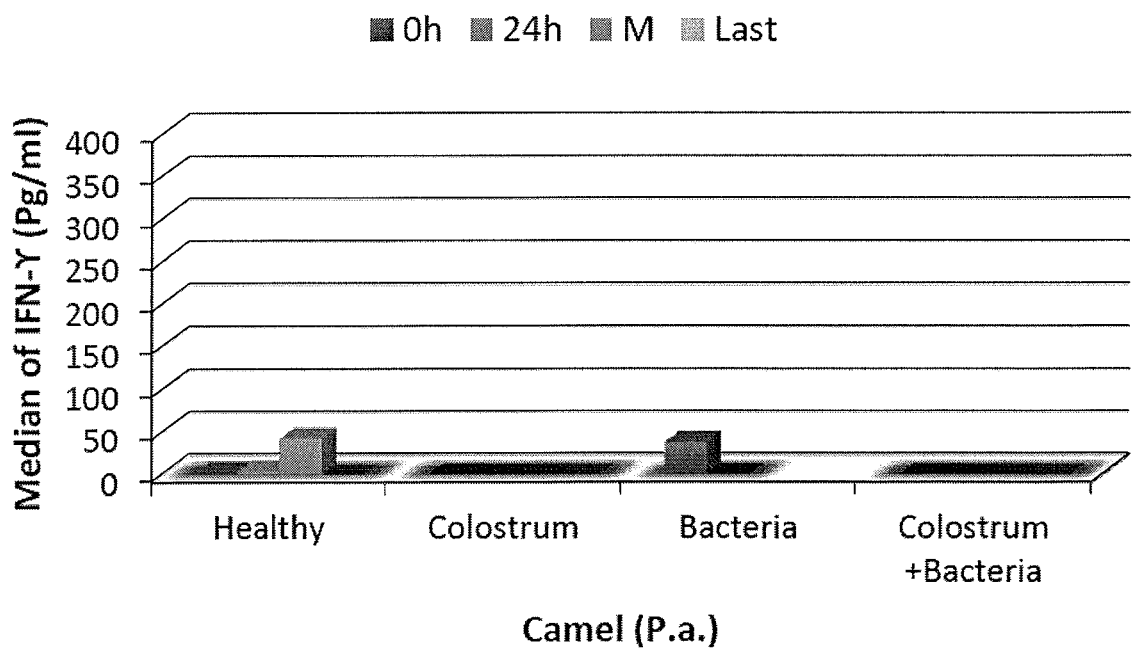
FIG. 8A depicts a bar graph displaying IFN-γ levels over time in control subjects, subjects exposed to colostrum alone, subjects exposed to *P. aeruginosa* alone, and subjects exposed to both *P. aeruginosa* and colostrum, where the colostrum was camel colostrum.
Figure 8B:
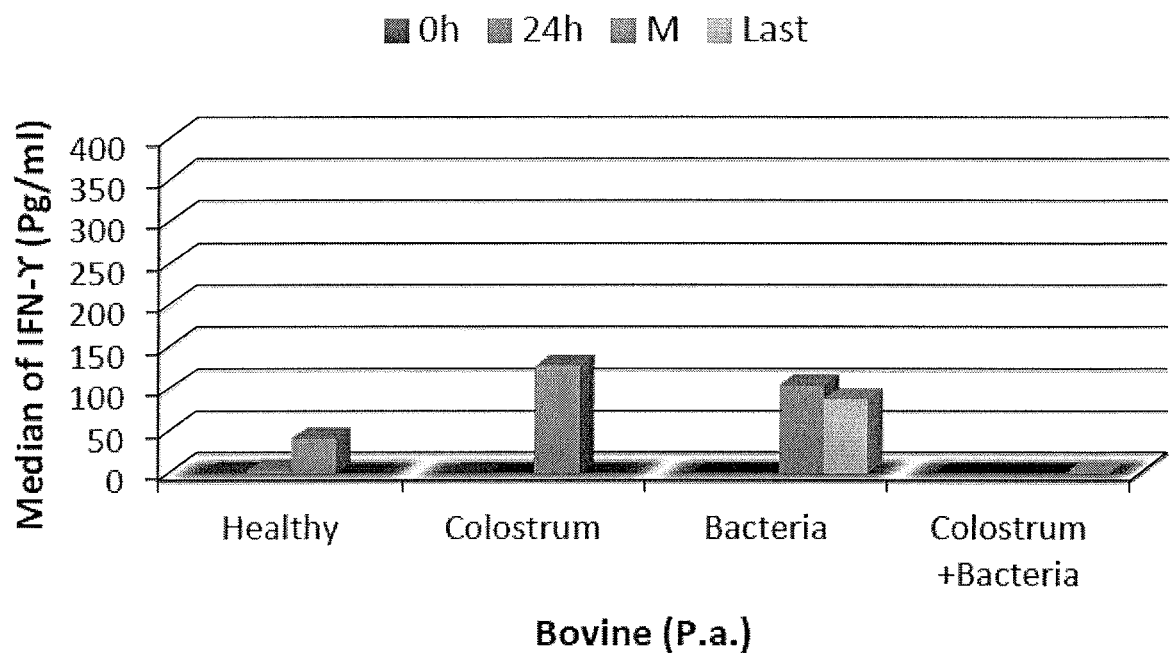
FIG. 8B depicts a bar graph displaying IFN-γ levels over time in control subjects, subjects exposed to colostrum alone, subjects exposed to *P. aeruginosa* alone, and subjects exposed to both *P. aeruginosa* and colostrum, where the colostrum was bovine colostrum.
Figure 8C:
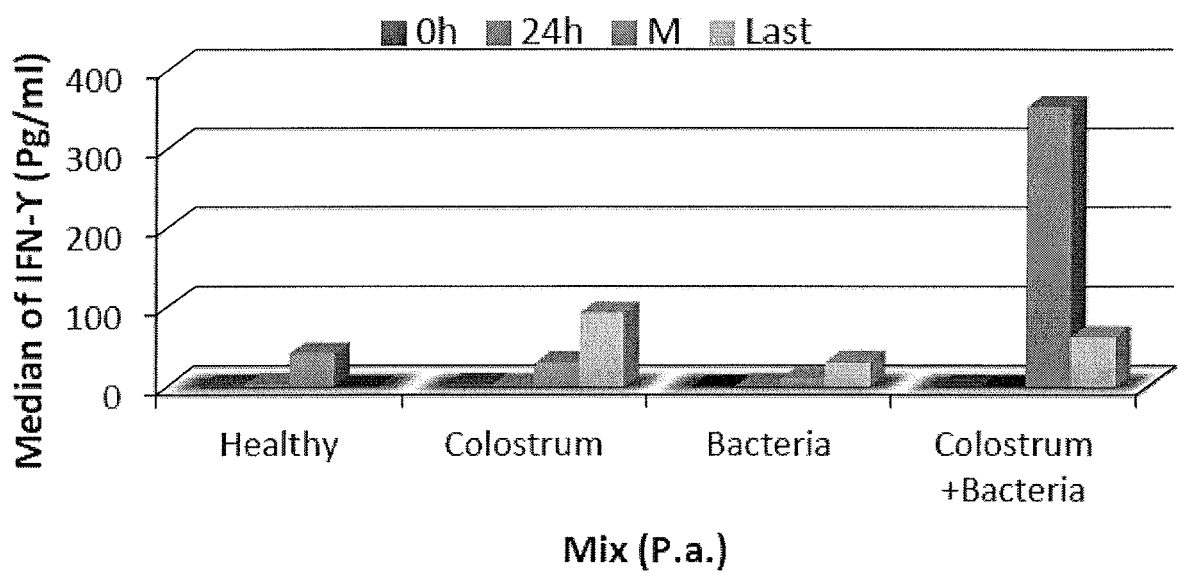
FIG. 8C depicts a bar graph displaying IFN-γ levels over time in control subjects, subjects exposed to colostrum alone, subjects exposed to *P. aeruginosa* alone, and subjects exposed to both *P. aeruginosa* and colostrum, where the colostrum was a mixture of camel colostrum and bovine colostrum.

In the model of P. aeruginosa infection, the mixed colostrum induced IFN-γ expression of 17.82 pg/ml. Further, the mixed colostrum combined with bacterial infection resulted in an IFN-γ expression of 32.22 pg/ml. These results are presented in Table 12 and FIG. 7. Data from the full month-long experiment are presented in FIGS. 8A-8C.

TABLE 12

P. aeruginosa and IFN-γ Immune Response in the
Presence of Colostrum (Expressed as Median pg/ml (Min-Max))

| Colostrum Type | Camel | Bovine | Mix | P value[A] |
|---|---|---|---|---|
| Healthy | 2.20 | 2.20 | 2.20 | 1.000 |
| | (0.00-43.91) | (0.00-43.91) | (0.00-43.91) | |
| Colostrum | 0.00 | 0.09 | 17.82 | 0.055 |
| | (0.00-0.03) | (0.00-209.50) | (0.00-125.00) | |
| Bacteria | 0.01 | 0.07 | 0.50 | 0.284 |
| | (0.00-74.40) | (0.02-105.79) | (0.01-62.50) | |
| Colostrum & Bacteria | 0.00 | 0.06 | 32.22 | 0.002 |
| | (0.00-0.00) | (0.03-0.49) | (0.00-457.20) | |
| P value[B] | 0.007 | 0.712 | 0.578 | |

[A]=Comparison between different treatments within a single Colostrum type using a Nonparametric Test (Kruskal-Wallis Test).
[B]=Comparison between different Colostrum types in each treatment using a Nonparametric Test (Kruskal-Wallis Test).

Figure 9:
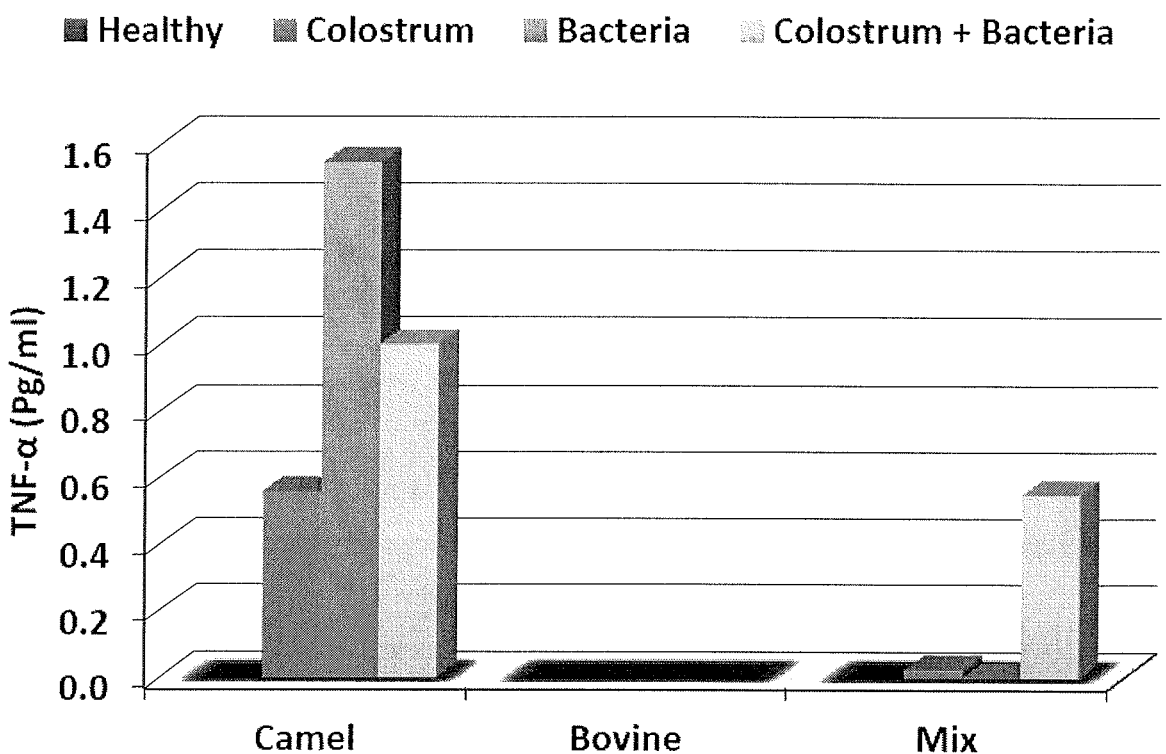
FIG. 9 depicts a bar graph displaying TNF-α levels in control subjects, subjects exposed to colostrum alone, subjects exposed to *P. aeruginosa* alone, and subjects exposed to both *P. aeruginosa* and colostrum, where the colostrum was either bovine colostrum, camel colostrum, or a mixture of bovine colostrum and camel colostrum.

In the model of P. aeruginosa infection, the most considerable enhancement of TNF-α expression was detected in the group administered camel colostrum, which demonstrated 0.56 pg/ml, 1.54 pg/ml and 1.00 pg/ml for colostrum treatment alone, bacterial treatment alone, and colostrum and bacterial treatment, respectively. These results are presented in Table 13 and FIG. 9.

TABLE 13

P. aeruginosa and TNF-α Immune Response in the Presence
of Colostrum (Expressed as Median pg/ml (Min-Max))

| Colostrum Type | Camel | Bovine | Mix | P value[A] |
|---|---|---|---|---|
| Healthy | 0.00 | 0.00 | 0.00 | 1.000 |
| | (0.00-0.60) | (0.00-0.60) | (0.00-0.60) | |
| Colostrum | 0.56 | 0.00 | 0.03 | 0.261 |
| | (0.00-0.94) | (0.00-194.80) | (0.00-0.62) | |
| Bacteria | 1.54 | 0.00 | 0.00 | 0.004 |
| | (0.54-1.91) | (0.00-0.00) | (0.00-1.09) | |
| Colostrum & Bacteria | 1.00 | 0.00 | 0.55 | 0.006 |
| | (0.00-12.50) | (0.00-0.00) | (0.00-4.58) | |
| P value[B] | 0.025 | 0.185 | 0.663 | |

[A]=Comparison between different treatments within a single Colostrum type using a Nonparametric Test (Kruskal-Wallis Test).
[B]=Comparison between different Colostrum types in each treatment using a Nonparametric Test (Kruskal-Wallis Test).

Figure 10A:
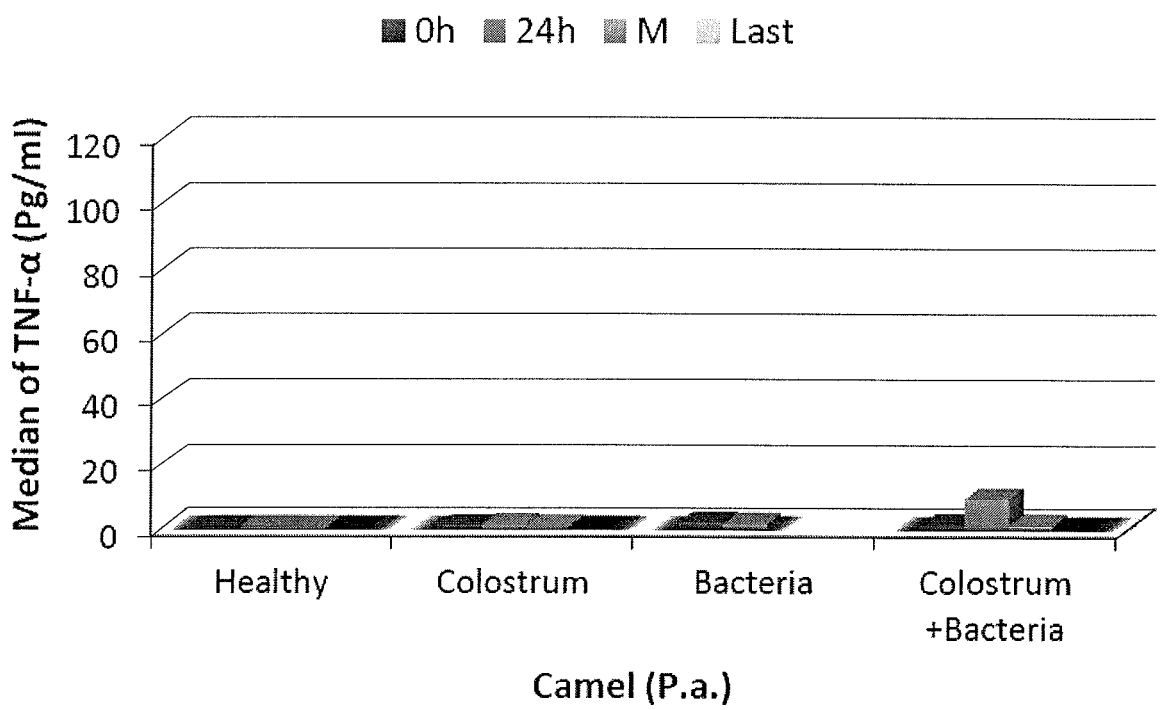
FIG. 10A depicts a bar graph displaying TNF-α levels over time in control subjects, subjects exposed to colostrum alone, subjects exposed to *P. aeruginosa* alone, and subjects exposed to both *P. aeruginosa* and colostrum, where the colostrum was camel colostrum.
Figure 10B:
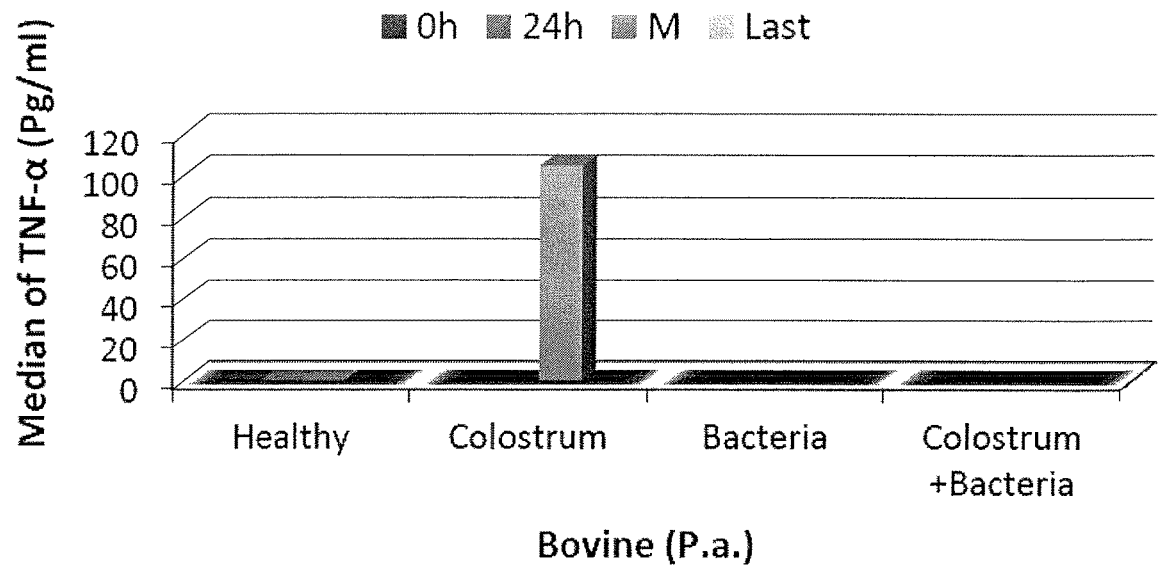
FIG. 10B depicts a bar graph displaying TNF-α levels over time in control subjects, subjects exposed to colostrum alone, subjects exposed to *P. aeruginosa* alone, and subjects exposed to both *P. aeruginosa* and colostrum, where the colostrum was bovine colostrum.
Figure 10C:
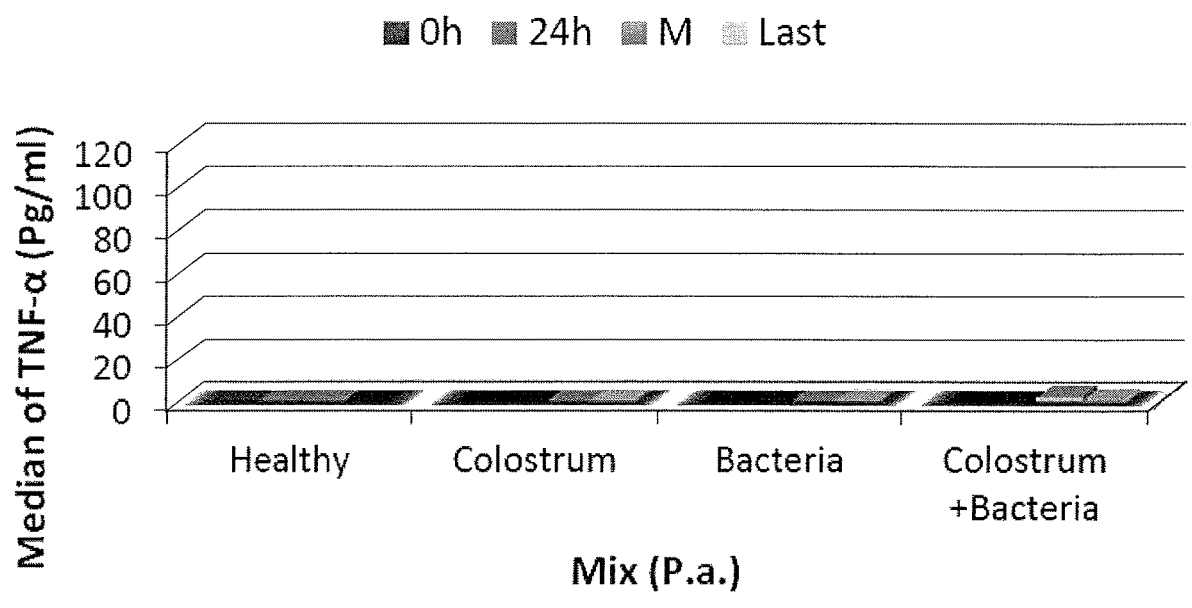
FIG. 10C depicts a bar graph displaying TNF-α levels over time in control subjects, subjects exposed to colostrum alone, subjects exposed to *P. aeruginosa* alone, and subjects exposed to both *P. aeruginosa* and colostrum, where the colostrum was a mixture of camel colostrum and bovine colostrum.

Data from the month-long experiment are presented in Table 14 and FIGS. 10A-10C. P. aeruginosa administration increased TNF-α expression after 24 hours to 1.171 pg/ml. In comparison, an expression level of 0.828 pg/ml was detected for camel colostrum administration. The most efficient change in TNF-α expression was observed for the administration of both camel colostrum and P. aeruginosa (8.931 pg/ml 24 hours after administration of the bacterium).

TABLE 14

*P. aeruginosa* and TNF-α Immune Response in the Presence of Colostrum at 0 h, 24 h, 7-25 days (M), and 30 days (Last) (Expressed as Median(Min-Max))

| Treatment | Time | Camel | Bovine | Mix |
|---|---|---|---|---|
| Healthy | 0 h | 0.300 (0.000-0.600) | 0.300 (0.000-0.600) | 0.300 (0.000-0.600) |
| | 24 h | 0.220 (0.000-0.440) | 0.220 (0.000-0.440) | 0.220 (0.000-0.440) |
| | M | 0.269 (0.000-0.540) | 0.269 (0.000-0.540) | 0.269 (0.000-0.540) |
| | Last | 0.000 (0.000-0.000) | 0.000 (0.000-0.000) | 0.000 (0.000-0.000) |
| | P value | 0.675 | 0.675 | 0.675 |
| Colostrum | 0 h | 0.558 (0.540-0.580) | 0.000 (0.000-0.000) | 0.000 (0.000-0.000) |
| | 24 h | 0.828 (0.720-0.940) | 0.000 (0.000-0.000) | 0.000 (0.000-0.000) |
| | M | 0.430 (0.170-0.690) | 104.749 (14.70-194.80) | 0.177 (0.050-0.300) |
| | Last | 0.000 (0.000-0.000) | 0.000 (0.000-0.000) | 0.490 (0.360-0.620) |
| | P value | 0.108 | 0.077 | 0.078 |
| Bacteria | 0 h | 1.594 (1.280-1.910) | 0.000 (0.000-0.000) | 0.000 (0.000-0.000) |
| | 24 h | 1.171 (0.540-1.800) | 0.000 (0.000-0.000) | 0.000 (0.000-0.000) |
| | M | — | 0.000 (0.000-0.000) | 0.185 (0.000-0.360) |
| | Last | — | 0.000 (0.000-0.000) | 0.550 (0.010-1.090) |
| | P value | 0.439 | 1.000 | 0.100 |
| Colostrum & Bacteria | 0 h | 0.769 (0.540-1.000) | 0.000 (0.000-0.000) | 0.000 (0.000-0.000) |
| | 24 h | 8.931 (5.360-12.500) | 0.000 (0.000-0.000) | 0.000 (0.000-0.000) |
| | M | 0.861 (0.360-1.360) | 0.000 (0.000-0.000) | 2.568 (0.550-4.580) |
| | Last | 0.000 (0.000-0.000) | 0.000 (0.000-0.000) | 0.695 (0.560-0.830) |
| | P value | 0.185 | 1.000 | 0.183 |

Figure 11:
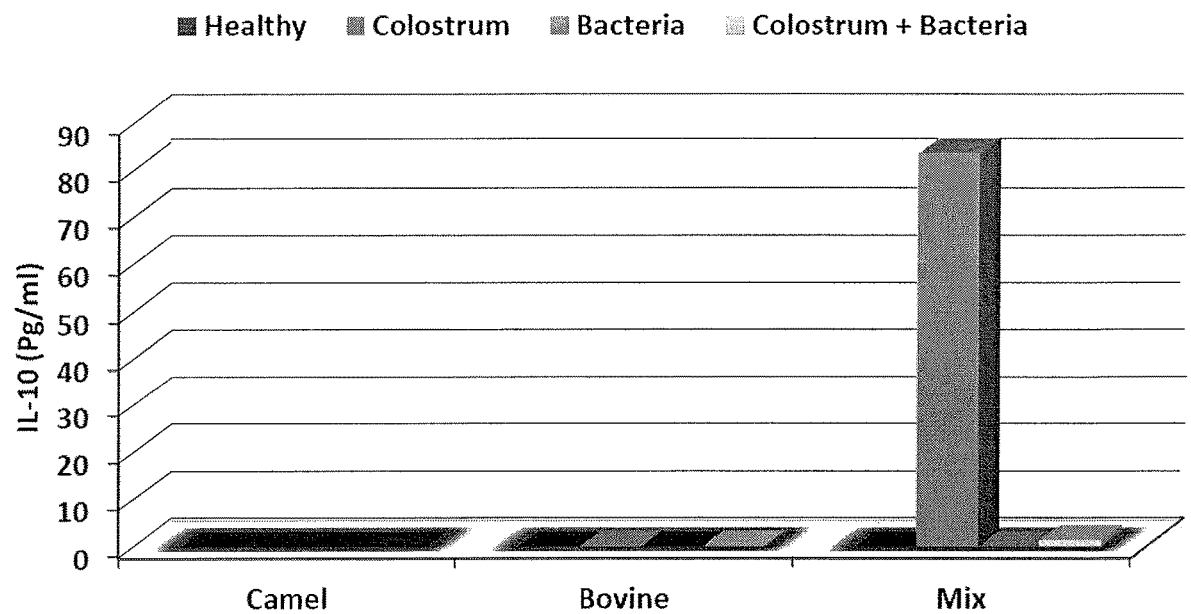
FIG. 11 depicts a bar graph displaying IL-10 levels in control subjects, subjects exposed to colostrum alone, subjects exposed to *P. aeruginosa* alone, and subjects exposed to both *P. aeruginosa* and colostrum, where the colostrum was either bovine colostrum, camel colostrum, or a mixture of bovine colostrum and camel colostrum.
Figure 12A:
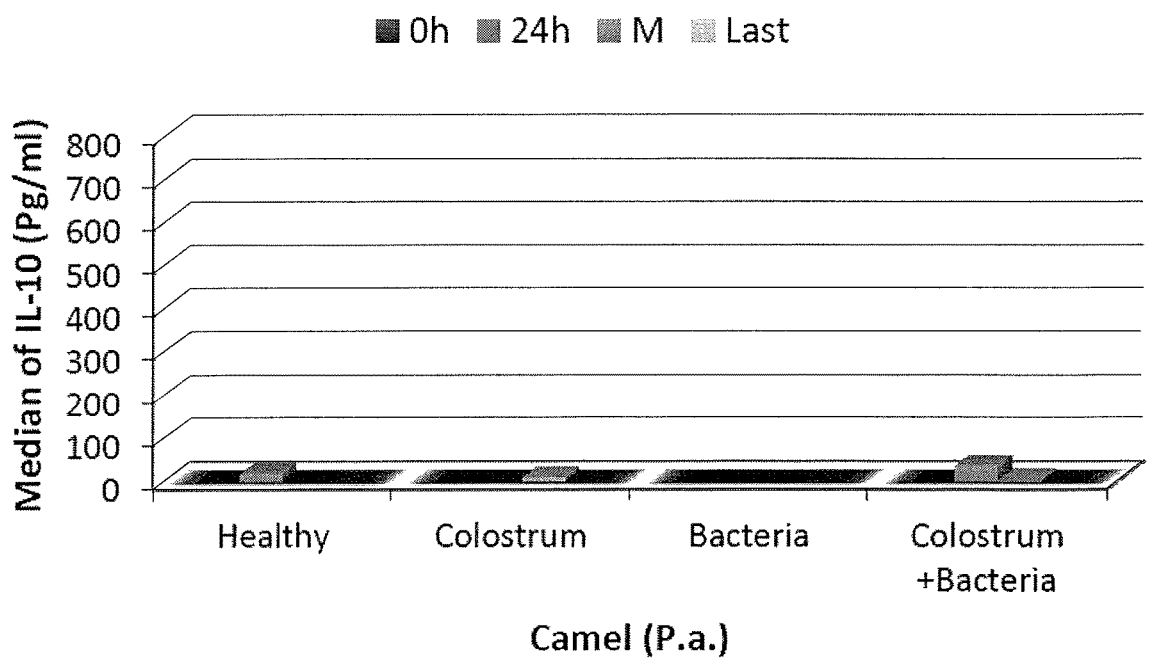
FIG. 12A depicts a bar graph displaying IL-10 levels over time in control subjects, subjects exposed to colostrum alone, subjects exposed to *P. aeruginosa* alone, and subjects exposed to both *P. aeruginosa* and colostrum, where the colostrum was camel colostrum.
Figure 12B:
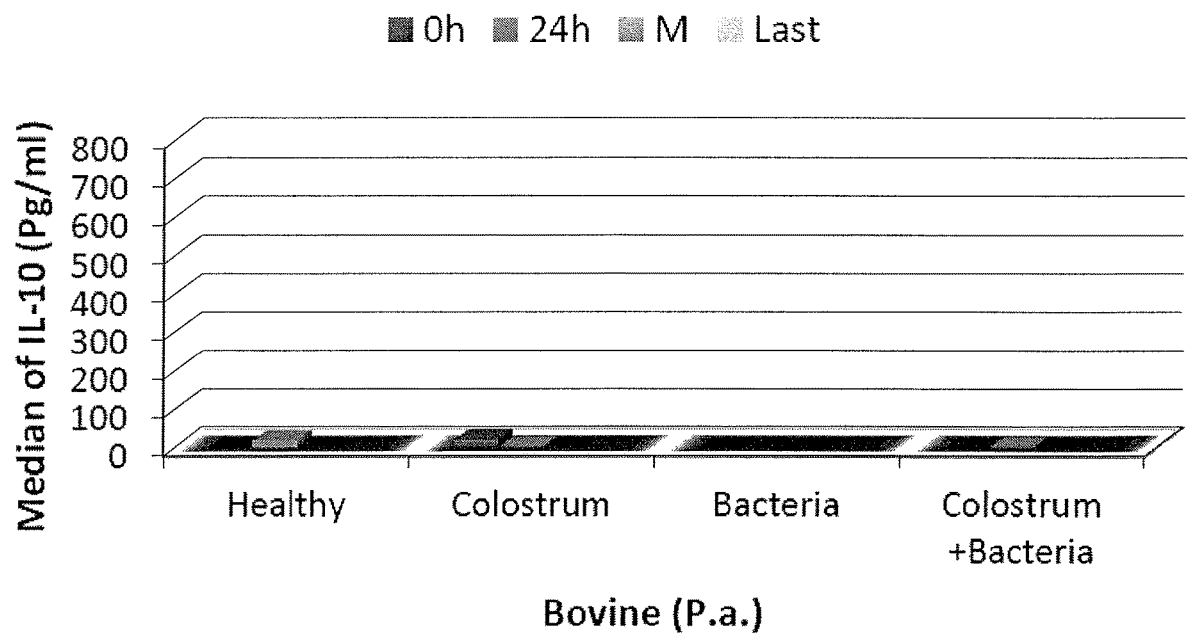
FIG. 12B depicts a bar graph displaying IL-10 levels over time in control subjects, subjects exposed to colostrum alone, subjects exposed to *P. aeruginosa* alone, and subjects exposed to both *P. aeruginosa* and colostrum, where the colostrum was bovine colostrum.
Figure 12C:
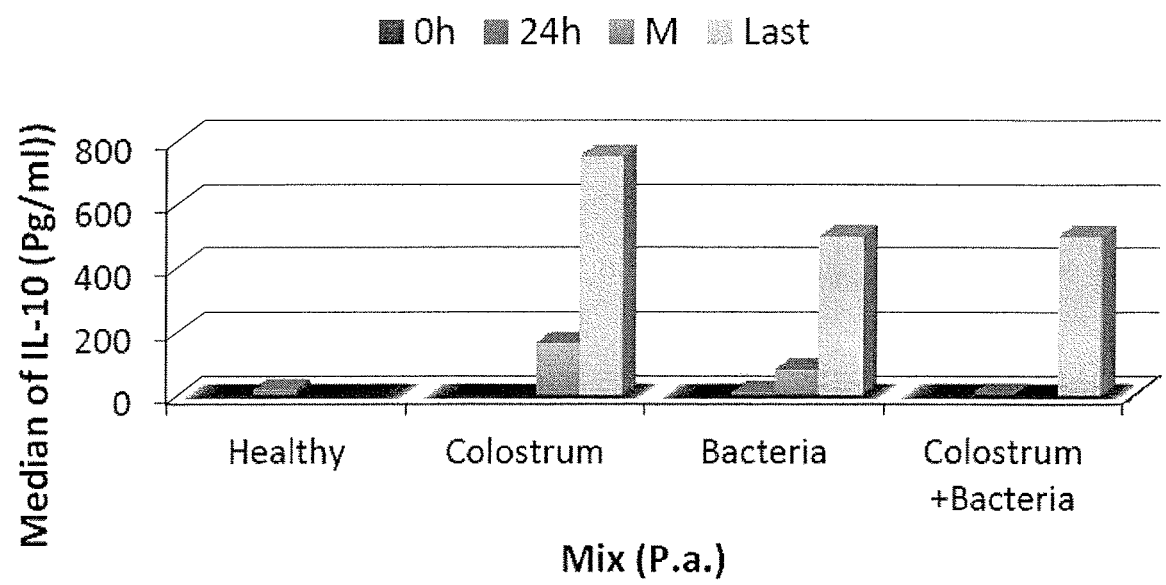
FIG. 12C depicts a bar graph displaying IL-10 levels over time in control subjects, subjects exposed to colostrum alone, subjects exposed to *P. aeruginosa* alone, and subjects exposed to both *P. aeruginosa* and colostrum, where the colostrum was a mixture of camel colostrum and bovine colostrum.

In the model of *P. aeruginosa* infection, the administration of the mixture of colostrum alone caused the greatest change in IL-10 levels (83.30 pg/ml), as shown in Table 15 and FIG. 11. Data from the month-long experiment are presented in Table 16 and FIGS. 12A-12C.

TABLE 15

*P. aeruginosa* and IL-10 Immune Response in the Presence of Colostrum (Expressed as Median pg/ml (Min-Max))

| Colostrum Type | Camel | Bovine | Mix | P value[A] |
|---|---|---|---|---|
| Healthy | 0.00 (0.00-36.76) | 0.00 (0.00-36.76) | 0.00 (0.00-36.76) | 1.000 |
| Colostrum | 0.00 (0.00-16.30) | 0.14 (0.00-38.65) | 83.30 (0.00-1000.00) | 0.115 |
| Bacteria | 0.00 (0.00-0.01) | 0.01 (0.01-0.03) | 0.07 (0.00-500.00) | 0.019 |
| Colostrum & Bacteria | 0.00 (0.00-72.69) | 0.08 (0.00-1.67) | 1.31 (0.00-500.00) | 0.388 |
| P value[B] | 0.749 | 0.321 | 0.286 | |

[A]=Comparison between different treatments within a single Colostrum type using a Nonparametric Test (Kruskal-Wallis Test).
[B]=Comparison between different Colostrum types in each treatment using a Nonparametric Test (Kruskal-Wallis Test).

TABLE 16

*P. aeruginosa* and IL-10 Immune Response in the Presence of Colostrum at 0 h, 24 h, 7-25 days (M), and 30 days (Last) (Expressed as Median(Min-Max))

| Treatment | Time | Camel | Bovine | Mix |
|---|---|---|---|---|
| Healthy | 0 h | 0.016 (0.000-0.030) | 0.016 (0.000-0.030) | 0.016 (0.000-0.030) |
| | 24 h | 18.378 (0.000-36.760) | 18.378 (0.000-36.760) | 18.378 (0.000-36.760) |

TABLE 16-continued

*P. aeruginosa* and IL-10 Immune Response in the
Presence of Colostrum at 0 h, 24 h, 7-25 days (M), and
30 days (Last) (Expressed as Median(Min-Max))

| Treatment | Time | Camel | Bovine | Mix |
|---|---|---|---|---|
| | M | 0.018 | 0.018 | 0.018 |
| | | (0.000-0.030) | (0.000-0.030) | (0.000-0.030) |
| | Last | 0.004 | 0.004 | 0.004 |
| | | (0.000-0.010) | (0.000-0.008) | (0.000-0.010) |
| P value | | 0.935 | 0.935 | 0.935 |
| Colostrum | 0 h | 0.000 | 19.621 | 0.001 |
| | | (0.000-0.000) | (0.590-38.650) | (0.000-0.000) |
| | 24 h | 0.000 | 0.810 | 0.002 |
| | | (0.000-0.000) | (0.150-1.470) | (0.000-0.000) |
| | M | 8.152 | 0.077 | 166.63 |
| | | (0.000-16.300) | (0.020-0.130) | (166.60-166.66) |
| | Last | 0.005 | 0.001 | 750.00 |
| | | (0.000-0.000) | (0.001-0.001) | (500.0-1000.0) |
| P value | | 0.105 | 0.104 | 0.091 |
| Bacteria | 0 h | 0.001 | 0.020 | 0.029 |
| | | (0.001-0.001) | (0.010-0.030) | (0.020-0.040) |
| | 24 h | 0.004 | 0.007 | 8.914 |
| | | (0.000-0.008) | (0.010-0.010) | (0.070-17.760) |
| | M | — | 0.008 | 83.301 |
| | | | (0.010-0.010) | (0.000-166.600) |
| | Last | — | 0.009 | 500.00 |
| | | | (0.010-0.010) | (500.00-500.00) |
| P value | | 1.000 | 0.701 | 0.375 |
| Colostrum | 0 h | 0.000 | 0.008 | 0.043 |
| & | | (0.000-0.000) | (0.000-0.020) | (0.040-0.050) |
| Bacteria | 24 h | 36.414 | 1.173 | 3.653 |
| | | (0.140-72.690) | (0.670-1.670) | (2.570-4.740) |
| | M | 3.601 | 0.030 | 0.002 |
| | | (0.000-7.200) | (0.030-0.030) | (0.001-0.002) |
| | Last | 0.002 | 0.128 | 500.00 |
| | | (0.000-0.000) | (0.130-0.130) | (500.00-500.00) |
| P value | | 0.297 | 0.194 | 0.080 |

Figure 13:
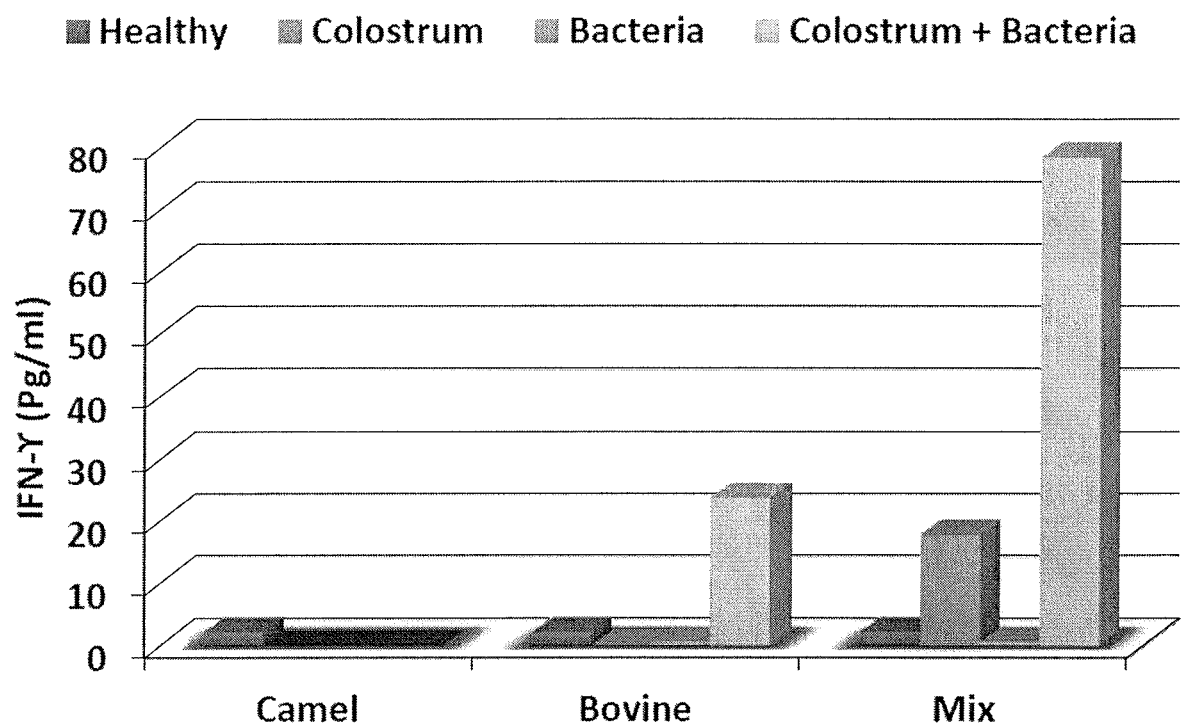
FIG. 13 depicts a bar graph displaying IFN-γ levels in control subjects, subjects exposed to colostrum alone, subjects exposed to *S. aureus* alone, and subjects exposed to both *S. aureus* and colostrum, where the colostrum was either bovine colostrum, camel colostrum, or a mixture of bovine colostrum and camel colostrum.

In the model of *S. aureus* subsp. *aureus* Rosenbach infection, IFN-γ levels increased to 78.10 pg/ml when the mixed colostrum and bacteria were administered, as compared to 17.82 pg/ml when the mixed colostrum alone was administered (see Table 17 and FIG. 13).

TABLE 17

*S. aureus* and IFN-γ Immune Response in the Presence
of Colostrum (Expressed as Median pg/ml (Min-Max))

| | Colostrum Type: | | | |
|---|---|---|---|---|
| | Camel | Bovine | Mix | P value[A] |
| Healthy | 2.20(0.00-43.91) | 2.20(0.00-43.91) | 2.20(0.00-43.91) | 1.000 |
| Colostrum | 0.00(0.00-0.03) | 0.09(0.00-209.50) | 17.82(0.00-125.00) | 0.055 |
| Bacteria | 0.01(0.00-64.78) | 0.44(0.04-75.23) | 0.50(0.01-62.50) | 0.076 |
| Colostrum & Bacteria | 0.02(0.00-2.91) | 23.76(0.01-94.87) | 78.10(0.03-6541.00) | 0.008 |
| P value[B] | 0.026 | 0.436 | 0.362 | |

[A] = Comparison between different treatments within a single Colostrum type using a Nonparametric Test (Kruskal-Wallis Test).
[B] = Comparison between different Colostrum types in each treatment using a Nonparametric Test (Kruskal-Wallis Test).

Figure 14A:
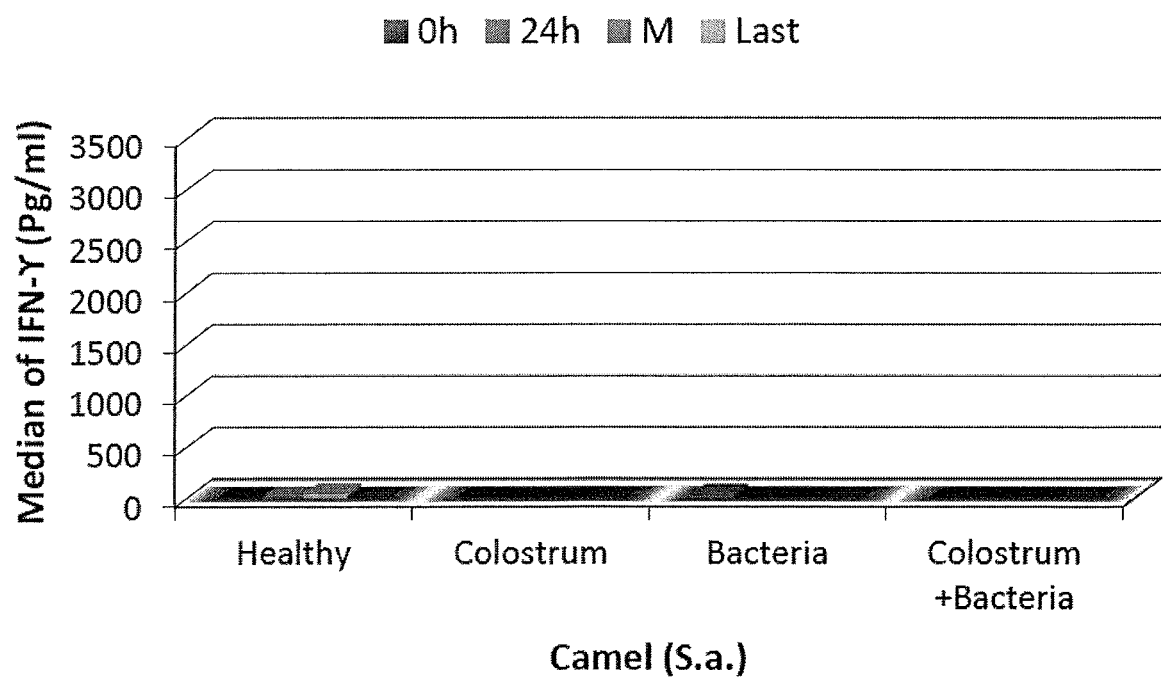
FIG. 14A depicts a bar graph displaying IFN-γ levels over time in control subjects, subjects exposed to colostrum alone, subjects exposed to *S. aureus* alone, and subjects exposed to both *S. aureus* and colostrum, where the colostrum was camel colostrum.
Figure 14B:
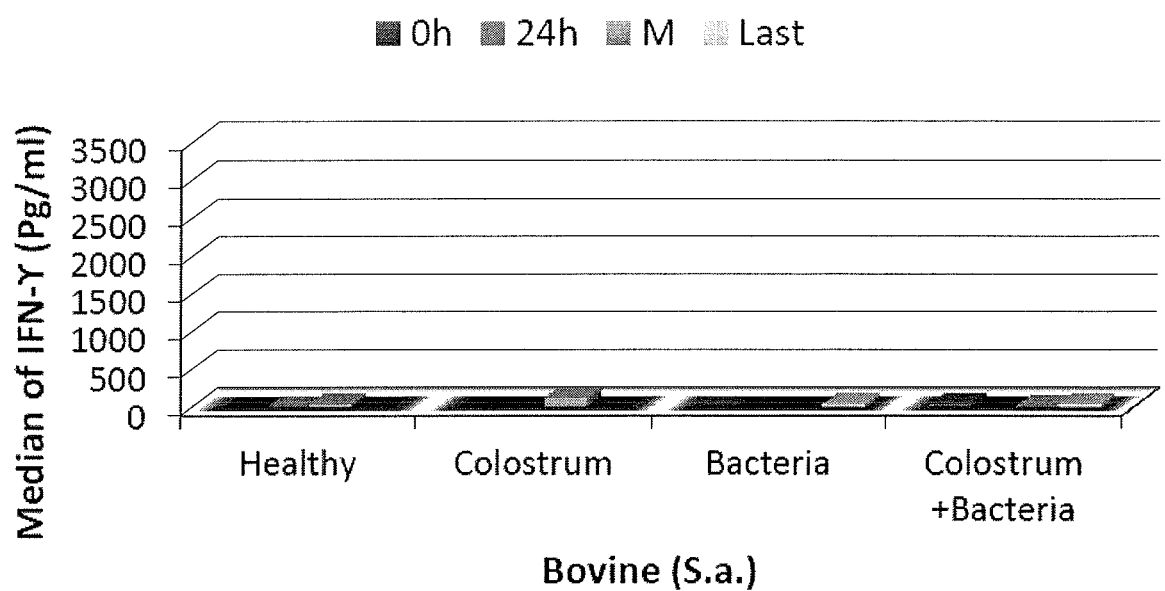
FIG. 14B depicts a bar graph displaying IFN-γ levels over time in control subjects, subjects exposed to colostrum alone, subjects exposed to *S. aureus* alone, and subjects exposed to both *S. aureus* and colostrum, where the colostrum was bovine colostrum.
Figure 14C:
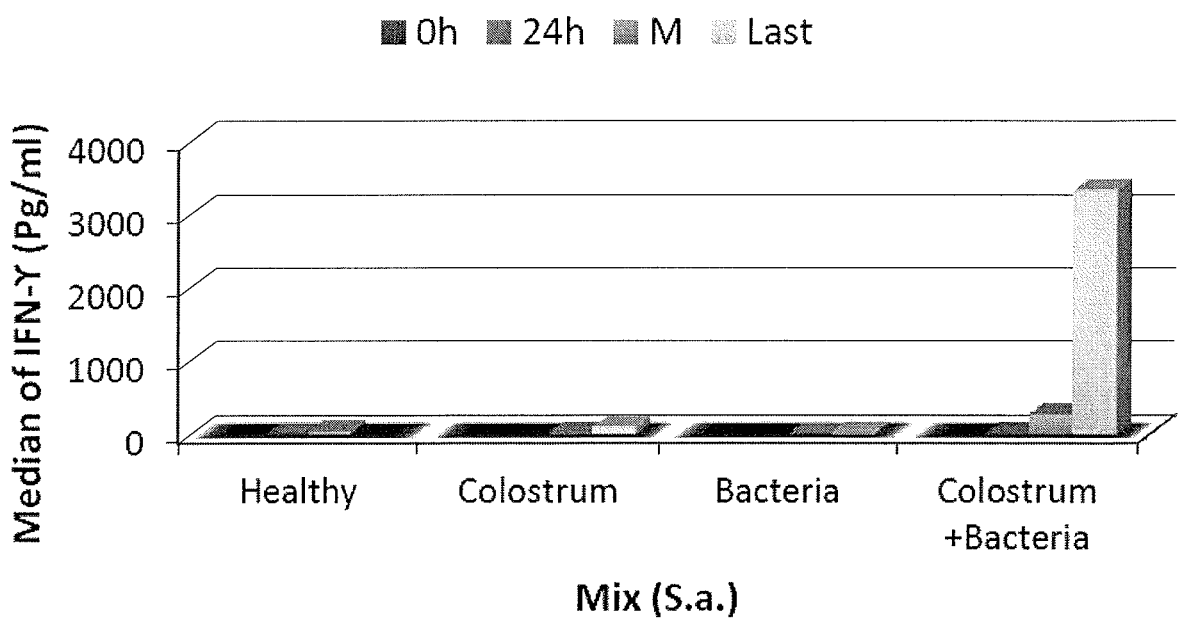
FIG. 14C depicts a bar graph displaying IFN-γ levels over time in control subjects, subjects exposed to colostrum alone, subjects exposed to *S. aureus* alone, and subjects exposed to both *S. aureus* and colostrum, where the colostrum was a mixture of camel colostrum and bovine colostrum.

In the month-long experiment, administration of the mixture of colostrum and *S. aureus* resulted in an increased level of IFN-γ of 3333.0 pg/ml by the final time-point. In comparison, at days 7-25 (M), the median IFN-γ level of rats administered mixed colostrum and *S. aureus* was 278.15 pg/ml. At the 24 hour time-point this level was only 15.647 pg/ml. These results are presented in Table 18 and FIGS. 14A-14C.

TABLE 18

S. aureus and IFN-γ Immune Response in the Presence of Colostrum at 0 h, 24 h, 7-25 days (M), and 30 days (Last) (Expressed as Median(Min-Max))

| Treatment | Time | Camel | Bovine | Mix |
|---|---|---|---|---|
| Healthy | 0 h | 1.496(0.220-2.770) | 1.496(0.220-2.770) | 1.496(0.220-2.770) |
|  | 24 h | 3.587(1.630-5.550) | 3.587(1.630-5.550) | 3.587(1.630-5.550) |
|  | M | 42.175(40.440-43.910) | 42.175(40.440-43.910) | 42.175(40.440-43.910) |
|  | Last | 0.005(0.000-0.010) | 0.005(0.000-0.010) | 0.005(0.000-0.010) |
| P value |  | 0.104 | 0.104 | 0.104 |
| Colostrum | 0 h | 0.019(0.008-0.030) | 1.055(0.120-1.990) | 3.129(0.000-6.260) |
|  | 24 h | 0.002(0.000-0.004) | 0.058(0.060-0.060) | 1.667(0.000-3.330) |
|  | M | 0.002(0.001-0.002) | 128.800(48.10-209.50) | 30.327(29.390-31.260) |
|  | Last | 0.005(0.003-0.006) | 0.001(0.001-0.001) | 93.750(62.50-125.00) |
| P value |  | 0.160 | 0.078 | 0.106 |
| Bacteria | 0 h | 32.400(0.020-64.780) | 6.787(0.090-13.480) | 0.194(0.110-0.280) |
|  | 24 h | 0.066(0.001-0.130) | 0.356(0.050-0.670) | 2.022(0.710-3.330) |
|  | M | 0.005(0.003-0.007) | 2.241(0.210-4.270) | 10.450(0.070-20.830) |
|  | Last | 0.002(0.000-0.002) | 37.639(0.040-75.230) | 31.256(0.010-62.500) |
| P value |  | 0.426 | 0.919 | 0.881 |
| Colostrum & | 0 h | 1.558(0.210-2.910) | 47.440(0.010-94.870) | 0.140(0.030-0.250) |
| Bacteria | 24 h | 0.010(0.000-0.010) | 0.355(0.360-0.360) | 15.647(0.090-31.200) |
|  | M | 0.008(0.000-0.010) | 18.174(12.590-23.760) | 278.15(173.90-382.40) |
|  | Last | 0.033(0.020-0.050) | 46.956(37.680-56.230) | 3333.00(125.0-6541.0) |
| P value |  | 0.106 | 0.587 | 0.139 |

Figure 15:
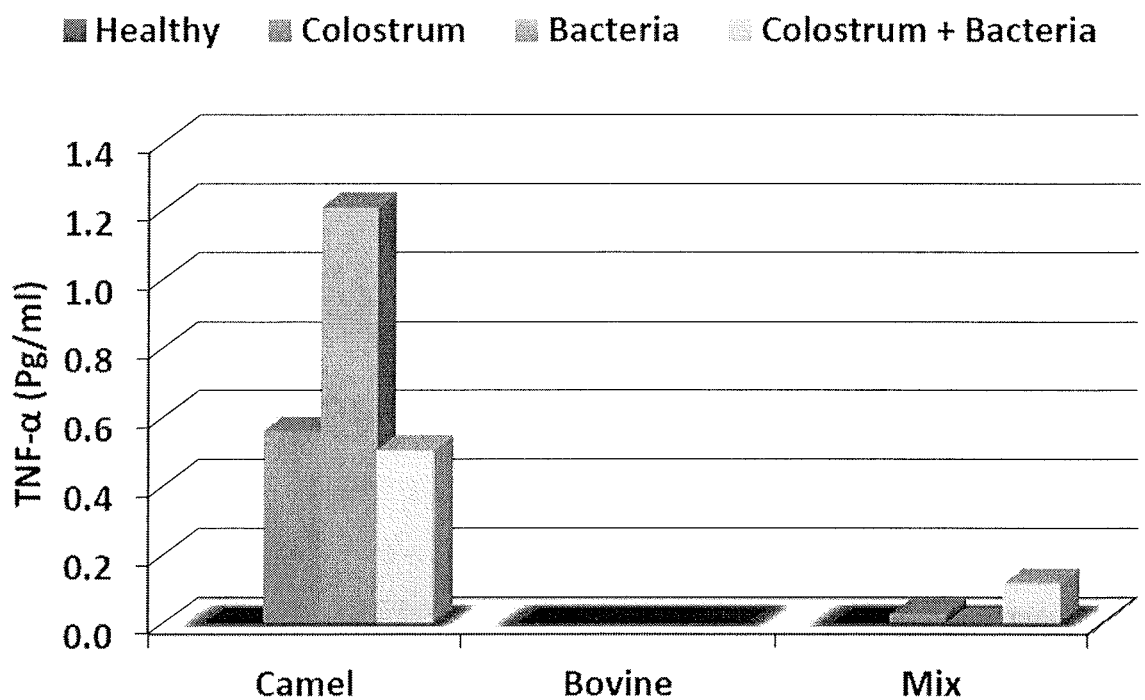
FIG. 15 depicts a bar graph displaying TNF-α levels in control subjects, subjects exposed to colostrum alone, subjects exposed to *S. aureus* alone, and subjects exposed to both *S. aureus* and colostrum, where the colostrum was either bovine colostrum, camel colostrum, or a mixture of bovine colostrum and camel colostrum.
Figure 16A:
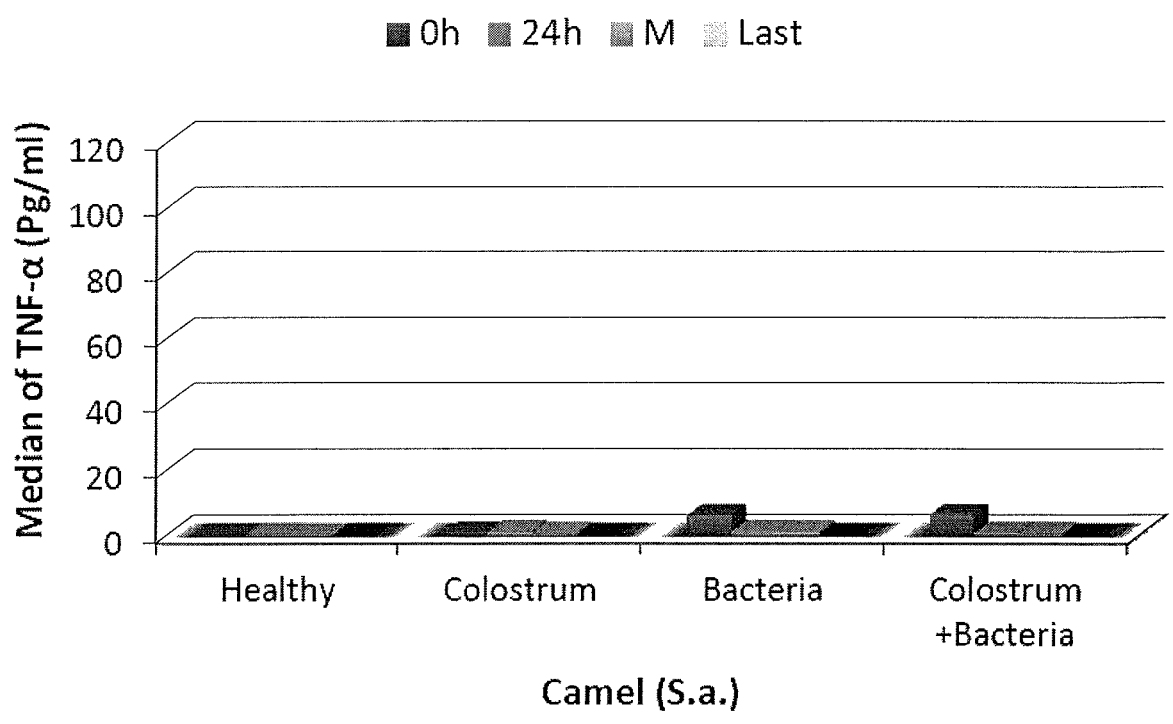
FIG. 16A depicts a bar graph displaying TNF-α levels over time in control subjects, subjects exposed to colostrum alone, subjects exposed to *S. aureus* alone, and subjects exposed to both *S. aureus* and colostrum, where the colostrum was camel colostrum.
Figure 16B:
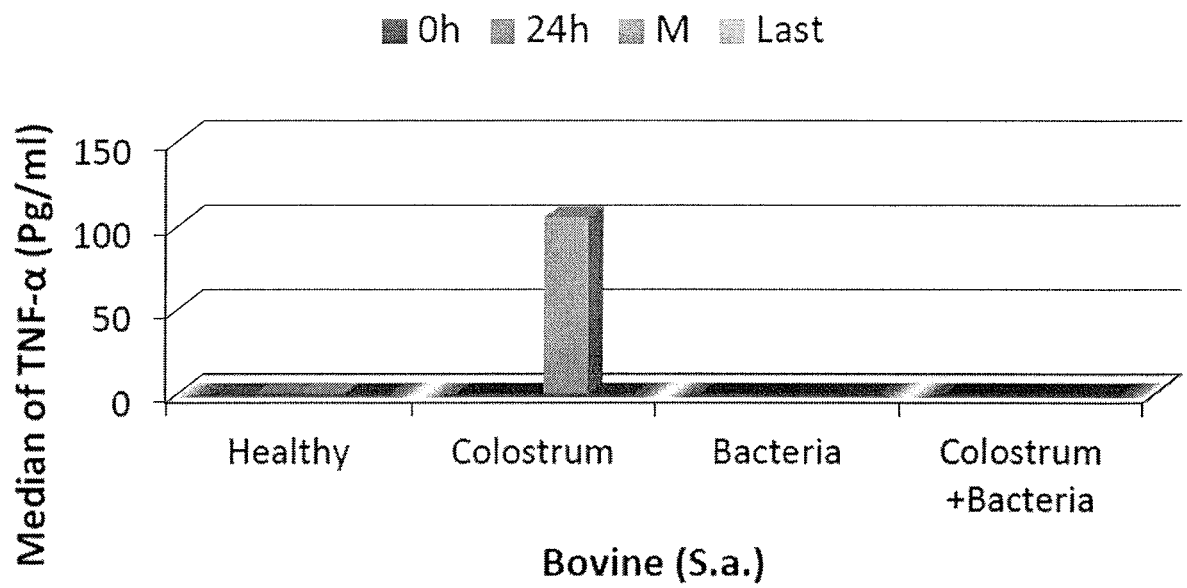
FIG. 16B depicts a bar graph displaying TNF-α levels over time in control subjects, subjects exposed to colostrum alone, subjects exposed to *S. aureus* alone, and subjects exposed to both *S. aureus* and colostrum, where the colostrum was bovine colostrum.
Figure 16C:
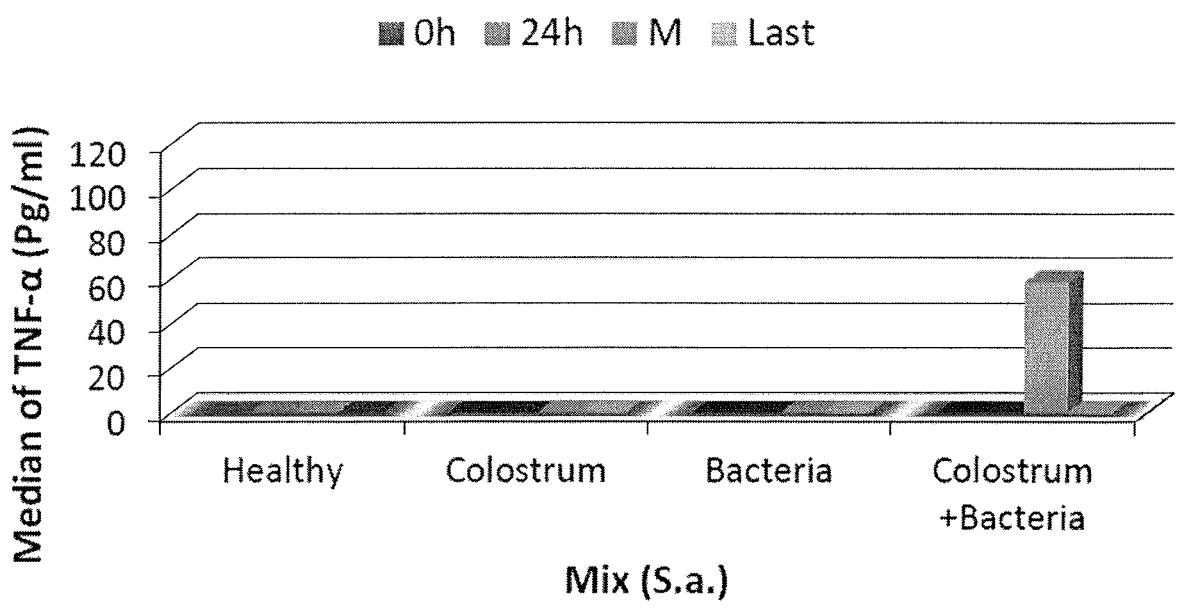
FIG. 16C depicts a bar graph displaying TNF-α levels over time in control subjects, subjects exposed to colostrum alone, subjects exposed to *S. aureus* alone, and subjects exposed to both *S. aureus* and colostrum, where the colostrum was a mixture of camel colostrum and bovine colostrum.

In the model of S. aureus subsp. aureus Rosenbach infection, the most excellent enhancement in TNF-α levels was observed after administration of camel colostrum, which had 0.56 pg./m., 1.21 pg./m and 0.50 pg./m for Colostrum, Bacteria, and Colostrum with Bacteria respectively (See Table 19 and FIG. 15). Data from the month-long experiment are presented in Table 20 and FIGS. 16A-16C.

TABLE 19

S. aureus and TNF-α Immune Response in the Presence of Colostrum (expressed as median pg/ml (Min-Max))

| | Colostrum Type: | | | |
|---|---|---|---|---|
| | Camel | Bovine | Mix | P value[A] |
| Healthy | 0.00(0.00-0.60) | 0.00(0.00-0.60) | 0.00(0.00-0.60) | 1.000 |
| Colostrum | 0.56(0.00-0.94) | 0.00(0.00-194.80) | 0.03(0.00-0.62) | 0.261 |

TABLE 19-continued

S. aureus and TNF-α Immune Response in the Presence of Colostrum (expressed as median pg/ml (Min-Max))

| | Colostrum Type: | | | |
|---|---|---|---|---|
| | Camel | Bovine | Mix | P value[A] |
| Bacteria | 1.21(0.00-9.85) | 0.00(0.00-0.00) | 0.00(0.00-1.09) | 0.002 |
| Colostrum & Bacteria | 0.50(0.00-6.55) | 0.00(0.00-0.00) | 0.12(0.00-116.44) | 0.014 |
| P value[B] | 0.043 | 0.118 | 0.931 |  |

[A]= Comparison between different treatments within a single Colostrum type using a Nonparametric Test (Kruskal-Wallis Test).
[B]= Comparison between different Colostrum types in each treatment using a Nonparametric Test (Kruskal-Wallis Test).

TABLE 20

S. aureus and TNF-α Immune Response in the Presence of Colostrum at 0 h, 24 h, 7-25 days (M), and 30 days (Last) (Expressed as Median(Min-Max))

| Treatment | Time | Camel | Bovine | Mix |
|---|---|---|---|---|
| Healthy | 0 h | 0.300(0.000-0.600) | 0.300(0.000-0.600) | 0.300(0.000-0.600) |
|  | 24 h | 0.220(0.000-0.440) | 0.220(0.000-0.440) | 0.220(0.000-0.440) |
|  | M | 0.269(0.000-0.540) | 0.269(0.000-0.540) | 0.269(0.000-0.540) |
|  | Last | 0.000(0.000-0.000) | 0.000(0.000-0.000) | 0.000(0.000-0.000) |
| P value |  | 0.675 | 0.675 | 0.675 |
| Colostrum | 0 h | 0.558(0.540-0.580) | 0.000(0.000-0.000) | 0.000(0.000-0.000) |
|  | 24 h | 0.828(0.720-0.940) | 0.000(0.000-0.000) | 0.000(0.000-0.000) |
|  | M | 0.430(0.170-0.690) | 104.749(14.70-194.80) | 0.177(0.050-0.300) |
|  | Last | 0.000(0.000-0.000) | 0.000(0.000-0.000) | 0.490(0.360-0.620) |
| P value |  | 0.108 | 0.077 | 0.078 |
| Bacteria | 0 h | 5.930(2.010-9.850) | 0.000(0.000-0.000) | 0.000(0.000-0.000) |
|  | 24 h | 0.962(0.720-1.210) | 0.000(0.000-0.000) | 0.000(0.000-0.000) |
|  | M | 0.900(0.580-1.220) | 0.000(0.000-0.000) | 0.185(0.000-0.360) |
|  | Last | 0.000(0.000-0.000) | 0.000(0.000-0.000) | 0.550(0.010-1.090) |
| P value |  | 0.185 | 1.000 | 0.100 |
| Colostrum & | 0 h | 6.184(5.820-6.550) | 0.000(0.000-0.000) | 0.000(0.000-0.000) |
| Bacteria | 24 h | 0.600(0.580-0.620) | 0.000(0.000-0.000) | 0.000(0.000-0.000) |
|  | M | 0.352(0.280-0.430) | 0.000(0.000-0.000) | 58.336(0.230-116.440) |
|  | Last | 0.000(0.000-0.000) | 0.000(0.000-0.000) | 0.589(0.560-0.620) |
| P value |  | 0.080 | 1.000 | 0.109 |

Figure 17:
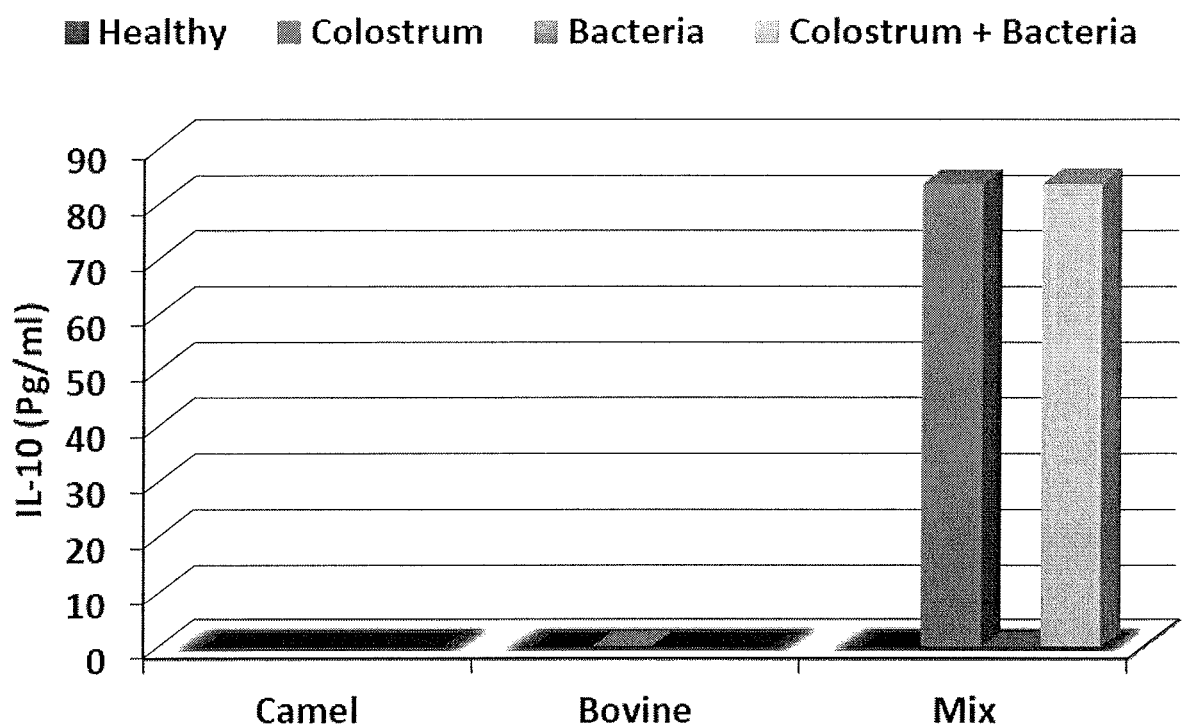
FIG. 17 depicts a bar graph displaying IL-10 levels in control subjects, subjects exposed to colostrum alone, subjects exposed to *S. aureus* alone, and subjects exposed to both *S. aureus* and colostrum, where the colostrum was either bovine colostrum, camel colostrum, or a mixture of bovine colostrum and camel colostrum.

In the model of *S. aureus* subsp. *aureus* Rosenbach infection, treatment with mixed colostrum alone and treatment with mixed colostrum and bacteria led to the highest increase in IL-10 levels (See Table 21 and FIG. 17).

TABLE 21

*S. aureus* and IL-10 Immune Response in the Presence of Colostrum (Expressed as Median pg/ml (Min-Max))

| | Colostrum Type: | | | |
|---|---|---|---|---|
| | Camel | Bovine | Mix | P value[A] |
| Healthy | 0.00(0.00-36.76) | 0.00(0.00-36.76) | 0.00(0.00-36.76) | 1.000 |
| Colostrum | 0.00(0.00-16.30) | 0.14(0.00-38.65) | 83.30(0.00-1000.00) | 0.115 |
| Bacteria | 0.00(0.00-0.98) | 0.04(0.00-23.78) | 0.07(0.00-500.00) | 0.023 |
| Colostrum & Bacteria | 0.00(0.00-0.07) | 0.03(0.00-0.39) | 83.38(0.01-1000.00) | 0.021 |
| P value[B] | 0.677 | 0.428 | 0.153 | |

[A] = Comparison between different treatments within a single Colostrum type using a Nonparametric Test (Kruskal-Wallis Test).
[B] = Comparison between different Colostrum types in each treatment using a Nonparametric Test (Kruskal-Wallis Test).

Figure 18A:
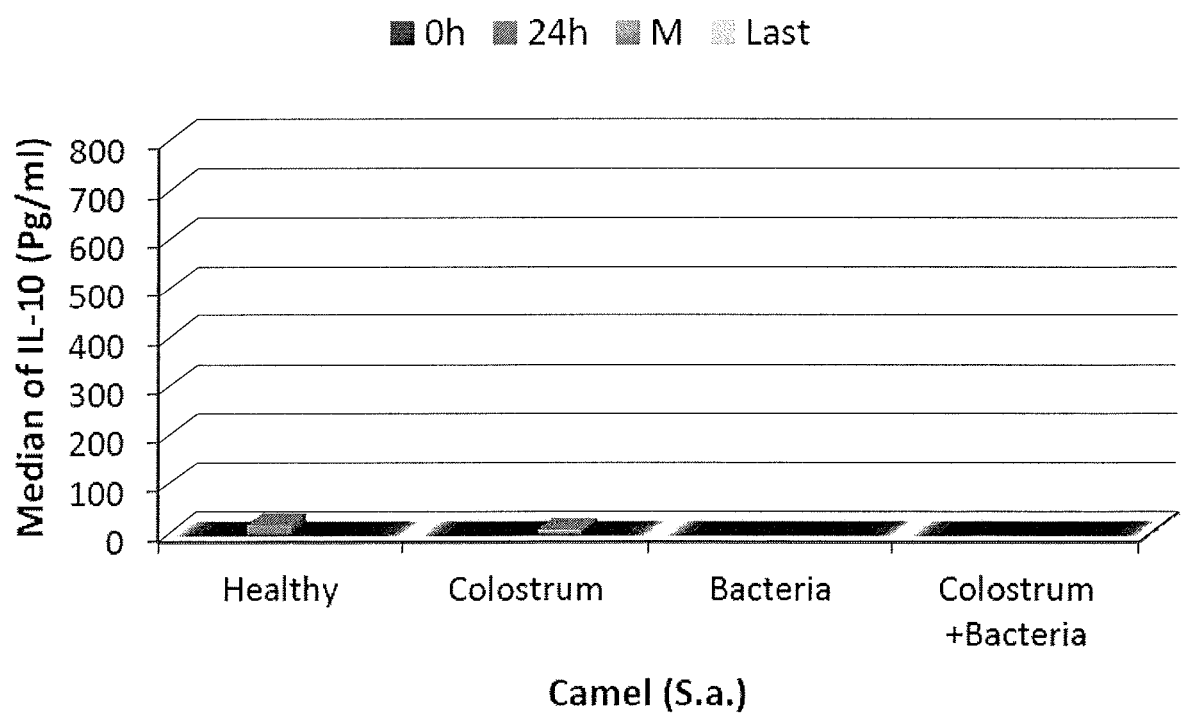
FIG. 18A depicts a bar graph displaying IL-10 levels over time in control subjects, subjects exposed to alone, subjects exposed to *S. aureus* alone, and subjects exposed to both *S. aureus* and colostrum, where the colostrum was camel colostrum.
Figure 18B:
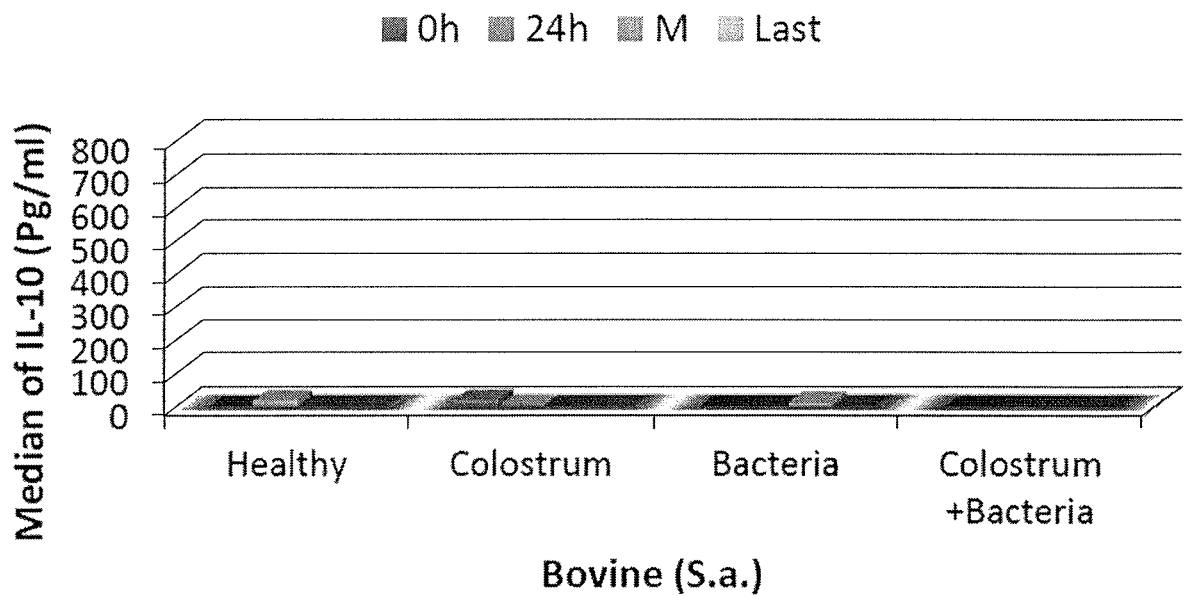
FIG. 18B depicts a bar graph displaying IL-10 levels over time in control subjects, subjects exposed to colostrum alone, subjects exposed to *S. aureus* alone, and subjects exposed to both *S. aureus* and colostrum, where the colostrum was bovine colostrum.
Figure 18C:
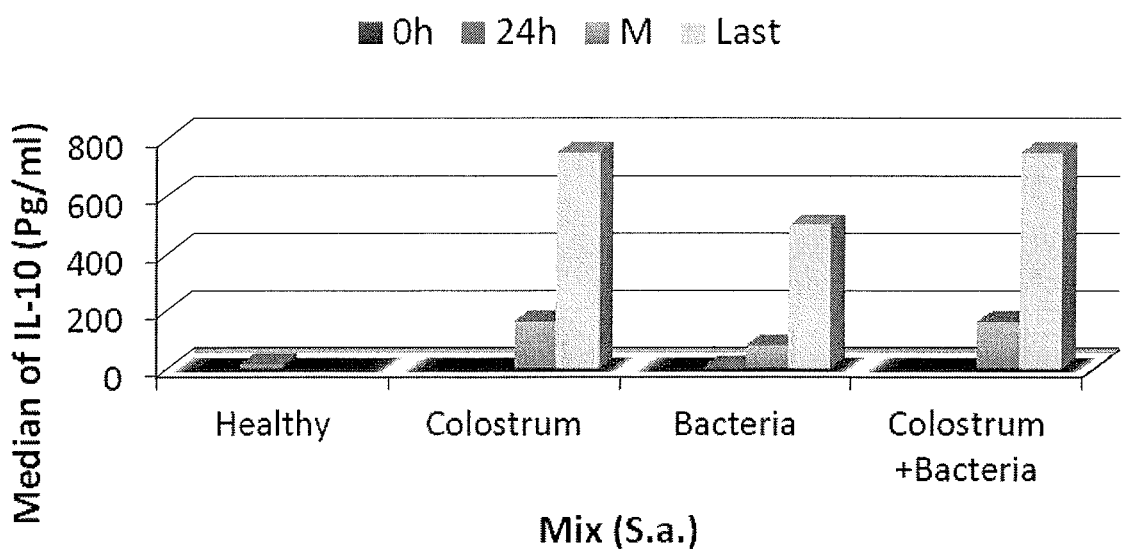
FIG. 18C depicts a bar graph displaying IL-10 levels over time in control subjects, subjects exposed to colostrum alone, subjects exposed to *S. aureus* alone, and subjects exposed to both *S. aureus* and colostrum, where the colostrum was a mixture of camel colostrum and bovine colostrum.

In the month-long experiment, treatment with mixed colostrum and treatment with either mixed colostrum alone or with mixed colostrum and bacteria resulted in a similar increase in IL-10 levels (166.63 and 166.60 respectively at 7-25 days and 750.00 pg/ml at the end of the month). These results are presented in Table 22 and FIGS. 18A-18C.

TABLE 22

*S. aureus* and IL-10 Immune Response in the Presence of Colostrum at 0 h, 24 h, 7-25 days (M), and 30 days (Last) (Expressed as Median(Min-Max))

| Treatment | Time | Camel | Bovine | Mix |
|---|---|---|---|---|
| Healthy | 0 h | 0.016(0.000-0.030) | 0.016(0.000-0.030) | 0.016(0.000-0.030) |
| | 24 h | 18.378(0.000-36.760) | 18.378(0.000-36.760) | 18.378(0.000-36.760) |
| | M | 0.018(0.000-0.030) | 0.018(0.000-0.030) | 0.018(0.000-0.030) |
| | Last | 0.004(0.000-0.010) | 0.004(0.000-0.010) | 0.004(0.000-0.010) |
| P value | | 0.935 | 0.935 | 0.935 |
| Colostrum | 0 h | 0.000(0.000-0.000) | 19.621(0.590-38.650) | 0.001(0.001-0.001) |
| | 24 h | 0.000(0.000-0.000) | 0.810(0.150-1.470) | 0.002(0.001-0.002) |
| | M | 8.152(0.000-16.300) | 0.077(0.020-0.130) | 166.63(166.60-166.66) |
| | Last | 0.005(0.005-0.005) | 0.001(0.000-0.001) | 750.00(500.0-1000.0) |
| P value | | 0.105 | 0.104 | 0.091 |
| Bacteria | 0 h | 0.491(0.000-0.980) | 0.089(0.010-0.170) | 0.029(0.020-0.040) |
| | 24 h | 0.000(0.000-0.000) | 0.040(0.020-0.060) | 8.914(0.070-17.760) |
| | M | 0.000(0.000-0.000) | 11.890(0.000-23.780) | 83.301(0.000-166.600) |
| | Last | 0.009(0.010-0.010) | 0.103(0.010-0.200) | 500.00(500.00-500.00) |
| P value | | 0.166 | 0.983 | 0.375 |
| Colostrum & Bacteria | 0 h | 0.001(0.000-0.000) | 0.216(0.040-0.390) | 0.010(0.010-0.010) |
| | 24 h | 0.000(0.000-0.000) | 0.012(0.000-0.020) | 0.085(0.010-0.160) |
| | M | 0.001(0.000-0.000) | 0.045(0.020-0.070) | 166.60(166.60-166.60) |
| | Last | 0.053(0.040-0.070) | 0.000(0.000-0.000) | 750.00(500.0-1000.0) |
| P value | | 0.143 | 0.276 | 0.100 |

Figure 19:
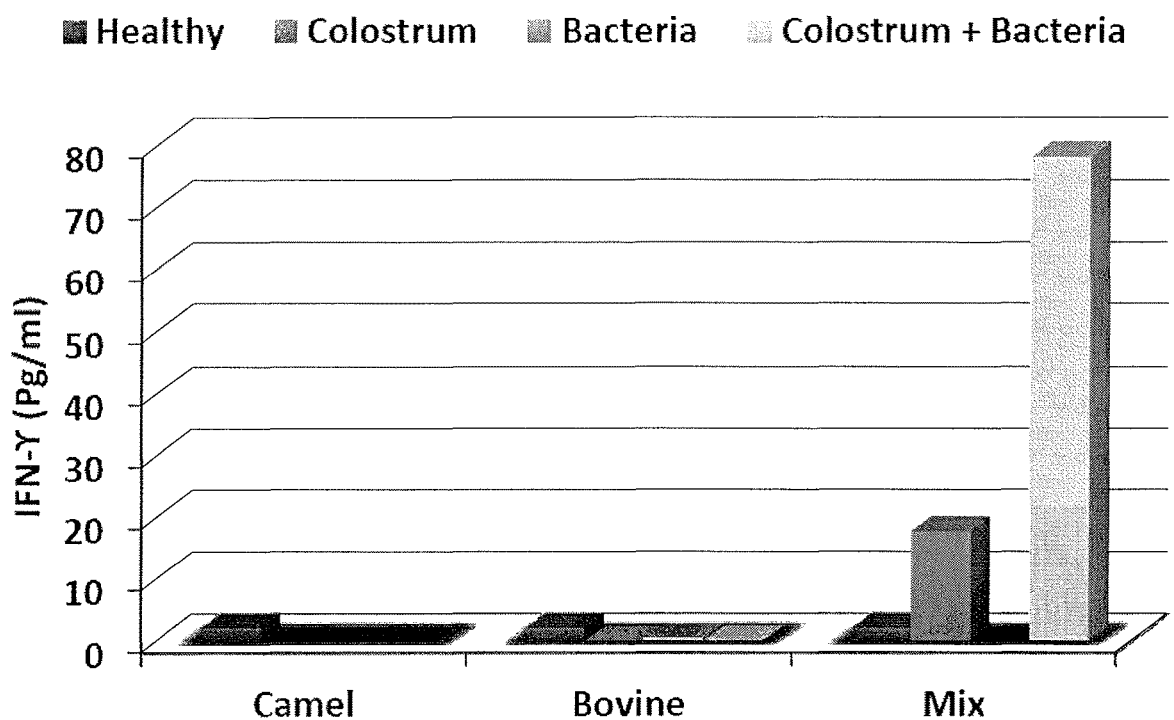
FIG. 19 depicts a bar graph displaying IFN-γ levels in control subjects, subjects exposed to colostrum alone, subjects exposed to MRSA, and subjects exposed to both MRSA and colostrum, where the colostrum was either bovine colostrum, camel colostrum, or a mixture of bovine colostrum and camel colostrum.
Figure 20A:
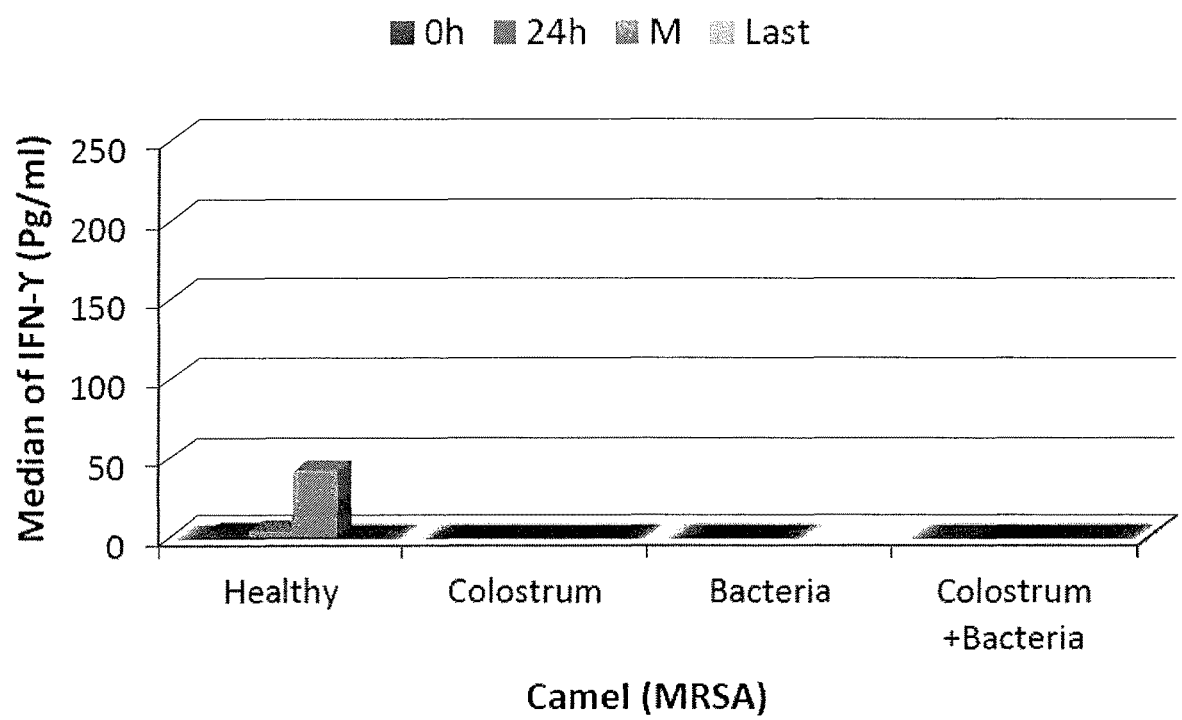
FIG. 20A depicts a bar graph displaying IFN-γ levels over time in control subjects, subjects exposed to colostrum alone, subjects exposed to MRSA alone, and subjects exposed to both MRSA and colostrum, where the colostrum was camel colostrum.
Figure 20B:
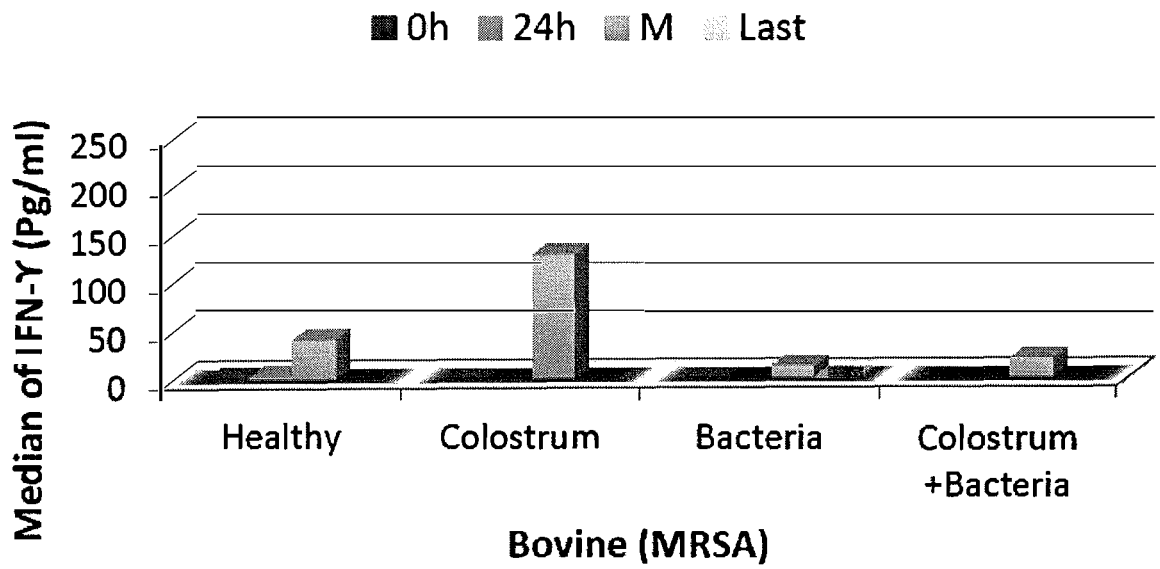
FIG. 20B depicts a bar graph displaying IFN-γ levels over time in control subjects, subjects exposed to colostrum alone, subjects exposed to MRSA alone, and subjects exposed to both MRSA and colostrum, where the colostrum was bovine colostrum.
Figure 20C:
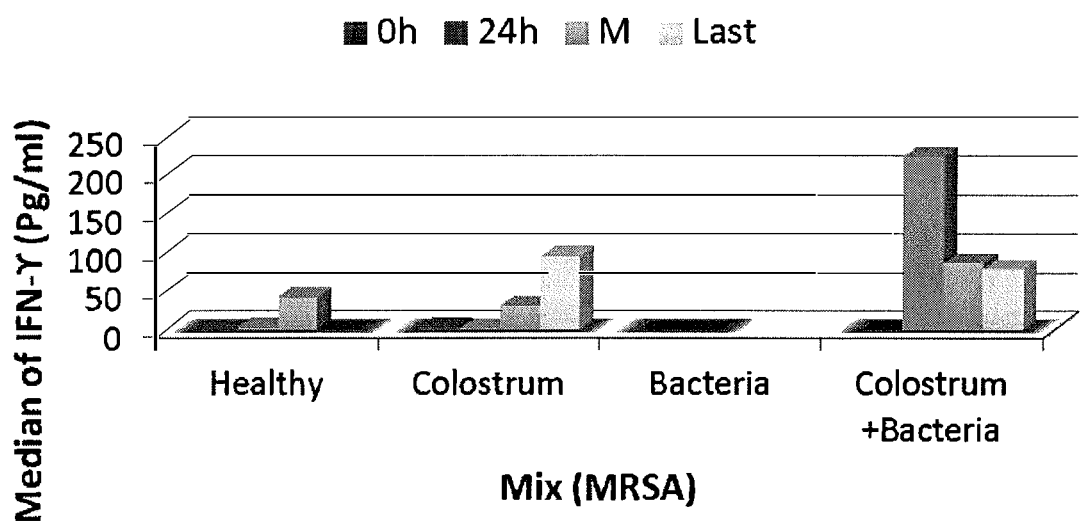
FIG. 20C depicts a bar graph displaying IFN-γ levels over time in control subjects, subjects exposed to colostrum alone, subjects exposed to MRSA alone, and subjects exposed to both MRSA and colostrum, where the colostrum was a mixture of camel colostrum and bovine colostrum.

In the model of MRSA infection, the administration of a lethal dose of MRSA also raised IFN-7 levels to 78.13 pg/ml when treated with mixed colostrum and bacteria. These results are similar to the IFN-7 levels reported above for rats administered a combination of mixed colostrum and *S. aureus* of 78.10 pg/ml. This result compares favorably to the IFN-γ levels reported for rats administered Bovine Colostrum and *S. aureus* of 23.76 pg/ml. Thus, these results confirm the improved immune response to treatment with mixed colostrum. The MRSA experimental results are summarized in Table 23 and FIG. 19. The month-long MRSA experimental results are summarized in Table 24 and FIGS. 20A-20C.

TABLE 23

MRSA and IFN-γ Immune Response in the Presence
of Colostrum (Expressed as Median pg/ml (Min-Max))

|  | Colostrum Type: | | | |
|---|---|---|---|---|
|  | Camel | Bovine | Mix | P value[A] |
| Healthy | 2.20(0.00-43.91) | 2.20(0.00-43.91) | 2.20(0.00-43.91) | 1.000 |
| Colostrum | 0.00(0.00-0.03) | 0.09(0.00-209.50) | 17.82(0.00-125.00) | 0.055 |
| Bacteria | 0.01(0.00-0.07) | 0.57(0.01-25.05) | 0.01(0.00-0.07) | 0.024 |
| Colostrum & Bacteria | 0.00(0.00-0.87) | 0.08(0.00-38.71) | 78.13(0.01-300.06) | 0.004 |
| P value[B] | 0.009 | 0.646 | 0.057 | |

[A] = Comparison between different treatments within a single Colostrum type using a Nonparametric Test (Kruskal-Wallis Test).
[B] = Comparison between different Colostrum types in each treatment using a Nonparametric Test (Kruskal-Wallis Test).

TABLE 24

MRSA and IFN-γ Immune Response in the Presence of Colostrum at 0
h, 24 h, 7-25 days (M), and 30 days (Last) (Expressed as Median(Min-Max))

| Treatment | Time | Camel | Bovine | Mix |
|---|---|---|---|---|
| Healthy | 0 h | 1.496(0.220-2.770) | 1.496(0.220-2.770) | 1.496(0.220-2.770) |
|  | 24 h | 3.587(1.630-5.550) | 3.587(1.630-5.550) | 3.587(1.630-5.550) |
|  | M | 42.175(40.440-43.910) | 42.175(40.440-43.910) | 42.175(40.440-43.910) |
|  | Last | 0.005(0.000-0.010) | 0.005(0.000-0.010) | 0.005(0.000-0.010) |
| P value |  | 0.104 | 0.104 | 0.104 |
| Colostrum | 0 h | 0.019(0.010-0.030) | 1.055(0.120-1.990) | 3.129(0.000-6.260) |
|  | 24 h | 0.002(0.000-0.000) | 0.058(0.060-0.060) | 1.667(0.000-3.330) |
|  | M | 0.002(0.000-0.000) | 128.800(48.10-209.50) | 30.327(29.390-31.260) |
|  | Last | 0.005(0.000-0.010) | 0.001(0.000-0.000) | 93.750(62.50-125.00) |
| P value |  | 0.160 | 0.078 | 0.106 |
| Bacteria | 0 h | 0.043(0.020-0.070) | 0.904(0.320-1.490) | 0.043(0.020-0.070) |
|  | 24 h | 0.007(0.000-0.010) | 0.046(0.010-0.080) | 0.007(0.000-0.010) |
|  | M | 0.000(0.000-0.000) | 12.798(0.540-25.050) | 0.000(0.000-0.000) |
|  | Last | 0.013(0.000-0.070) | 1.759(0.600-2.920) | 0.000(0.000-0.000) |
| P value |  | 0.121 | 0.212 | 0.121 |
| Colostrum & Bacteria | 0 h | 0.600(0.330-0.870) | 0.130(0.070-0.180) | 0.012(0.010-0.020) |
|  | 24 h | 0.001(0.000-0.000) | 0.056(0.020-0.090) | 222.78(145.50-300.06) |
|  | M | 0.002(0.000-0.000) | 20.951(3.190-38.710) | 85.565(53.92-117.21) |
|  | Last | 0.002(0.000-0.000) | 0.009(0.000-0.010) | 78.125(62.500-93.750) |
| P value |  | 0.104 | 0.104 | 0.112 |

Figure 21:
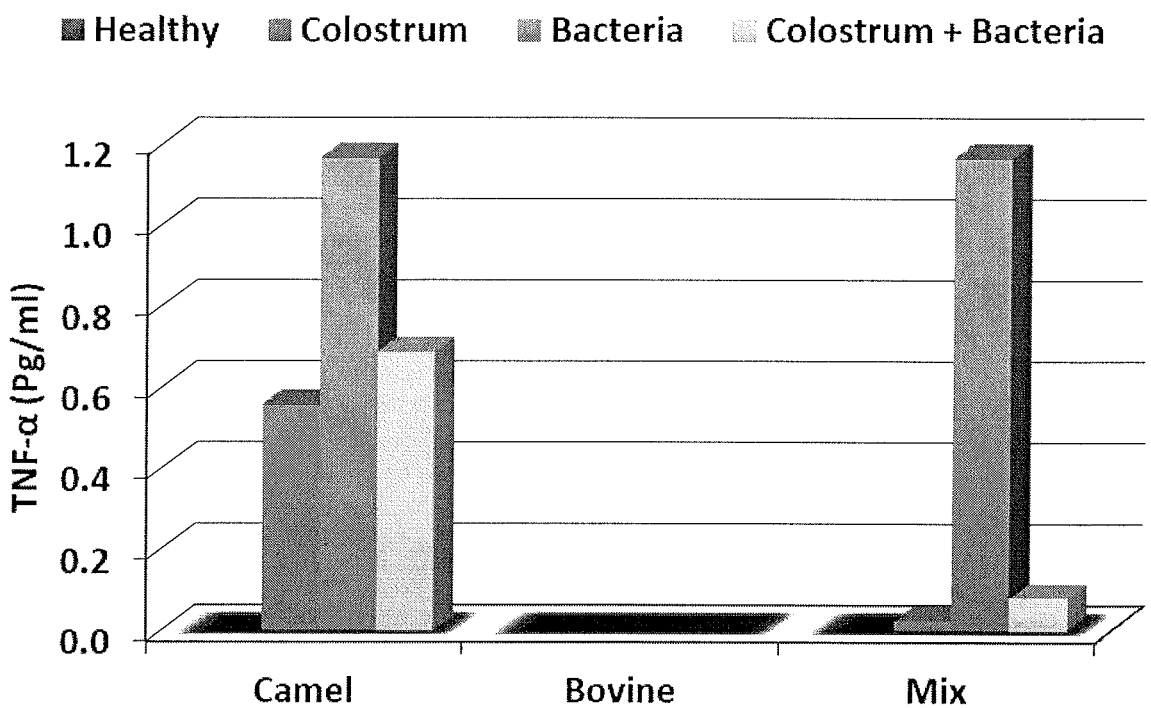
FIG. 21 depicts a bar graph displaying TNF-α levels in control subjects, subjects exposed to colostrum alone, subjects exposed to MRSA, and subjects exposed to both MRSA and colostrum, where the colostrum was either bovine colostrum, camel colostrum, or a mixture of bovine colostrum and camel colostrum.
Figure 22A:
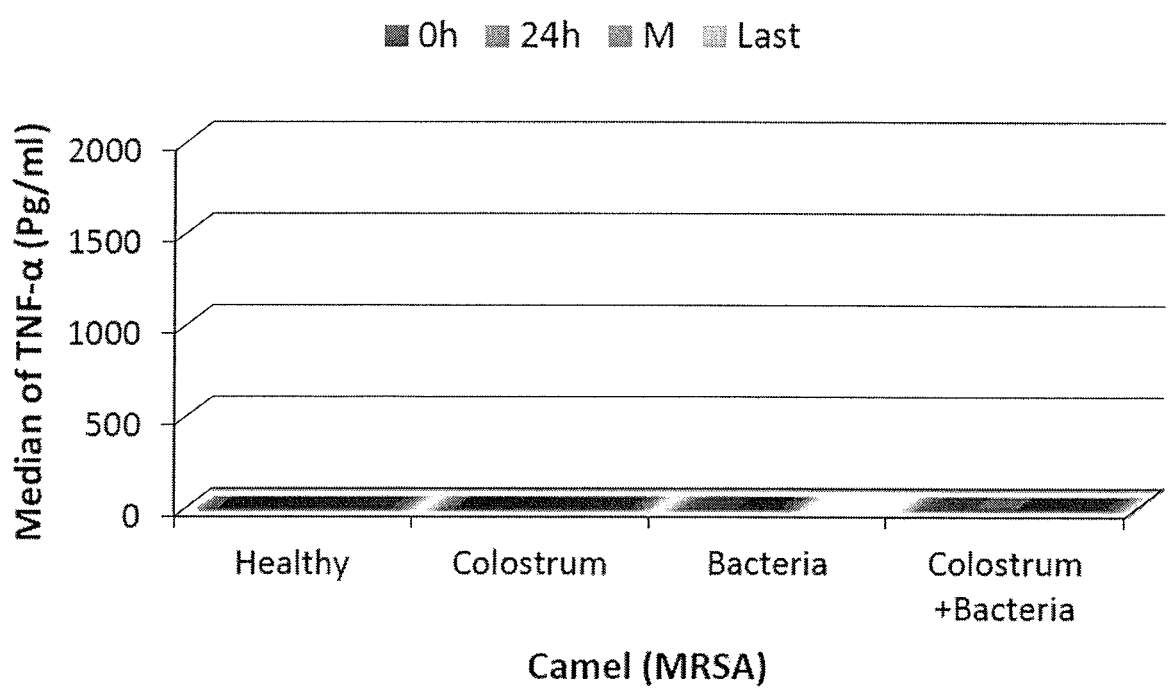
FIG. 22A depicts a bar graph displaying TNF-α levels over time in control subjects, subjects exposed to colostrum alone, subjects exposed to MRSA alone, and subjects exposed to both MRSA and colostrum, where the colostrum was camel colostrum.
Figure 22B:
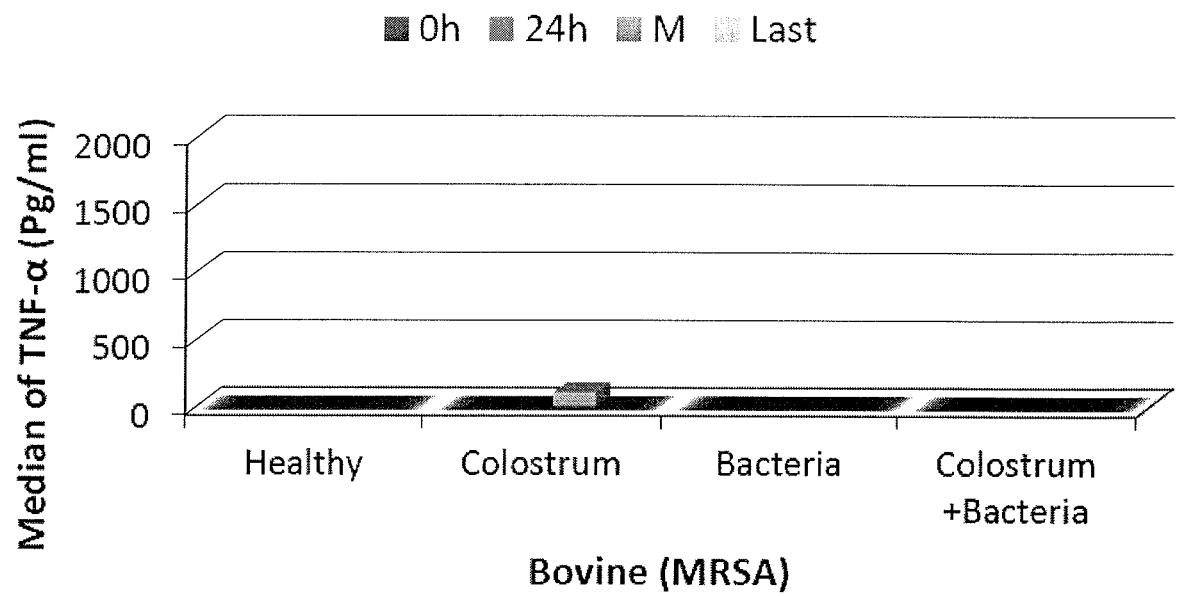
FIG. 22B depicts a bar graph displaying TNF-α levels over time in control subjects, subjects exposed to colostrum alone, subjects exposed to MRSA alone, and subjects exposed to both MRSA and colostrum, where the colostrum was bovine colostrum.
Figure 22C:
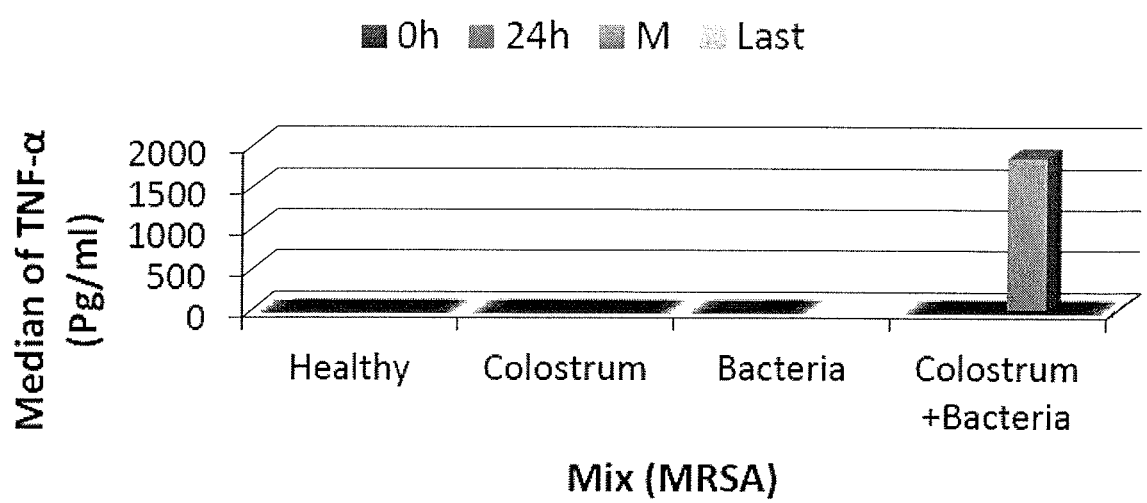
FIG. 22C depicts a bar graph displaying TNF-α levels over time in control subjects, subjects exposed to colostrum alone, subjects exposed to MRSA alone, and subjects exposed to both MRSA and colostrum, where the colostrum was a mixture of camel colostrum and bovine colostrum.

In the model of MRSA infection, administration of camel colostrum raised TNF-α levels to 0.56 pg/ml, compared to 0.03 pg/ml for the administration of mixed colostrum. The greatest increase in TNF-α levels was observed for camel colostrum, which recorded 0.69 pg/ml. These results are summarized in Table 25 and FIG. 21. The month-long experimental results are summarized in Table 26 and FIGS. 22A-22C.

TABLE 25

MRSA and TNF-α Immune Response in the Presence
of Colostrum (Expressed as Median pg/ml (Min-Max))

|  | Colostrum Type: | | | |
|---|---|---|---|---|
|  | Camel | Bovine | Mix | P value[A] |
| Healthy | 0.00(0.00-0.60) | 0.00(0.00-0.60) | 0.00(0.00-0.60) | 1.000 |
| Colostrum | 0.56(0.00-0.94) | 0.00(0.00-194.80) | 0.03(0.00-0.62) | 0.261 |
| Bacteria | 1.17(0.50-4.15) | 0.00(0.00-0.00) | 1.17(0.50-4.15) | 0.002 |
| Colostrum & Bacteria | 0.69(0.00-4.73) | 0.00(0.00-0.00) | 0.08(0.00-3707.00) | 0.013 |
| P value[b] | 0.064 | 0.118 | 0.050 | |

[A] = Comparison between different treatments within a single Colostrum type using a Nonparametric Test (Kruskal-Wallis Test).
[b] = Comparison between different Colostrum types in each treatment using a Nonparametric Test (Kruskal-Wallis Test).

TABLE 26

MRSA and TNF-α Immune Response in the Presence of Colostrum at 0 h, 24 h, 7-25 days (M), and 30 days (Last) (Expressed as Median(Min-Max))

| Treatment | Time | Camel | Bovine | Mix |
|---|---|---|---|---|
| Healthy | 0 h | 0.300(0.000-0.600) | 0.300(0.000-0.600) | 0.300(0.000-0.600) |
| | 24 h | 0.220(0.000-0.440) | 0.220(0.000-0.440) | 0.220(0.000-0.440) |
| | M | 0.269(0.000-0.540) | 0.269(0.000-0.540) | 0.269(0.000-0.540) |
| | Last | 0.000(0.000-0.000) | 0.000(0.000-0.000) | 0.000(0.000-0.000) |
| P value | | 0.675 | 0.675 | 0.675 |
| Colostrum | 0 h | 0.558(0.540-0.580) | 0.000(0.000-0.000) | 0.000(0.000-0.000) |
| | 24 h | 0.828(0.720-0.940) | 0.000(0.000-0.000) | 0.000(0.000-0.000) |
| | M | 0.430(0.170-0.690) | 104.749(14.70-194.80) | 0.177(0.050-0.300) |
| | Last | 0.000(0.000-0.000) | 0.000(0.000-0.000) | 0.490(0.360-0.620) |
| P value | | 0.108 | 0.077 | 0.078 |
| Bacteria | 0 h | 2.884(1.620-4.150) | 0.000(0.000-0.000) | 2.884(1.620-4.150) |
| | 24 h | 0.607(0.500-0.720) | 0.000(0.000-0.000) | 0.607(0.500-0.720) |
| | M | 0.000(0.000-0.000) | 0.000(0.000-0.000) | 0.000(0.000-0.000) |
| | Last | 1.166(0.500-4.150) | 0.000(0.000-0.000) | 0.000(0.000-0.000) |
| P value | | 0.121 | 1.000 | 0.121 |
| Colostrum & | 0 h | 4.098(3.470-4.730) | 0.000(0.000-0.000) | 0.000(0.000-0.000) |
| Bacteria | 24 h | 1.422(0.940-1.910) | 0.000(0.000-0.000) | 0.000(0.000-0.000) |
| | M | 0.383(0.330-0.440) | 0.000(0.000-0.000) | 1853.58(0.16-3707.00) |
| | Last | 0.000(0.000-0.000) | 0.000(0.000-0.000) | 0.622(0.560-0.680) |
| P value | | 0.080 | 1.000 | 0.109 |

Figure 23:
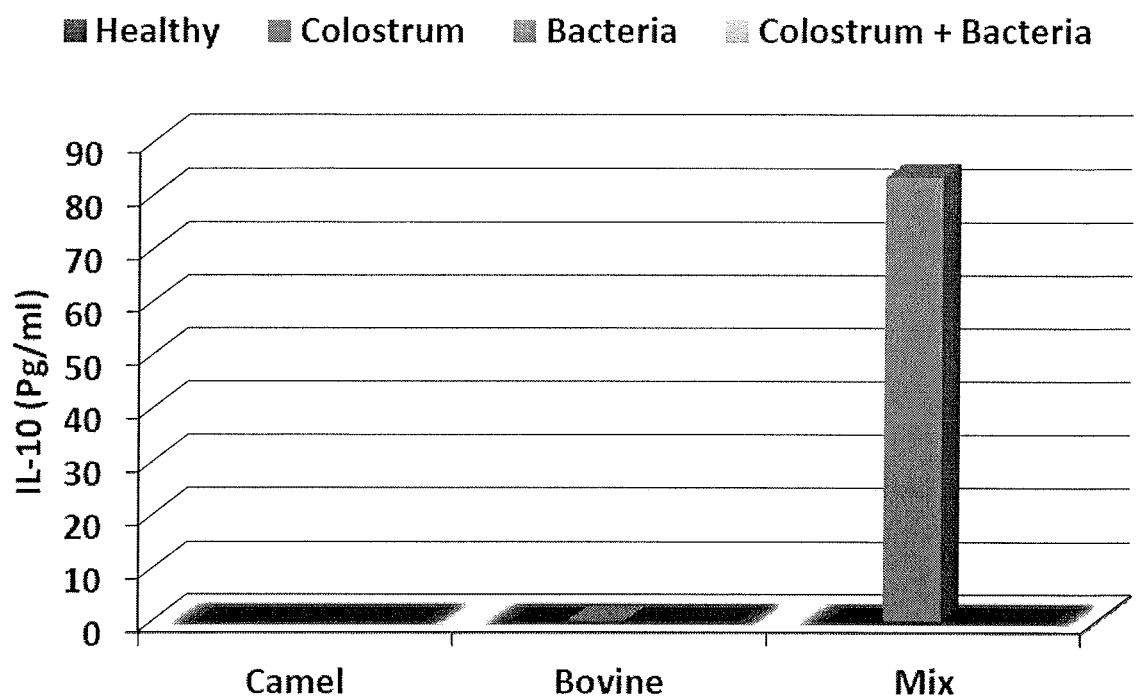
FIG. 23 depicts a bar graph displaying IL-10 levels in control subjects, subjects exposed to colostrum alone, subjects exposed to MRSA, and subjects exposed to both MRSA and colostrum, where the colostrum was either bovine colostrum, camel colostrum, or a mixture of bovine colostrum and camel colostrum.
Figure 24A:
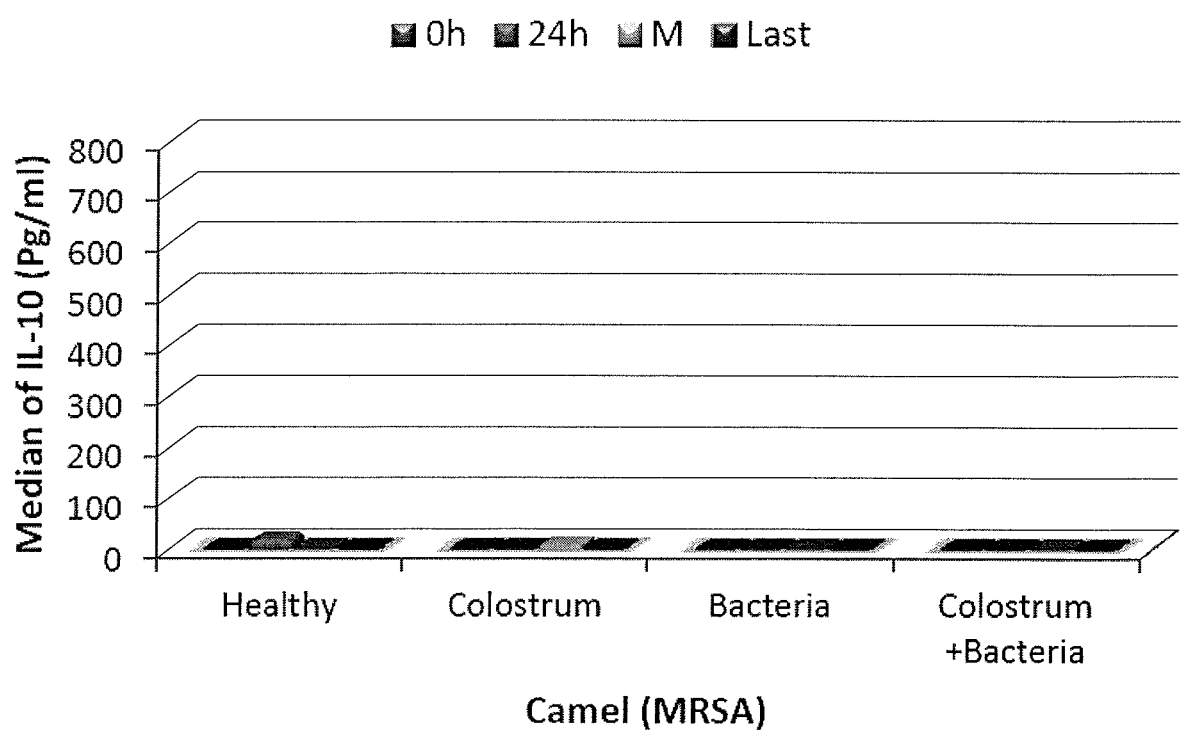
FIG. 24A depicts a bar graph displaying IL-10 levels over time in control subjects, subjects exposed to colostrum alone, subjects exposed to MRSA alone, and subjects exposed to both MRSA and colostrum, where the colostrum was camel colostrum.
Figure 24B:
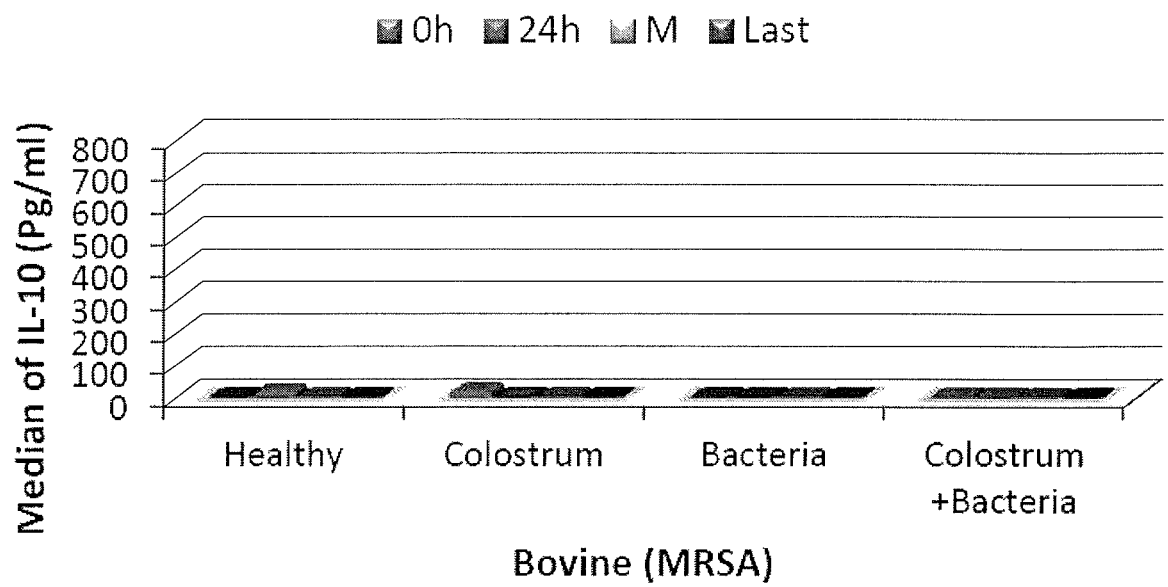
FIG. 24B depicts a bar graph displaying IL-10 levels over time in control subjects, subjects exposed to colostrum alone, subjects exposed to MRSA alone, and subjects exposed to both MRSA and colostrum, where the colostrum was bovine colostrum.
Figure 24C:
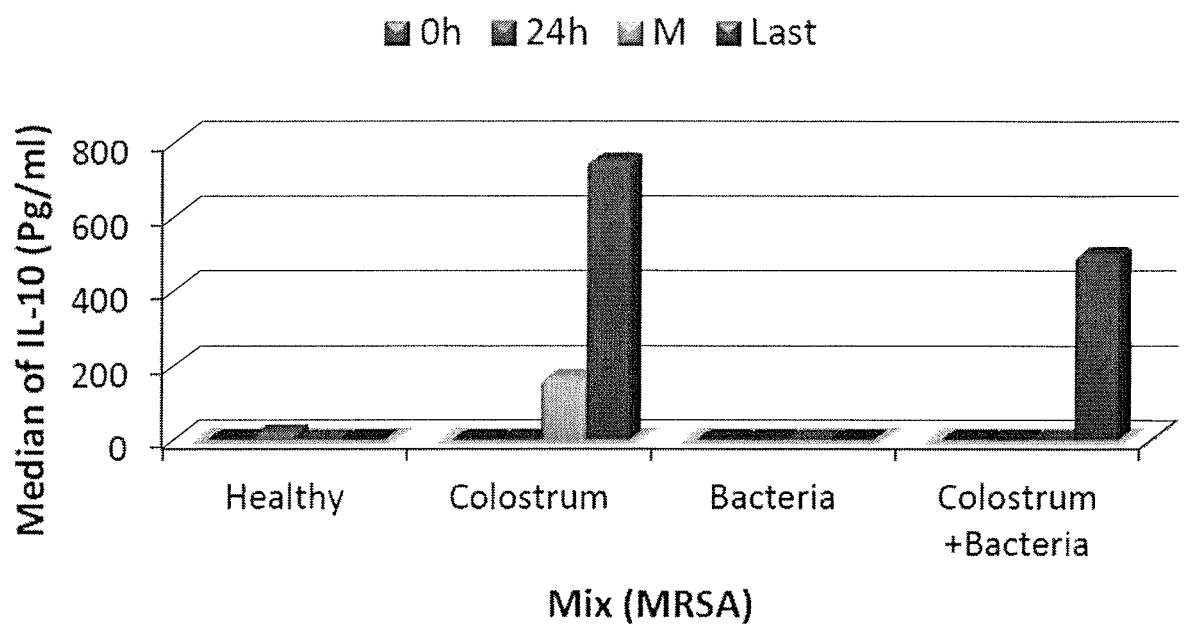
FIG. 24C depicts a bar graph displaying IL-10 levels over time in control subjects, subjects exposed to colostrum alone, subjects exposed to MRSA alone, and subjects exposed to both MRSA and colostrum, where the colostrum was a mixture of camel colostrum and bovine colostrum.

In the model of MRSA infection, administration of mixed colostrum raised IL-10 levels during the extended testing period to similar levels observed for *S. aureus*. Moreover, the administration of bovine colostrum increased IL-10 to 0.810 pg/ml after 24 hours. These results are summarized in Table 27 and FIG. 23. The month-long experimental results are summarized in Table 28 and FIGS. 24A-24C.

TABLE 27

MRSA and IL-10 Immune Response in the Presence of Colostrum (Expressed as Median pg/ml (Min-Max))

| | Colostrum Type: | | | |
|---|---|---|---|---|
| | Camel | Bovine | Mix | P value[A] |
| Healthy | 0.00(0.00-36.76) | 0.00(0.00-36.76) | 0.00(0.00-36.76) | 1.000 |
| Colostrum | 0.00(0.00-16.30) | 0.14(0.00-38.65) | 83.30(0.00-1000.00) | 0.115 |
| Bacteria | 0.00(0.00-0.00) | 0.04(0.02-0.34) | 0.00(0.00-0.00) | 0.001 |
| Colostrum & Bacteria | 0.00(0.00-0.04) | 0.03(0.00-6.41) | 0.01(0.00-500.00) | 0.035 |
| P value[B] | 0.057 | 0.348 | 0.002 | |

[A] = Comparison between different treatments within a single Colostrum type using a Nonparametric Test (Kruskal-Wallis Test).
[B] = Comparison between different Colostrum types in each treatment using a Nonparametric Test (Kruskal-Wallis Test).

TABLE 28

MRSA and IL-10 Immune Response in the Presence of Colostrum at 0 h, 24 h, 7-25 days (M), and 30 days (Last) (Expressed as Median(Min-Max))

| Treatment | Time | Camel | Bovine | Mix |
|---|---|---|---|---|
| Healthy | 0 h | 0.016(0.000-0.030) | 0.016(0.000-0.030) | 0.016(0.000-0.030) |
| | 24 h | 18.378(0.000-36.760) | 18.378(0.000-36.760) | 18.378(0.000-36.760) |
| | M | 0.018(0.000-0.030) | 0.018(0.000-0.030) | 0.018(0.000-0.030) |
| | Last | 0.004(0.000-0.010) | 0.004(0.000-0.010) | 0.004(0.000-0.010) |
| P value | | 0.935 | 0.935 | 0.935 |
| Colostrum | 0 h | 0.000(0.000-0.000) | 19.621(0.590-38.650) | 0.001(0.000-0.000) |
| | 24 h | 0.000(0.000-0.000) | 0.810(0.150-1.470) | 0.002(0.000-0.000) |
| | M | 8.152(0.000-16.300) | 0.077(0.020-0.130) | 166.63(166.60-166.66) |
| | Last | 0.005(0.000-0.000) | 0.001(0.000-0.000) | 750.00(500.0-1000.0) |

TABLE 28-continued

MRSA and IL-10 Immune Response in the Presence of Colostrum at 0 h, 24 h, 7-25 days (M), and 30 days (Last) (Expressed as Median(Min-Max))

| Treatment | Time | Camel | Bovine | Mix |
|---|---|---|---|---|
| P value | | 0.105 | 0.104 | 0.091 |
| Bacteria | 0 h | 0.000(0.000-0.000) | 0.207(0.070-0.340) | 0.000(0.000-0.000) |
| | 24 h | 0.000(0.000-0.000) | 0.024(0.020-0.020) | 0.000(0.000-0.000) |
| | M | 0.000(0.000-0.000) | 0.037(0.030-0.050) | 0.000(0.000-0.000) |
| | Last | 0.000(0.000-0.000) | 0.036(0.030-0.040) | 0.000(0.000-0.000) |
| P value | | 1.000 | 0.108 | 1.000 |
| Colostrum & | 0 h | 0.019(0.000-0.040) | 1.089(0.030-2.150) | 0.008(0.000-0.010) |
| Bacteria | 24 h | 0.000(0.000-0.000) | 3.225(0.040-6.410) | 0.006(0.000-0.010) |
| | M | 0.001(0.000-0.000) | 0.034(0.020-0.040) | 0.006(0.000-0.010) |
| | Last | 0.003(0.000-0.000) | 0.002(0.000-0.000) | 500.00(500.00-500.00) |
| P value | | 0.392 | 0.198 | 0.222 |

Overall, the *S. aureus* lethal dose experiments confirm that treatment with bovine colostrum resulted in lower stimulation of immune system cytokines than other tested treatments. For example, both the administration of colostrum mix alone and the administration of colostrum mix and the lethal dose of bacteria resulted in the same increase in IL-10 levels (83.30 pg/ml compared to administration of bacteria alone at 0.07 pg/ml) Administration of mixed colostrum alone and administration of mixed colostrum and bacteria raised IL-10 levels to 166.63 pg/ml at days 7-25 (M) and to 750.00 pg/ml by the final day of the experiment. Both camel colostrum and mixed camel colostrum and bovine colostrum stimulated TNF-α levels. The most enormous change was for camel colostrum in all treatments, which resulted in 0.56 pg/ml, 0.50 pg/ml, and 1.21 pg/ml for colostrum alone, bacteria alone, and colostrum and bacteria respectively.

Example 5

Calculating Correlations Between the Studied Cytokines and the Colostrum Sources The immunomodulatory effect of pro-inflammatory cytokines varied depending upon the bacterial species tested. IFN-γ exhibited a steady level of immune response in mixed colostrum treatment (93.750 pg/ml in the *E. coli* model). In the *S. aureus* model, IFN-γ levels increased to 78.10 pg/ml when the mixture of colostrum was administered compared to 17.82 pg/ml in the control colostrum. In the MRSA experiments, IFN-γ levels increased to 78.13 pg/ml when the mixed colostrum was administered. TNF-α, in the *P. aeruginosa* experiments showed the most considerable change in level when camel colostrum and bacteria were administered (8.931 pg/ml after 24 hours compared to 1.171 pg/ml for bacterial injection only).

IL-10 is a crucial cytokine marker. In *E. coli* treated with mixed colostrum, IL-10 was elevated to 83.30 pg/ml compared to 31.62 pg/ml when bacteria alone were administered. Early cytokine transcriptional changes could be useful as a forecasting tool. IL-10 started to increase after 24 hours in the *E. coli* experiments, up to 80.3080 pg/ml. In *S. aureus* administered mixed colostrum and bacteria, IL-10 levels rose to 166.60 pg/ml after 7-25 days, and this increase was sustained over time and ended with 750.00 pg/ml after one month.

The best survival effect was in camel colostrum and mixed colostrum for all the tested bacteria (83% in *E-coli*-100% in MRSA) in the infected rats in the presence of colostrum.

Camel colostrum and mixed colostrum blocked adherence of bacteria to cultured tissue cells. Mixed colostrum (bovine colostrum and camel colostrum) can stimulate the immune response more than the bovine colostrum or camel colostrum alone. Colostrum has been shown to be a constant source of potentially probiotic bacteria in an infant's gut, including staphylococci, streptococci, and lactic acid bacteria. The immunomodulatory effect of pro-inflammatory cytokines varied due to the bacterial species.

IL-10 and IFN-γ showed a significant interaction at 24 hours. The significant elevations of the IL-10 and TNF-α transcriptional levels most likely indicate their essential role in the regulation of the immune responses of the bovine mammary gland in *S. aureus* infection. That could reflect the suppressive nature of the *S. aureus* mastitis. Early cytokine transcriptional changes could be useful as a forecasting tool in the detection of the subclinical *S. aureus* mastitis. The transcriptional patterns of these cytokines in the early stages of *S. aureus* infection could help to unravel their role in the pathophysiology of *S. aureus* mastitis. Finally, vital, crucial cytokine marker(s) could emerge that provide efficient diagnostic and therapeutic means for the early detection of *S. aureus* mastitis. Early cytokine transcriptional changes could be useful as a forecasting tool in the detection of the subclinical *S. aureus* mastitis.

These experiments demonstrate that camel colostrum, bovine colostrum and mixed colostrum (bovine and camel colostrum) can provide protective and immune-stimulatory effects against the studied pathogenic bacteria in vitro and in vivo. The lyophilized colostrum derivative studied maintained most of the bioactive factors that appear to be at the basis of its many nutritional, modulatory, or even therapeutic, applications.

The fastest and the best-protected treatment was for lethal *S. aureus* with a baseline of 50-100% mortality. 100% survival was obtained for all six rats injected with *S. aureus* and administered the three types of colostrum by i.p. injection. Camel colostrum had a tremendous protective effect from lethal MRSA, demonstrating 100% survival versus 100% mortality in MRSA administration alone. Also, MRSA showed the highest maximum increased values in % change in weight of rats administered mixed colostrum (43% compared to −21% for rats administered only the lethal dose of MRSA).

Camel colostrum and mixed colostrum alone induced a remarkable increase in the weight of rats ranging from (6%-59%). Bacterial injection led to a dramatic decrease in the percent weight change in rats from −12% to 12%. MRSA demonstrated the most significant maximum increased values in percent change of weight of rats treated with mixed colostrum (43% compared to −21% when administered MRSA alone).

Calculations of the correlation between IFN-γ, IL-10, and TNF-α are summarized in Tables 29-31. Table 29 shows that without the presence of Colostrum, the value of the correlation coefficient between IL-10 and TNF-α was −0.773**, indicating a significant negative strength of association, while the value of the correlation coefficient between IFN-γ and TNF-α was 0.464*, demonstrating a less significant positive strength of association. With the presence of Colostrum, the only significant value of the correlation coefficient was 0.647**, between IL-10 and IFN-γ. In the absence of Colostrum, the administration of bacterial strains did not demonstrate a significant value of the correlation coefficient between the three tested cytokines in gram negative E. coli and P. aeruginosa; however, gram-positive S. aureus and MRSA has significant values of the correlation coefficient between IL-10 and IFN-γ. In the presence of both Colostrum and bacterial strains, the correlation coefficient between IL-10 and IFN-γ demonstrated a positive strength of association for S. aureus (0.701*) and MRSA (0.503*). Further, in the presence of E. coli, the correlation coefficient between IL-10 and TNF-α had a significant negative strength of association (−0.470*).

Table 30 shows the correlation between IFN-γ, IL-10, and TNF-α in the presence of Colostrum when treated with S. aureus or MRSA. A significant value of a correlation coefficient was observed in the presence of Camel Colostrum, with the coefficient between IL-10 and TNF-α having a negative strength of association for S. aureus of −0.517 and for MRSA of −0.585. A significant value of a correlation coefficient was observed in the presence of Bovine Colostrum, with the coefficient between IFN-γ and TNF-α having a positive strength of association for S. aureus of 0.415* and for MRSA of 0.551. A number of significant values of correlation coefficients were observed in the presence of Mixed Camel and Bovine Colostrum, with the coefficient between IFN-γ and IL-10, IFN-γ and TNF-α, and IL-10 and TNF-α all having respective positive strength of association for S. aureus of 0.659, 0.694**, and 0.439*. For MRSA, the coefficient between IFN-γ and IL-10 also showed a positive strength of association of 0.512**.

TABLE 29

Correlation between IFN-γ, IL-10, and TNF-α

| Treatments | Parameters | R (Spearman Correlation) | Sig. | |
|---|---|---|---|---|
| Healthy | IFN-γ with IL10 | −0.036 | 0.867 | N[b] |
| | IFN-γ with TNF-α | 0.464* | 0.022 | P[a] |
| | IL10 with TNF-α | −0.773** | 0.000 | N[b] |
| Colostrum | IFN-γ with IL10 | 0.647** | 0.001 | P[a] |
| | IFN-γ with TNF-α | 0.269 | 0.203 | P[a] |
| | IL10 with TNF-α | 0.025 | 0.908 | P[a] |
| E. coli | IFN-γ with IL10 | 0.242 | 0.267 | P[a] |
| | IFN-γ with TNF-α | 0.056 | 0.811 | P[a] |
| | IL10 with TNF-α | −0.295 | 0.207 | N[b] |
| Colostrum & E. coli | IFN-γ with IL10 | 0.353 | 0.151 | P[a] |
| | IFN-γ with TNF-α | −0.144 | 0.557 | N[b] |
| | IL10 with TNF-α | −0.470* | 0.049 | N[b] |
| P. aeruginosa | IFN-γ with IL10 | 0.490 | 0.054 | P[a] |
| | IFN-γ with TNF-α | −0.226 | 0.384 | N[b] |
| | IL10 with TNF-α | −0.329 | 0.214 | N[b] |
| Colostrum & P. aeruginosa | IFN-γ with IL10 | 0.186 | 0.418 | P[a] |
| | IFN-γ with TNF-α | −0.082 | 0.732 | N[b] |
| | IL10 with TNF-α | 0.150 | 0.528 | P[a] |

TABLE 29-continued

Correlation between IFN-γ, IL-10, and TNF-α

| Treatments | Parameters | R (Spearman Correlation) | Sig. | |
|---|---|---|---|---|
| S. aureus | IFN-γ with IL10 | 0.755** | 0.000 | P[a] |
| | IFN-γ with TNF-α | −0.168 | 0.443 | N[b] |
| | IL10 with TNF-α | −0.278 | 0.211 | N[b] |
| Colostrum & S. aureus | IFN-γ with IL10 | 0.701** | 0.000 | P[a] |
| | IFN-γ with TNF-α | 0.061 | 0.782 | P[a] |
| | IL10 with TNF-α | −0.135 | 0.550 | N[b] |
| MRSA | IFN-γ with IL10 | 0.796** | 0.000 | P[a] |
| | IFN-γ with TNF-α | −0.512* | 0.043 | N[b] |
| | IL10 with TNF-α | −0.863** | 0.000 | N[b] |
| Colostrum & MRSA | IFN-γ with IL10 | 0.503* | 0.014 | P[a] |
| | IFN-γ with TNF-α | 0.009 | 0.968 | P[a] |
| | IL10 with TNF-α | −0.288 | 0.182 | N[b] |

*= Correlation is significant at the 0.05 level.
**= Correlation is significant at the 0.01 level.
[a]= Positive correlation.
[b]= Negative correlation.

TABLE 30

Correlation between IFN-γ, IL-10, and TNF-α in the presence of colostrum for S. aureus and MRSA

| Colostrum Type | Parameters | R (Spearman Correlation) | Sig. | |
|---|---|---|---|---|
| S. aureus | | | | |
| Camel | IFN-γ with IL10 | 0.140 | 0.452 | P[a] |
| | IFN-γ with TNF-α | 0.090 | 0.628 | P[a] |
| | IL10 with TNF-α | −0.517** | 0.003 | N[b] |
| Bovine | IFN-γ with IL10 | 0.242 | 0.207 | P[a] |
| | IFN-γ with TNF-α | 0.415* | 0.020 | P[a] |
| | IL10 with TNF-α | −0.290 | 0.121 | N[b] |
| Mix | IFN-γ with IL10 | 0.659** | 0.000 | P[a] |
| | IFN-γ with TNF-α | 0.694** | 0.000 | P[a] |
| | IL10 with TNF-α | 0.439* | 0.013 | P[a] |
| MRSA | | | | |
| Camel | IFN-y with IL10 | 0.116 | 0.566 | P[a] |
| | IFN-y with TNF-α | 0.030 | 0.880 | P[a] |
| | IL10 with TNF-α | −0.585** | 0.001 | N[b] |
| Bovine | IFN-y with IL10 | 0.216 | 0.236 | P[a] |
| | IFN-y with TNF-α | 0.551** | 0.001 | P[a] |
| | IL10 with TNF-α | −0.325 | 0.070 | N[b] |
| Mix | IFN-y with IL10 | 0.512** | 0.005 | P[a] |
| | IFN-y with TNF-α | 0.221 | 0.258 | P[a] |
| | IL10 with TNF-α | −0.219 | 0.264 | N[b] |

*= Correlation is significant at the 0.05 level.
**= Correlation is significant at the 0.01 level.
[a]= Positive correlation.
[b]= Negative correlation.

Table 31 shows the correlation between IFN-γ, IL-10, and TNF-α in the presence of Colostrum when treated with E. coli or P. aeruginosa. A significant value of a correlation coefficient was observed in the presence of Camel Colostrum, with the coefficient between IL-10 and TNF-α having a negative strength of association for E. coli of −0.595. A significant value of a correlation coefficient was observed in the presence of Bovine Colostrum, with the coefficient between IFN-γ and TNF-α having a positive strength of association for E. coli of 0.559 and for P. aeruginosa of 0.548. A number of significant values of correlation coefficients were observed in the presence of Mixed Camel and Bovine Colostrum, with the coefficient between IFN-γ and TNF-α having a positive strength of association for E. coli of 0.625 and for P. aeruginosa of 0.739**. Further, significant values of correlation coefficients were observed in the presence of Mixed Camel and Bovine Colostrum, with the coefficient between IFN-γ and IL-10 also showing a positive strength of association of 0.412* for *E. coli* and of 0.374* for *P. aeruginosa*.

TABLE 31

Correlation between IFN-γ, IL-10, and TNF-α in the presence of colostrum for *E. coli* and *P. aeruginosa*

| Colostrum Type | Parameters | R (Spearman Correlation) | Sig. | |
|---|---|---|---|---|
| *E. coli* | | | | |
| Camel | IFN-γ with IL10 | 0.078 | 0.688 | P[a] |
| | IFN-γ with TNF-α | −0.203 | 0.282 | N[b] |
| | IL10 with TNF-α | −0.595** | 0.001 | N[b] |
| Bovine | IFN-γ with IL10 | 0.345 | 0.057 | P[a] |
| | IFN-γ with TNF-α | 0.559** | 0.002 | P[a] |
| | IL10 with TNF-α | −0.209 | 0.287 | N[b] |
| Mix | IFN-γ with IL10 | 0.413* | 0.026 | P[a] |
| | IFN-γ with TNF-α | 0.625** | 0.000 | P[a] |
| | IL10 with TNF-α | 0.210 | 0.274 | P[a] |
| *P. aeruginosa* | | | | |
| Camel | IFN-γ with IL10 | 0.088 | 0.664 | P[a] |
| | IFN-γ with TNF-α | −0.120 | 0.550 | N[b] |
| | IL10 with TNF-α | −0.043 | 0.832 | N[b] |
| Bovine | IFN-γ with IL10 | 0.198 | 0.323 | P[a] |
| | IFN-γ with TNF-α | 0.548** | 0.003 | P[a] |
| | IL10 with TNF-α | −0.277 | 0.162 | N[b] |
| Mix | IFN-γ with IL10 | 0.374* | 0.038 | P[a] |
| | IFN-γ with TNF-α | 0.739** | 0.000 | P[a] |
| | IL10 with TNF-α | 0.214 | 0.257 | P[a] |

*= Correlation is significant at the 0.05 level.
**= Correlation is significant at the 0.01 level.
[a]= Positive correlation.
[b]= Negative correlation.

Overall, these examples illustrate at least that mixed colostrum can trigger a greater immune response than the administration of either bovine colostrum or camel colostrum alone. Further, the administration of any of the three colostrum groups increased survival against lethal doses of gram-positive and gram-negative bacteria, with camel colostrum and mixed colostrum providing the greatest increase in survival.

It is to be understood that the methods described herein are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A colostrum composition comprising:
   a lyophilized colostrum and a saline solution, the lyophilized colostrum being made by the steps of:
   collecting colostrum from the mammary gland of a mammal; and
   freezing the colostrum at a temperature of at least −20° C. for at least a week;
   thawing the colostrum for at least 8 hours; and
   lyophilizing the colostrum; and
   wherein the lyophilized colostrum is suspended in the saline solution at a ration of 28 g lyophilized colostrum per liter saline solution to provide the colostrum composition.

2. A natural pharmaceutical composition comprising the colostrum composition of claim 1 and a pharmaceutically acceptable carrier.

* * * * *